US008158123B2

(12) United States Patent
Stashenko et al.

(10) Patent No.: US 8,158,123 B2
(45) Date of Patent: Apr. 17, 2012

(54) METHOD OF INHIBITING AN ACTIVITY OF A GENE PRODUCT IN A BONE CELL ENCODED BY A NUCLEOTIDE SEQUENCE COMPRISING SEQ ID NO: 50

(75) Inventors: Philip Stashenko, Medfield, MA (US); Yoshimura Okamatsu, Boston, MA (US); Hajime Sasaki, Needham, MA (US); Richard Battaglino, Boston, MA (US); Ulrike Späte, Boston, MA (US)

(73) Assignee: Forsyth Dental Infirmary for Children, Cambridge, MA (US)

( * ) Notice: Subject to any disclaimer, the term of this patent is extended or adjusted under 35 U.S.C. 154(b) by 377 days.

(21) Appl. No.: 10/734,692

(22) Filed: Dec. 11, 2003

(65) Prior Publication Data

US 2005/0214282 A1 Sep. 29, 2005

Related U.S. Application Data

(60) Provisional application No. 60/432,700, filed on Dec. 11, 2002.

(51) Int. Cl.
A61K 39/395 (2006.01)
(52) U.S. Cl. .................................................. 424/130.1
(58) Field of Classification Search .................. None
See application file for complete search history.

(56) References Cited

U.S. PATENT DOCUMENTS

2003/0186297 A1* 10/2003 Choi ................................. 435/6

OTHER PUBLICATIONS

Holliday et al., J. Biol. Chem. 272: 22053-22058, 1997.*
Votta et al., J. Bone and Miner. Res. 12: 1396-1406, 1997.*
Sugawara et al., Anal. Biochem. 255: 204-210, 1998.*
Battaglino, et al., *J. Bone Miner. Res.*, 17(5):763-773 (2002).
Budhram-Mahadeo, et al., *Int J. Biochem. Cell Biol.*, 33(10):1027-1039 (2001).
Budhram-Mahadeo, et al., *Oncogene*, 18(48):6684-6691 (1999).
Cappellen, et al., *J. Biol. Chem.*, 277(24):21971-21982 (2002).
Chambers, T.J., *J. Pathol.*, 192(1):4-13 (2000).
Chikazu, et al., *J. Biol. Chem.*, 275(40):31444-31450 (2000).
Choi, et al., *Blood*, 96(2):671-675 (2000).
Erkman, et al., *Nature*, 381(6583):603-606 (1996).
Erkman, et al., *Neuron*, 28(3):779-792 (2000).
Fedtsova; et al., *Mech. Dev.*, 53(3):291-304 (1995).
Franzoso, et al., *Genes Dev.*, 11:3482-3496 (1997).
Fuller, et al., *J. Immunol.*, 154(11):6065-6072 (1995).
Fuller, et al., *J. Exp. Med.*, 178(5):1733-1744 (1993).
Galibert, et al., *J. Biol. Chem.*, 273(51):34120-34127 (1998).
Gan, et al., *Proc. Natl. Acad. Sci. USA*, 93:3920-3925 (1996).
Gan, et al., *Dev. Biol.*, 210:469-480 (1999).
Gao, et al., *J. Exp. Med.*, 177(5):1421-1427 (1993).
Gerrero, et al., *Proc. Natl. Acad. Sci. USA*, 90:10841-10845 (1993).
Grigoriadis, et al., *Science*, 266:443-448 (1994).
Gruber, et al., *Mol. Cell. Biol.*, 17(5):2391-2400 (1997).
Han, et al., *Blood*, 97(11):3349-3353 (2001).
Hara, et al., *J. Immunol.*, 155(11):5352-5358 (1995).
Hayashi, et al., *Biochem. Cell Biol.*, 76(6):911-922 (1998).
Iotsova, et al., *Nat. Med.*, 3(11):1285-1289 (1997).
Itoh, et al., *J. Immunol.*, 170(7):3688-3695 (2003).
Jimi, et al., *Exp. Cell Res.*, 247(1):84-93 (1999).
Jimi, et al., *Endocrinology*, 136(2):808-811 (1995).
Jimi, et al., *J. Biol. Chem.*, 273(15):8799-8805 (1998).
Kong, et al., *Nature*, 402(6759):304-309 (1999).
Latchman, D.S., *J. Cell. Physiol.*, 179(2):126-133 (1999).
Lean, et al., *J. Cell. Biochem.*, 87:386-393 (2002).
Liu, et al., *Development*, 127:3237-3247 (2000).
Mansky, et al., *J. Biol. Chem.*, 277(13):11077-11083 (2002).
Mayo, et al., *Science*, 278:1812-1815 (1997).
McEvilly, et al., *Nature*, 384(6609):574-577 (1996).
McEvilly, et al., *Prog. Nucleic Acid Res. Mol. Biol.*, 63:223-255 (1999).
Mohamadzadeh, et al., *J. Immunol.*, 156(9):3102-3106 (1996).
Morris, et al., *Mol. Cell. Biol.*, 14(10):6907-6914 (1994).
Motyckova, et al., *Proc. Natl. Acad. Sci. USA*, 98(10):5798-5803 (2001).
Ninkina, et al., *Nucleic Acids Res.*, 21(14):3175-3182 (1993).
Poltorak, et al., *J. Inglamm.*, 45(3):207-219 (1995).
Reddy, et al., *Crit. Rev. Eukaryot. Gene Expr.*, 8(1):1-17 (1998).
Ryan, et al., *Genes Dev.*, 11(10):1207-1225 (1997).
Scheven, et al., *Biochem. Biophys. Res. Commun.*, 254(3):773-778 (1999).
Smith, et al., *Mol. Cell. Biol.*, 17(1):345-354 (1997).
Suda, et al., *Endocr. Rev.*, 20(3):345-357 (1999).
Takahashi, et al., *Endocrinology*, 122(4):1373-1382 (1988).
Takayanagi, et al., *Dev. Cell*, 3(6):889-901 (2002).
Teitelbaum, S.L., *Science*, 289(548)1504-1508 (2000).
Tokuda, et al., *J. Immunol.*, 164:2745-2751 (2000).
Turner, et al., *Neuron*, 12(1):205-218 (1994).
Udagawa, et al., *Bone*, 25(5):517-523 (1999).
Wang, et al., *Mol. Cel. Neurosci.*, 16(2):141-156 (2000).
Wang, et al., *Science*, 274:784-787 (1996).
Wang, et al., *Nature*, 360(6406):741-745 (1992).
Wang, et al., *Development*, 129:467-477 (2002).
Weilbaecher, et al., *Mol. Cell*, 8(4):749-758 (2001).
Wong, et al., *J. Leukocyte Biol.*, 65(6):715-724 (1999). Xiang, et al., *Cold Spring Harb. Symp. Quant. Biol.*, 62:325-336 (1997).
Xiang, et al., *Development*, 125:3935-3946 (1998).
Xiang, et al., *J. Neurosci.*, 15(7):4762-4785 (1995).
Xiang, et al., *Neuron*, 11(4):689-701 (1993).
Xiang, et al., *Proc. Natl. Acad. Sci. USA*, 94:9445-9450 (1997).
Xiang, et al., *Proc. Natl. Acad. Sci. USA*, 93:11950-11955 (1996).
Xing, et al., *J. Bone Miner. Res.*, 17(7):1200-1210 (2002).
Youn, et al., *Cytokine Reference* vol. 1, Oppenheim JJ, Feldman M, eds. Academic Press, San Diego, pp. 1237-1243.
GENBANK, Accession No. U 49513, Jun. 12, 1996.

(Continued)

*Primary Examiner* — Gyan Chandra
(74) *Attorney, Agent, or Firm* — Antoinette G. Giugliano, PC; AGG Intellectual Property Law

(57) ABSTRACT

The present invention features methods of treating a bone resorption disease or a bone generating disease, methods for prognosing and/or diagnosing a bone resorption disease or a bone generating disease, methods for identifying a compound that modulates bone resorption disease development or bone generating disease development, methods for determining the efficacy of a bone resorption disease therapy or a bone generating disease therapy, and oligonucleotide microarrays containing probes for genes involved in osteoclast development.

7 Claims, 30 Drawing Sheets

OTHER PUBLICATIONS

GENBANK, Accession No. NM 001295, Dec. 20, 2003.
GENBANK, Accession No. L 10918, Jun. 12, 1993.
GENBANK, Accession No. AF 043341, Feb. 21, 1998.
GENBANK, Accession No. S 69350, Jun. 13, 2000.
GENBANK, Accession No. U 10062, Dec. 14, 1994.
GENBANK, Accession No. U 10063, Dec. 14, 1994.
GENBANK, Accession No. S 69351, Mar. 20, 2002.
GENBANK, Accession No. U 06233, Mar. 8, 1994.
GENBANK, Accession No. S 69352, Mar. 20, 2002.
GENBANK, Accession No. U 10060, Dec. 14, 1994.
GENBANK, Accession No. U 10061, Dec. 14, 1994.

* cited by examiner

| Analysis Name | Probe Set Name | | Gene Name | Change | Change | Status | Change p-value | Change p-value |
|---|---|---|---|---|---|---|---|---|
| A (U74A) | 100581_at | 1 | cystatin B (Stfb) gene | 1 | 1 | 1 | 0 | 0 |
| A (U74A) | 103946_at | 2 | Pstpipl (proline-serine-threonine phosphayase-interacting protein 1) | 1 | 1 | 1 | 0 | 0 |
| A (U74A) | 104388_at | 3 | Scya9 (small inducible cytokine A9) | 1 | 1 | 1 | 0 | 0 |
| A (U74A) | 104407_at | 4 | Alcam (activated leukocyte cell adhesion molecule) | 1 | 1 | 1 | 0 | 0 |
| A (U74A) | 104761_at | 5 | 2310046B19Rik RIKEN cDNA 2310046B19 gene) | 1 | 1 | 1 | 0 | 0 |
| A (U74A) | 160202_at | 6 | 5730403E06Rik (RIKEN cDNA 5730403E06 gene) | 1 | 1 | 1 | 0 | 0 |
| A (U74A) | 160406_at | 7 | ctsk gene | 1 | 1 | 1 | 0 | 0 |
| A (U74A) | 160901_at | 8 | c-fos oncogene | 1 | 1 | 1 | 0 | 0 |
| A (U74A) | 98859_at | 9 | Acid phosphatase type 5 gene | 1 | 1 | 1 | 0 | 0 |
| A (U74A) | 99957_at | 10 | Mmp9 (matrix metalloproteinase 9) | 1 | 1 | 1 | 0 | 0 |
| A (U74A) | 103017_at | 11 | Tm7sf1 (transmembrane 7 superfamily member 1, integral membrane protein) | 1 | 1 | 1 | 0 | 0.000001 |
| A (U74C) | 166517_f_at | 12 | Alcam (activated leukocyte cell adhesion molecule) | 1 | 1 | 1 | 0 | 0.000001 |
| A (U74A) | 94556_at | 13 | 2410004M09Rik (RIKEN cDNA 2410004M09). | 1 | 1 | 1 | 0 | 0.000001 |
| A (U74A) | 96481_at | 14 | C80638 (AV251613 RIKEN full-length enriched, 0 day neonate head Mus musculus cDNA clone 4833432F11 3', mRNA sequence) | 1 | 1 | 1 | 0.000001 | 0 |
| A (U74A) | 97302_at | 15 | 1700126I16Rik (NDI-S, gene with protein product, function known or inferred) | 1 | 1 | 1 | 0.000001 | 0 |
| A (U74A) | 100906_at | 16 | Itgb7 (integrin beta 7) | 1 | 1 | 1 | 0.000001 | 0.000001 |
| A (U74A) | 103210_at | 17 | Csf2rb2 (colony stimulating factor 2 receptor, beta 2) | 1 | 1 | 1 | 0.000001 | 0.000001 |
| A (U74A) | 103690_at | 18 | AW125574 (Williams-Beuren syndrome chromosome region 5 homolog) | 1 | 1 | 1 | 0.000001 | 0.000001 |
| A (U74A) | 160124_r_at | 19 | vacuolar adenosine triphosphatase subunit C mRNA | 1 | 1 | 1 | 0.000001 | 0.000001 |
| A (U74C) | 165770_at | 20 | A1851927 (expressed sequence A1851927) | 1 | 1 | 1 | 0 | 0.000002 |
| A (U74A) | 93037_i_at | 21 | lipocortin l gene, exon 13 | 1 | 1 | 1 | 0.000001 | 0.000001 |
| A (U74A) | 96680_at | 22 | Dna j b9 (Dna j (Hsp40) homolog, chaperone) | 1 | 1 | 1 | 0 | 0.000002 |
| A (U74A) | 102348_at | 23 | pale ear (Hermansky-Pudlak syndrome l homolog) | 1 | 1 | 1 | 0 | 0.000002 |
| A (U74B) 2 | 107969_at | 24 | Alcam (activated leukocyte cell adhesion molecule) | 1 | 1 | 1 | 0 | 0.000003 |
| A (U74A) | 92648_at | 25 | Stxbp3 (intracellular protein traffic) | 1 | 1 | 1 | 0.000003 | 0 |
| A (U74A) | 95745_g_at | 26 | vacuolar adenosine triphosphatase subunit A gene | 1 | 1 | 1 | 0.000003 | 0 |
| A (U74A) | 98884_r_at | 27 | Nudel-pending (nuclear distribution gene E-like, centrosome) | 1 | 1 | 1 | 0.000001 | 0.000002 |
| A (U74A) | 101554_at | 28 | I kappa B alpha gene, exons 2-6 | 1 | 1 | 1 | 0.000004 | 0 |
| A (U74C) | 167230_f_at | 29 | ESTs, Moderately similar to ANX4 MOUSE ANNEXIN IV | 1 | 1 | 1 | 0.000001 | 0.000003 |
| A (U74B) 2 | 116346_at | 30 | 4930506M07Rik (RIKEN cDNA 4930506M07 gene) | 1 | 1 | 1 | 0.000003 | 0.000002 |
| A (U74A) | 101042_f_at | 31 | Pep4 (peptidase 4, metalloendopeptidase) | 1 | 1 | 1 | 0 | 0.000005 |
| A (U74A) | 103923_at | 32 | transmembrane 7 superfamily member 1 | 1 | 1 | 1 | 0.000005 | 0 |

Fig. 1A-1

| Analysis Name | Probe Set Name | | Gene Name | Change | Change | Status | Change p-value | Change p-value |
|---|---|---|---|---|---|---|---|---|
| A (U74A) | 104179_at | 33 | AI788669 (expressed sequence AI788669) | | 1 | 1 | 0.000005 | 0 |
| A (U74A) | 160529_r_at | 34 | Vdac2 (voltage-dependent anion channel 2) | 1 | 1 | | 0 | 0.000005 |
| A (U74A) | 104106_at | 35 | Rp17 (ribosomal protein L7) | 1 | 1 | | 0.000003 | 0.000003 |
| A (U74A) | 94346_at | 36 | Wtap-pending (Wilms' tumour 1-associating protein) | 1 | 1 | | 0.000005 | 0.000001 |
| A (U74B) 2 | 115453_at | 37 | A1324824 (expressed sequence A1324824) | 1 | 1 | | 0.000007 | 0 |
| A (U74A) | 99413_at | 38 | Cmkbr1 (chemokine (C-C) receptor 1) | 1 | 1 | | 0.000007 | 0 |
| A (U74A) | 102283_at | 39 | Tiam1 (T-cell lymphoma invasion and metastasis 1) | 1 | 1 | | 0 | 0.000008 |
| A (U74A) | 161173_f_at | 40 | ESTs, similar to M31418 Mouse 202 interferon-activatable protein mRNA | 1 | 1 | | 0.000001 | 0.000007 |
| A (U74C) | 139395_at | 41 | ESTs (Soares mouse NbMH) | 1 | 1 | | 0.000005 | 0.000003 |
| A (U74B) 2 | 162543_r_at | 42 | Acp5 (acid phosphatase 5, tartrate resistant) | 1 | 1 | | 0.000007 | 0.000002 |
| A (U74A) | 92642_at | 43 | Car2 (carbonate dehydratase) | 1 | 1 | | 0.000009 | 0 |
| A (U74A) | 104149_at | 44 | Nfkbia (nuclear factor of kappa light chain gene enhancer in B-cells inhibitor, alpha) | 1 | 1 | | 0.000011 | 0 |
| A (U74A) | 160539_at | 45 | ASF mRNA | 1 | 1 | | 0.000009 | 0.000002 |
| A (U74A) | 100990_g_at | 46 | Itgb1bp1 (integrin beta 1 binding protein 1) | 1 | 1 | | 0.000008 | 0.000004 |
| A (U74A) | 168548_f_at | 47 | ESTs, Moderately similar to SUPEROXIDE DISMUTASE | 1 | 1 | | 0.000001 | 0.000011 |
| A (U74C) | 103922_f_at | 48 | 1500005G05Rik (RIKEN cDNA 1500005G05 gene) | 1 | 1 | | 0.000002 | 0.000011 |
| A (U74B) 2 | 94871_r_at | 49 | 2900019122Rik (gene with protein product, function unknown) | 1 | 1 | | 0.000012 | 0.000001 |
| A (U74A) | 96634_at | 50 | 5730469M10Rik (gene with protein product, function unknown) | 1 | 1 | | 0.000004 | 0.000009 |
| A (U74A) | 92302_at | 51 | Sos2 (Son of sevenless homolog 2) | 1 | 1 | | 0 | 0.000014 |
| A (U74A) | 99993_at | 52 | Anpep (alanyl (membrane) aminopeptidase) | 1 | 1 | | 0 | 0.000014 |
| A (U74B) 2 | 109102_r_at | 53 | 2210023K21Rik (RIKEN cDNA 2210023K21 gene) | 1 | 1 | | 0.000009 | 0.000006 |
| A (U74C) | 169068_i_at | 54 | 4930434J08Rik (RIKEN cDNA 4930434J08 gene) | 1 | 1 | | 0.000005 | 0.00001 |
| A (U74C) | 168377_r_at | 55 | Spphl-pending (sphingosine-1-phosphate phosphatase 1) | 1 | 1 | | 0.000004 | 0.000013 |
| A (U74A) | 160092_at | 56 | Ifrd1 (interferon-related developmental regulator 1) | 1 | 1 | | 0.000017 | 0.000001 |
| A (U74A) | 93471_at | 57 | ESTs, Weakly similar to T14031 sodium bicarbonate cotransporter, pancreatic - mouse | 1 | 1 | | 0.000003 | 0.000015 |
| A (U74A) | 104206_at | 58 | 0610012A05Rik (RIKEN cDNA 0610012A05 gene) | 1 | 1 | | 0.000017 | 0.000002 |
| A (U74A) | 161703_f_at | 59 | Anxa1 (annexin A1) | 1 | 1 | | 0.000018 | 0.000001 |
| A (U74A) | 94733_at | 60 | Abcn4 (ATP-binding cassette, sub-family B (MDR/TAP), member 4) | 1 | 1 | | 0.000001 | 0.000018 |
| A (U74A) | 100380_at | 61 | H3 3A variant histone | 1 | 1 | | 0.000013 | 0.000007 |
| A (U74B) 2 | 164245_at | 62 | ESTs, Highly similar to hypothetical protein | 1 | 1 | | 0.000012 | 0.000008 |
| A (U74A) | 100584_at | 63 | Anxa4 (annexin A4, calcium binding) | 1 | 1 | | 0.000001 | 0.000021 |

Fig. 1A-2

| Analysis Name | Probe Set Name | | Gene Name | Change | Change | Change Status | Change p-value | Change p-value |
|---|---|---|---|---|---|---|---|---|
| A (U74B)2 | 115949_at | 64 | ESTs (vg72c11.x1 Soares mouse NbMII) | 1 | | 1 | 0.000021 | 0.000001 |
| A (U74A) | 95625_at | 65 | AA589632 (expressed sequence AA589632) | 1 | 1 | 1 | 0.000003 | 0.000019 |
| A (U74A) | 92597_s_at | 66 | vacuolar adenosine triphosphatase subunit B gene | 1 | 1 | 1 | 0.000023 | 0.000001 |
| A (U74A) | 100499_at | 67 | Stx3 (syntaxin 3) | 1 | 1 | 1 | 0 | 0.000025 |
| A (U74A) | 95746_at | 68 | Atp6al (hydrogen-transporting two-sector ATPase) | 1 | 1 | 1 | 0.000015 | 0.00001 |
| A (U74A) | 100042_at | 69 | Similar to hydroxyacyl glutathione hydrolase | 1 | 1 | 1 | 0.000025 | 0.000005 |
| A (U74A) | 96875_r_at | 70 | 1200003J11Rik (RIKEN cDNA 1200003J11 gene) | 1 | 1 | 1 | 0.000007 | 0.000025 |
| A (U74A) | 103783_at | 71 | Xpr1 (xenotropic and polytropic retrovirus receptor 1) | 1 | 1 | 1 | 0.000029 | 0.000004 |
| A (U74A) | 103328_at | 72 | Tank (TRAF family member-associated Nf-kappa B activator) | 1 | 1 | 1 | 0.000025 | 0.000009 |
| A (U74A) | 138577_at | 73 | Atp6b2 (ATPase, H+ transporting, lysosomal) | 1 | 1 | 1 | 0.000018 | 0.000018 |
| A (U74C) | 168443_r_at | 74 | AV277485 RIKEN full-length enriched, adult male testis | 1 | 1 | 1 | 0.000037 | 0.000001 |
| A (U74B)2 | 106073_at | 75 | ESTs (UI-M-BH2, 1-apg-h-05-0-UI,s1 NIH_BMAP_M_S3.1) | 1 | 1 | 1 | 0.000017 | 0.000021 |
| A (U74A) | 102209_at | 76 | Nfatc1 (nuclear factor of activated T-cells, cytoplasmic 1) | 1 | 1 | 1 | 0.000034 | 0.000006 |
| A (U74A) | 95795_at | 77 | Sup4h2 gene | 1 | 1 | 1 | 0.000003 | 0.000037 |
| A (U74A) | 99095_at | 78 | Max (Max protein) | 1 | 1 | 1 | 0.00004 | 0 |
| A (U74A) | 102317_at | 79 | Vamp4 (vesicle-associated membrane protein 4) | 1 | 1 | 1 | 0.00001 | 0.00004 |
| A (U74A) | 95064_at | 80 | 0610011L04Rik (RIKEN cDNA 0610011L04 gene) | 1 | 1 | 1 | 0.000043 | 0 |
| A (U74C) | 171517_at | 81 | 2310021H06Rik (RIKEN cDNA 2310021H06 gene) | 1 | 1 | 1 | 0.000023 | 0.000021 |
| A (U74A) | 94005_at | 82 | 3110004018Rik (mitochondrion) | 1 | 1 | 1 | 0.000019 | 0.000027 |
| A (U74A) | 94186_at | 83 | Traf1 (Tnf receptor-associated factor 1) | 1 | 1 | 1 | 0.000037 | 0.000009 |
| A (U74A) | 96951_at | 84 | Atp6m (ATPase, H+ transporting) | 1 | 1 | 1 | 0.000047 | 0.000001 |
| A (U74A) | 97967_at | 85 | 6230425C21Rik (RIKEN cDNA 6230425C21 gene) | 1 | 1 | 1 | 0.000047 | 0.000001 |
| A (U74C) | 165619_r_at | 86 | 810433K01Rik (RIKEN cDNA 2810433K01 gene) | 1 | 1 | 1 | 0.000041 | 0.000008 |
| A (U74A) | 160836_at | 87 | Sema4d (semaphorin M-sema G mRNA) | 1 | 1 | 1 | 0.000027 | 0.000023 |
| A (U74B)2 | 117302_at | 88 | RIKEN full-length enriched library, clone:4932441D06 | 1 | 1 | 1 | 0.00005 | 0.000001 |
| A (U74A) | 93773_f_at | 89 | A1227013 (gene with protein product, function unknown) | 1 | 1 | 1 | 0.000014 | 0.000004 |
| A (U74B)2 | 116418_at | 90 | AW322671 (vw51e12,r1 Soares_mammary_gland_NbMMG) | 1 | 1 | 1 | 0.000043 | 0.000014 |
| A (U74A) | 95705_s_at | 91 | Actx (melanoma X-actin, cytoskeleton) | 1 | 1 | 1 | 0.00004 | 0.000018 |
| A (U74A) | 97844_at | 92 | Rgs2 (regulator of G-protein signaling 2, GTPase activator) | 1 | 1 | 1 | 0 | 0.000059 |
| A (U74A) | 96919_at | 93 | Atp61 (ATPase, H+ transporting) | 1 | 1 | 1 | 0.00005 | 0.000009 |
| A (U74A) | 104298_at | 94 | AI842544 (expressed sequence AI842544) | 1 | 1 | 1 | 0.000001 | 0.000063 |
| A (U74A) | 93117_at | 95 | Hnrpa2b1 (ribonucleoprotein) | 1 | 1 | 1 | 0.000063 | 0.000001 |
| A (U74C) | 168116_f_at | 96 | ESTs, Weakly similar to The Pleckstrin Homology Domain From Grp1 In Complex With Inositol (1,3,4,5,6) pentakisphosphate | 1 | 1 | 1 | 0.000051 | 0.000017 |

Fig. 1B-1

| Analysis Name | Probe Set Name | | Gene Name | Change | Change | Change Status | Change p-value | Change p-value |
|---|---|---|---|---|---|---|---|---|
| A (U74C) | 167915_f_at | 97 | ESTs, Weakly similar to T12449 hypothetical protein | 1 | 1 | 1 | 0.000007 | 0.000063 |
| A (U74C) | 167918_f_at | 98 | Spi8 (serine protease inhibitor 8) | 1 | 1 | 1 | 0.000014 | 0.000063 |
| A (U74A) | 103205_at | 99 | Tcirg1 (T-cell, immune regulator 1) | 1 | 1 | 1 | 0.000003 | 0.000079 |
| A (U74A) | 98441_at | 100 | Fmr1 (fragile X mental retardation syndrome 1 homolog) | 1 | 1 | 1 | 0.000068 | 0.000017 |
| A (U74A) | 104469_at | 101 | Gp38 (glycoprotein 38) | 1 | 1 | 1 | 0.000001 | 0.000085 |
| A (U74A) | 96151_at | 102 | 1110018O12Rik (RIKEN cDNA 1110018O12 gene) | 1 | 1 | 1 | 0.000001 | 0.000085 |
| A (U74A) | 160824_at | 103 | 1110037N09Rik (RIKEN cDNA 1110037N09 gene) | 1 | 1 | 1 | 0.000025 | 0.000063 |
| A (U74C) | 167965_f_at | 104 | AV370033 RIKEN full-length enriched (similar to U36277 Mus musculus I-kappa B alpha chain) | 1 | 1 | 1 | 0.000044 | 0.000044 |
| A (U74A) | 162369_f_at | 105 | Mmp9 (matrix metalloproteinase 9) | 1 | 1 | 1 | 0.000007 | 0.000085 |
| A (U74A) | 104391_s_at | 106 | D17Wsu51e (DNA segment, Chr 17, Wayne State University 51, expressed) | 1 | 1 | 1 | 0.000099 | 0.000001 |
| A (U74A) | 95060_at | 107 | Slc16a7 (solute carrier family 16, integral membrane protein) | 1 | 1 | 1 | 0.000085 | 0.000037 |
| A (U74A) | 97843_at | 108 | Ncoa4 (nuclear receptor coactivator 4) | 1 | 1 | 1 | 0 | 0.000124 |
| A (U74A) | 96709_at | 109 | C79326 (gene with protein product, function known or inferred) | 1 | 1 | 1 | 0.000124 | 0.000001 |
| A (U74C) | 137475_at | 110 | AI481660 (vh27b12, x1 Soares_mammary_gland_NbMMG) | 1 | 1 | 1 | 0.000099 | 0.000029 |
| A (U74A) | 92542_at | 111 | gene with protein product, function unknown | 1 | 1 | 1 | 0.000115 | 0.000029 |
| A (U74A) | 100880_at | 112 | ESTs, Weakly similar to B Chain B | 1 | 1 | 1 | 0.000115 | 0.000031 |
| A (U74C) | 169667_f_at | 113 | Anxa5 (annexin A5) | 1 | 1 | 1 | 0.000085 | 0.000068 |
| A (U74A) | 97502_at | 114 | Dld (dihydrolipoamide dehydrogenase, cytoplasm) | 1 | 1 | 1 | 0.000154 | 0 |
| A (U74A) | 103715_at | 115 | Scin (scinderin) | 1 | 1 | 1 | 0.000154 | 0.000003 |
| A (U74A) | 97887_at | 116 | APOC2 gene, complete CDS, and exons 2 and 3 | 1 | 1 | 1 | 0.0001077 | 0.00005 |
| A (U74A) | 104036_at | 117 | Dpp7 (dipeptidyl peptidase 7) | 1 | 1 | 1 | 0 | 0.000165 |
| A (U74A) | 104671_at | 118 | Ampd3 gene | 1 | 1 | 1 | 0 | 0.000165 |
| A (U74A) | 96278_at | 119 | 1110020C13Rik (RIKEN cDNA 1110020C13) | 1 | 1 | 1 | 0.000165 | 0.000001 |
| A (U74A) | 68533_at | 120 | 0610009N12Rik (RIKEN cDNA 0610009N12 gene) | 1 | 1 | 1 | 0.000165 | 0.000001 |
| A (U74A) | 140664_r_at | 121 | 5716627_RC (ub64f01.x1 Soares_mammary_gland_NMLMG) | 1 | 1 | 1 | 0.000165 | 0.000004 |
| A (U74C) | 166247_at | 122 | ESTs, Moderately similar to T00380 K1AA0637 protein | 1 | 1 | 1 | 0.000107 | 0.000068 |
| A (U74A) | 160199_at | 123 | Hnrpc (heterogeneous nuclear ribonucleoprotein C) | 1 | 1 | 1 | 0.000177 | 0 |
| A (U74C) | 104602_at | 124 | D2Ertd120e (DNA segment, Chr 2, ERATO Doi 120, expressed) | 1 | 1 | 1 | 0.000001 | 0.000177 |
| A (U74C) | 136537_at | 125 | ESTs (vi99f07.x1 Barstead mouse pooled organs MPLRB4) | 1 | 1 | 1 | 0.000063 | 0.000115 |
| A (U74B)2 | 110980_at | 126 | ESTs (UI-M-B1H-ako-e-10-0-UI.s1 NIH_BMAP_M_S2) | 1 | 1 | 1 | 0.000003 | 0.000177 |
| A (U74A) | 96060_at | 127 | Serpinb6 (serine protease inhibitor) | 1 | 1 | 1 | 0 | 0.000191 |
| A (U74A) | 102249_at | 128 | advillin | 1 | 1 | 1 | 0.000008 | 0.000191 |

Fig. 1B-2

| Analysis Name | Probe Set Name | | Gene Name | Change | Change | Change | Status | Change p-value | Change p-value |
|---|---|---|---|---|---|---|---|---|---|
| A (U74B)2 | 116400_at | 129 | 4632415D10Rik (RIKEN cDNA 4632415D10 gene) | 1 | 1 | 1 | 1 | 0.000063 | 0.000165 |
| A (U74A) | 104589_at | 130 | Rmp-pending (RPB5-mediating protein) | 1 | 1 | 1 | 1 | 0.000191 | 0.000054 |
| A (U74A) | 160979_at | 131 | ESTs (UI-M-BH2,3-aoa-c-03-0-UI, sl NIH_BMAP_M_S3, 3) | 1 | 1 | 1 | 1 | 0.000236 | 0.000009 |
| A (U74B)2 | 163364_at | 132 | 5730496F10Rik (RIKEN cDNA 5730496F10 gene) | 1 | 1 | 1 | 1 | 0.00004 | 0.000205 |
| A (U74B)2 | 162927_at | 133 | transmembrane protein Bet, complete cds | 1 | 1 | 1 | 1 | 0.000243 | 0.000007 |
| A (U74A) | 95058_f_at | 134 | 2610205H19Rik (RIKEN cDNA 2610205H19) | 1 | 1 | 1 | 1 | 0.000253 | 0 |
| A (U74B)2 | 106302_at | 135 | ETSs, Weakly similar to All-1 protein +GTE form | 1 | 1 | 1 | 1 | 0.000063 | 0.00022 |
| A (U74C) | 170331_i_at | 136 | ESTs, AV043202 Mus musculus adult C57BL/6J testis | 1 | 1 | 1 | 1 | 0.000023 | 0.0002273 |
| A (U74A) | 104268_at | 137 | interleukin-6 (IL-6) receptor | 1 | 1 | 1 | 1 | 0.00005 | 0.000253 |
| A (U74A) | 94433_at | 138 | AI316867 (expressed sequence AI316867) | 1 | 1 | 1 | 1 | 0.000311 | 0 |
| A (U74A) | 99678_f_at | 139 | Atp51 (ATP synthase, H+ transporting, mitochondrial F0 complex) | 1 | 1 | 1 | 1 | 0.000092 | 0.00022 |
| A (U74A) | 102000_f_at | 140 | 1500004006Rik (RIKEN cDNA 1500004006 gene) | 1 | 1 | 1 | 1 | 0.000311 | 0.000001 |
| A (U74A) | 161969_f_at | 141 | Capg (capping protein (actin filament), gelsolin-like) | 1 | 1 | 1 | 1 | 0.000003 | 0.000311 |
| A (U74A) | 103471_at | 142 | 4432405K22Rik (RIKEN cDNA 4432405K22 gene) | 1 | 1 | 1 | 1 | 0.000027 | 0.00029 |
| A (U74C) | 136663_at | 143 | ESTs, UI-M-AO1-ael-c-05-0-UI.sl NIH_BMAP_MPG_N | 1 | 1 | 1 | 1 | 0.00022 | 0.000099 |
| A (U74A) | 162094_f_at | 144 | Wilms' tumour 1-associating protein | 1 | 1 | 1 | 1 | 0.000236 | 0.000085 |
| A (U74A) | 97919_at | 145 | 1110021E09Rik (RIKEN cDNA 1110021E09 gene) | 1 | 1 | 1 | 1 | 0.000311 | 0.000011 |
| A (U74A) | 101995_at | 146 | Sqstm1 (sequestosome 1, transcription co-factor) | 1 | 1 | 1 | 1 | 0.000333 | 0 |
| A (U74A) | 108493_at | 147 | 4632462J16Rik (RIKEN cDNA 4632432J16 gene) | 1 | 1 | 1 | 1 | 0.000236 | 0.000099 |
| A (U74B)2 | 95288_i_at | 148 | AI848106 (expressed sequence AI848406) | 1 | 1 | 1 | 1 | 0.000332 | 0.000003 |
| A (U74A) | 112857_g_at | 149 | 4930404N11Rik (RIKEN cDNA 4930404N11 gene) | 1 | 1 | 1 | 1 | 0.000253 | 0.000085 |
| A (U74C) | 168210_r_at | 150 | ESTs, Weakly similar to vacuolar ATP synthase subunit D | 1 | 1 | 1 | 1 | 0.000006 | 0.000333 |
| A (U74C) | 166304_f_at | 151 | 5730403E06Rik (RIKEN cDNA 5730403E06 gene) | 1 | 1 | 1 | 1 | 0.000333 | 0.000007 |
| A (U74A) | 100479_at | 152 | Dnmt3a (DNA methyltransferase 3A) | 1 | 1 | 1 | 1 | 0.000011 | 0.000011 |
| A (U74A) | 161756_at | 153 | 4833420N02Rik (RIKEN cDNA 4833420N02 gene) | 1 | 1 | 1 | 1 | 0.000333 | 0.000115 |
| A (U74A) | 104308_at | 154 | Itgax (integrin alpha X) | 1 | 1 | 1 | 1 | 0.00029 | 0 |
| A (U74A) | 96281_at | 155 | Atp6gl (ATPase, H+ transporting) | 1 | 1 | 1 | 1 | 0.000408 | 0 |
| A (U74A) | 98473_at | 156 | Arg2 (arginase type II) | 1 | 1 | 1 | 1 | 0.000408 | 0.000382 |
| A (U74A) | 161754_f_at | 157 | Glb1 (galactosidase, beta 1) | 1 | 1 | 1 | 1 | 0.000029 | 0.000408 |
| A (U74A) | 160399_r_at | 158 | H2afy (H2A histone family, member Y) | 1 | 1 | 1 | 1 | 0.000013 | 0.000408 |
| A (U74B)2 | 106617_at | 159 | AW123240 (expressed sequence AW123240) | 1 | 1 | 1 | 1 | 0.000014 | 0.000001 |
| A (U74A) | 94774_at | 160 | Ifi202a (interferon activated gene 202A) | 1 | 1 | 1 | 1 | 0.000437 | 0.000001 |
| A (U74A) | 98981_s_at | 161 | Tcf12 (transcription factor 12) | 1 | 1 | 1 | 1 | 0.000068 | 0.000382 |

Fig. 1C-1

| Analysis Name | Probe Set Name | | Gene Name | Change | Change | Status | Change p-value | Change p-value |
|---|---|---|---|---|---|---|---|---|
| A (U74A) | 92598_at | 162 | Atp6b2 (hydrogen-transporting) | 1 | 1 | 1 | 0.000467 | 0.000001 |
| A (U74A) | 92480_f_at | 163 | Zfp118 (Zinc finger protein 118) | 1 | 1 | 1 | 0.000467 | 0.000009 |
| A (U74A) | 94939_at | 164 | Cd53 (CD53 antigen) | 1 | 1 | 1 | 0.000467 | 0.000012 |
| A (U74A) | 160141_r_at | 165 | 5730507C05Rik (RIKEN cDNA 5730507C05 gene) | 1 | 1 | 1 | 0.000079 | 0.000408 |
| A (U74A) | 92492_at | 166 | adenylate kinase 3 alpha like | 1 | 1 | 1 | 0.000107 | 0.000382 |
| A (U74A) | 102644_at | 167 | Mus musculus (C57BL/10 X C3H)F2 clone 1.5 nivel mRNA from renin-expressing kidney tumor cell line | 1 | 1 | 1 | 0.000533 | 0.000002 |
| A (U74B)2 | 114270_at | 168 | ESTs, UI-M-BH1-ami-b-10-0-UI.sl | 1 | 1 | 1 | 0.000011 | 0.000533 |
| A (U74C) | 166804_f_at | 169 | AV105500 Mus musculus liver C57BL/6J 13-day embryo | 1 | 1 | 1 | 0.000001 | 0.000557 |
| A (U74C) | 166076_r_at | 170 | 2500001K11Rik (RIKEN cDNA 2500001K11 gene) | 1 | 1 | 1 | 0.00057 | 0.000001 |
| A (U74B)2 | 114238_at | 171 | AI426953 (mn07e09,y1 Beddington mouse embryonic region) | 1 | 1 | 1 | 0.000533 | 0.00005 |
| A (U74A) | 92660_f_at | 172 | Ube2el (ubiquitin-conjugating enzyme E2E 1) | 1 | 1 | 1 | 0.00057 | 0.000019 |
| A (U74A) | 160397_at | 173 | Mus musculus, Similar to 1K cytokine, down-regulator of HLA 11, clone WGC:25508 IMAGE:490184, mRNA | 1 | 1 | 1 | 0.000001 | 0.000608 |
| A (U74A) | 98468_r_at | 174 | AI316859 (expressed sequence AI316859) | 1 | 1 | 1 | 0.000533 | 0.000085 |
| A (U74A) | 92356_at | 175 | Ptpn8 (protein tyrosine phosphatase, non-receptor type 8) | 1 | 1 | 1 | 0.000649 | 0 |
| A (U74C) | 166673_at | 176 | AV319021 RIKEN full-length enriched, 13 days embryo male testis | 1 | 1 | 1 | 0.000001 | 0.000649 |
| A (U74A) | 93970_at | 177 | 5730403B10Rik (gene with protein product, function unknown) | 1 | 1 | 1 | 0.000649 | 0.000001 |
| A (U74C) | 140759_at | 178 | ESTs, Moderately similar to T43486 hypothetical protein DKFZp434N1272.1 | 1 | 1 | 1 | 0.000649 | 0.000004 |
| A (U74A) | 95070_at | 179 | Nars (asparaginyl-tRNA synthetase) | 1 | 1 | 1 | 0.00057 | 0.000092 |
| A (U74C) | 168018_at | 180 | hypothetical protein, MGC:7041 | 1 | 1 | 1 | 0.000133 | 0.000533 |
| A (U74A) | 94476_at | 181 | AA672926 (RIKEN cDNA 4930553M18) | 1 | 1 | 1 | 0.000467 | 0.000205 |
| A (U74A) | 92847_s_at | 182 | M6pr (integral membrane protein) | 1 | 1 | 1 | 0.00022 | 0.000467 |
| A (U74A) | 102222_at | 183 | Utx (ubiquitously transcribed tetratricopeptide repeat gene) | 1 | 1 | 1 | 0.000085 | 0.000608 |
| A (U74A) | 104314_r_at | 184 | 1110032A03Rik (RIKEN cDNA 1110032A03 gene) | 1 | 1 | 1 | 0.000693 | 0.000037 |
| A (U74A) | 102940_at | 185 | Ltb (lymphotoxin B) | 1 | 1 | 1 | 0.000739 | 0 |
| A (U74A) | 99051_at | 186 | mtsl protein gene, exon 2 | 1 | 1 | 1 | 0.000001 | 0.000739 |
| A (U74C) | 171593_at | 187 | Cox5a (cytochrome c oxidase, subunit Va) | 1 | 1 | 1 | 0.000467 | 0.00029 |
| A (U74A) | 100905_at | 188 | 4921531D01Rik (RIKEN cDNA 4921531D01 gene) | 1 | 1 | 1 | 0 | 0.000789 |
| A (U74A) | 103443_at | 189 | Aiml (absent in melanoma 1) | 1 | 1 | 1 | 0 | 0.000789 |
| A (U74A) | 102211_r_at | 190 | A1605202 (expressed sequence A1605202) | 1 | 1 | 1 | 0.00057 | 0.000253 |
| A (U74A) | 161912_r_at | 191 | Numb (numb gene homolog (Drosophila )) | 1 | 1 | 1 | 0.000581 | 0.000258 |
| A (U74A) | 103222_at | 192 | Eps8 (epidermal growth factor receptor pathway substrate 8) | 1 | 1 | 1 | 0 | 0.000841 |
| A (U74A) | 96752_at | 193 | intercellular adhesion molecule 1 (ICAM-1) gene, exons 6 and 7 | 1 | 1 | 1 | 0.000001 | 0.000841 |

Fig. 1C-2

| Analysis Name | Probe Set Name | | Gene Name | Change | Change | Status | Change p-value | Change p-value |
|---|---|---|---|---|---|---|---|---|
| A (U74A) | 102060_at | 194 | Golga4 (golgi autoantigen, golgin subfamily a, 4) | 1 | 1 | 1 | 0.000739 | 0.000115 |
| A (U74B)2 | 110269_at | 195 | 2310032J20Rik (RIKEN cDNA 2310032J20 gene) | 1 | 1 | 1 | 0.000205 | 0.000649 |
| A (U74A) | 92582_at | 196 | Slc1a7 (membrane) | 1 | 1 | 1 | 0.000649 | 0.00022 |
| A (U74A) | 93994_at | 197 | Mus musculus 10 day old male pancreas cDNA | 1 | 1 | 1 | 0.000739 | 0.000177 |
| A (U74A) | 102384_at | 198 | 2610209L14Rik (RIKEN cDNA 2610209L14 gene) | 1 | 1 | 1 | 0.000437 | 0.000499 |
| A (U74C) | 168478_s_at | 199 | 5730496F10Rik (RIKEN cDNA 5730496F10 gene) | 1 | 1 | 1 | 0.000608 | 0.000333 |
| A (U74A) | 93038_f_at | 200 | lipocortin 1 gene, exon 13 | 1 | 1 | 1 | 0.000955 | 0 |
| A (U74A) | 102872_f_at | 201 | Zfp51 (zinc finger protein 51) | 1 | 1 | 1 | 0.000789 | 0.000177 |
| A (U74A) | 161617_f_at | 202 | 2410001E19Rik (RIKEN cDNA 2410001E19 gene) | 1 | 1 | 1 | 0.000611 | 0.000376 |
| A (U74A) | 95784_at | 203 | Pira1 (paired-Ig-like receptor A1) | 1 | 1 | 1 | 0.000001 | 0.001017 |
| A (U74C) | 130186_f_at | 204 | Tcirg1 (T-cell, immune regulator 1) | 1 | 1 | 1 | 0.000004 | 0.001017 |
| A (U74A) | 97914_at | 205 | mitochondrial stress-70 protein (PBP74/CSA), exon 14, 15, 16 and 17 | 1 | 1 | 1 | 0.000143 | 0.000896 |
| A (U74A) | 96790_f_at | 206 | AU015645 (expressed sequence AU015645) | 1 | 1 | 1 | 0.000236 | 0.000841 |
| A (U74A) | 96696_at | 207 | UI-M-AK0-adc-e-02-0-UI.s1 | 1 | 1 | 1 | 0.001082 | 0.000002 |
| A (U74A) | 96013_r_at | 208 | Matr3 (martin 3) | 1 | 1 | 1 | 0.001082 | 0.000009 |
| A (U74A) | 97710_f_at | 209 | Mpv17 (Mpv17 transgene, kidney disease mutant-like) | 1 | 1 | 1 | 0.000789 | 0.000311 |
| A (U74B)2 | 109355_at | 210 | ESTs, Weakly similar to T00039 hypothetical protein KIAA0290 | 1 | 1 | 1 | 0.00057 | 0.000533 |
| A (U74A) | 95010_at | 211 | Traf3 (Tnf receptor-associated factor 3) | 1 | 1 | 1 | 0.00057 | 0.000533 |
| A (U74A) | 98767_at | 212 | Yy1 (YY1 transcription factor) | 1 | 1 | 1 | 0.001082 | 0.000004 |
| A (U74C) | 167634_i_at | 213 | ESTs, AV247190 RIKEN full-length enriched, 0 day neonate head | 1 | 1 | 1 | 0.001117 | 0.000009 |
| A (U74A) | 93445_at | 214 | Api6 (apoptosis inhibitory 6) | 1 | 1 | 1 | 0.000005 | 0.001152 |
| A (U74A) | 160949_at | 215 | Parg (poly (ADP-ribose) glycohydrolase) | 1 | 1 | 1 | 0.001152 | 0.000029 |
| A (U74A) | 161696_f_at | 216 | C77080 (expressed sequence C77080) | 1 | 1 | 1 | 0.001152 | 0.000074 |
| A (U74B)2 | 113740_at | 217 | AI225872 (vx57d10.r1 Stratagene mouse macrophage (#937306)) | 1 | 1 | 1 | 0.001226 | 0.000031 |
| A (U74C) | 171048_i_at | 218 | AV338811 RIKEN full-length enriched, adult male olfactory bulb | 1 | 1 | 1 | 0.000419 | 0.000854 |
| A (U74A) | 162463_at | 219 | Tpd52 (tumor protein D52) | 1 | 1 | 1 | 0.000896 | 0.000382 |
| A (U74A) | 93907_f_at | 220 | MIA14 full-length intracisternal A-particle gag protein gene | 1 | 1 | 1 | 0.000133 | 0.001152 |
| A (U74A) | 165724_at | 221 | 4930438D12Rik RIKEN cDNA 4930438D12 gene) | 1 | 1 | 1 | 0.001304 | 0.000002 |
| A (U74A) | 104621_at | 222 | ESTs, Highly similar to T00268 hypothetical protein KIAA0597 [H. sapiens] | 1 | 1 | 1 | 0.001226 | 0.000133 |
| A (U74A) | 97853_at | 223 | AA408851 (gene with protein product, function unknown) | 1 | 1 | 1 | 0.001226 | 0.000133 |
| A (U74C) | 166852_at | 224 | AI851877 (UI-M-BH0-aix-a-11-0-UI.s1 NIH_BMAP_M_SI) | 1 | 1 | 1 | 0.000419 | 0.000854 |
| A (U74A) | 160103_at | 225 | Axot (axotrophin) | 1 | 1 | 1 | 0.000043 | 0.001387 |
| A (U74A) | 160156_at | 226 | vx55cil.r1 Stratagene mouse macrophage | 1 | 1 | 1 | 0.001387 | 0.001474 |

Fig. 1D-1

| Analysis Name | Probe Set Name | | Gene Name | Change | Change | Status | Change p-value | Change p-value |
|---|---|---|---|---|---|---|---|---|
| A (U74A) | 96900_at | 227 | Als2 (amyotrophic lateral sclerosis 2) | 1 | 1 | 1 | 0.001474 | 0.000001 |
| A (U74A) | 92191_at | 228 | 2810410A08Rik (RIKEN cDNA 2810410A08 gene) | 1 | 1 | 1 | 0.001474 | 0.000006 |
| A (U74A) | 160697_at | 229 | C77080 (expressed sequence C77080) | 1 | 1 | 1 | 0.001474 | 0.00004 |
| A (U74A) | 161695_f_at | 230 | Slc6a4 (solute carrier family 6 (neurotransmitter transporter, serotonin), member 4) | 1 | 1 | 1 | 0.000467 | 0.001082 |
| A (U74A) | 100570_at | 231 | Nyren18-pending (NY-REN-18 antigen) | 1 | 1 | 1 | 0.000085 | 0.001474 |
| A (U74A) | 92638_at | 232 | Ppp2ca (protein serine/threonine phosphatase) | 1 | 1 | 1 | 0.001474 | 0.000085 |
| A (U74A) | 99143_at | 233 | Tgoln2 (trans-golgi network protein 2) | 1 | 1 | 1 | 0.001566 | 0.000003 |
| A (U74A) | 102002_at | 234 | Ubqln2 (ubiquilin 2) | 1 | 1 | 1 | 0.000004 | 0.001566 |
| A (U74A) | 161244_f_at | 235 | Pstpip1 (proline-serine-threonine phosphatase-interacting protein 1) | 1 | 1 | 1 | 0.000789 | 0.000789 |
| A (U74A) | 103235_at | 236 | 0710005A05Rik (RIKEN cDNA 0710005A05 gene) | 1 | 1 | 1 | 0.000205 | 0.001387 |
| A (U74A) | 97395_at | 237 | D19Wsu5e (DNA segment, Chr 19, Wayne State University 55, expressed) | 1 | 1 | 1 | 0.001566 | 0.000029 |
| A (U74A) | 101004_f_at | 238 | Srp20 gene | 1 | 1 | 1 | 0.001474 | 0.000165 |
| A (U74A) | 98112_r_at | 239 | 2140015L10Rik (leucine aminopeptidase) | 1 | 1 | 1 | 0.000271 | 0.001387 |
| A (U74A) | 103444_at | 240 | ESTs, Weakly similar to SMB2 MOUSE DNA-BINDING PROTEIN SMUBP-2 | 1 | 1 | 1 | 0.000001 | 0.001664 |
| A (U74A) | 103312_f_at | 241 | C79684 (expressed sequence C79684) | 1 | 1 | 1 | 0.000012 | 0.001664 |
| A (U74A) | 97947_at | 242 | 1700031C13Rik (RIKEN cDNA 1700031C13 gene) | 1 | 1 | 1 | 0.000333 | 0.001387 |
| A (U74A) | 100561_at | 243 | IQ motif containing GTPase activating protein 1 | 1 | 1 | 1 | 0.000437 | 0.001304 |
| A (U74A) | 168016_r_at | 244 | 6030404E16Rik (RIKEN cDNA 6030404E16 gene) | 1 | 1 | 1 | 0.000739 | 0.001017 |
| A (U74A) | 94806_at | 245 | Pdhb (pyruvate dehydrogenase (lipoamide) beta) | 1 | 1 | 1 | 0.001664 | 0.000115 |
| A (U74A) | 955533_at | 246 | Zfp106 (zinc finger protein 106) | 1 | 1 | 1 | 0.000124 | 0.001664 |
| A (U74A) | 160263_r_at | 247 | 0710001O20Rik (RIKEN cDNA 0710001O20 gene) | 1 | 1 | 1 | 0.00004 | 0.001767 |
| A (U74A) | 101502_at | 248 | Tgif (TG interacting factor, transcription factor) | 1 | 1 | 1 | 0.001876 | 0 |
| A (U74A) | 99856_r_at | 249 | Ctnnd2 (catenin (cadherin-associated protein), delta 2) | 1 | 1 | 1 | 0.001543 | 0.000333 |
| A (U74A) | 102124_f_at | 250 | Cox4a (cytochrome c oxidase, subunit IVa) | 1 | 1 | 1 | 0.001304 | 0.000608 |
| A (U74B)2 | 112926_at | 251 | hypothetical protein, MGC:7036 | 1 | 1 | 1 | 0.000047 | 0.001876 |
| A (U74B)2 | 108058_at | 252 | 2810441M03Rik (RIKEN cDNA 2810441M03 gene) | 1 | 1 | 1 | 0.001664 | 0.00029 |
| A (U74C) | 161127_i_at | 253 | ESTs, Weakly similar to RL24_HUMAN 60S RIBOSOMAL PROTEIN | 1 | 1 | 1 | 0.000905 | 0.001056 |
| A (U74A) | 167468_at | 254 | AW11752 (expressed sequence AW011752) | 1 | 1 | 1 | 0.001876 | 0.000107 |
| A (U74B)2 | 111877_at | 255 | ESTs, Highly similar to T41751 1-afadin - rat | 1 | 1 | 1 | 0.000003 | 0.001991 |
| A (U74A) | 103563_at | 256 | 4930534K13Rik (RIKEN cDNA 4930534K13 gene) | 1 | 1 | 1 | 0.001991 | 0.000003 |
| A (U74A) | 96724_r_at | 257 | R75011 (expressed sequence R75011) | 1 | 1 | 1 | 0.000467 | 0.001566 |
| A (U74B)2 | 116599_at | 258 | ESTs vo59b04, rl Soares_mammary_gland_NbMMG | 1 | 1 | 1 | 0.001017 | 0.001017 |

Fig. 1D-2

| Analysis Name | Probe Set Name | | Gene Name | Change | Change | Status | Change p-value | Change p-value |
|---|---|---|---|---|---|---|---|---|
| A (U74A) | 93964_s_at | 259 | Mus musculus putative RNA helicase RCK mRNA | | | | | 0.001991 0.000043 |
| A (U74A) | 102205_at | 260 | Mafb (v-maf musculoaponeurotic fibrosarcoma oncogene family, protein B (avian)) | 1 | 1 | 0.000311 | 0.001767 |
| A (U74A) | 93491_f_at | 261 | 1100001F19Rik (gene with protein product, function unknown) | 1 | 1 | 0.000001 | 0.002112 |
| A (U74A) | 102425_at | 262 | Tle1 (transducin-like enhancer of split 1, homolog of Drosophila E(spl)) | 1 | 1 | 0.001991 | 0.000154 |
| A (U74A) | 94832_at | 263 | Ags, L44L, and Btk genes | 1 | 1 | 0.000063 | 0.002112 |
| A (U74A) | 101684_r_at | 264 | Srst (simple repeat sequence-containing transcript) | 1 | 1 | 0.000074 | 0.002112 |
| A (U74A) | 99823_r_at | 265 | D18Ertd232e (DNA segment, Chr 18, ERATO Doi 232) | 1 | 1 | 0.001304 | 0.000896 |
| A (U74A) | 94076_i_at | 266 | Rpn2 (ribophorin II) | 1 | 1 | 0.000007 | 0.002195 |
| A (U74B)2 | 114812_at | 267 | Pmaip1 (phorbol-12-myristate-13-acetate-induced protein 1) | 1 | 1 | 0.000003 | 0.00224 |
| A (U74A) | 99522_at | 268 | Gsg2 (germ cell-specific gene 2) | 1 | 1 | 0.000019 | 0.00224 |
| A (U74A) | 104612_g_at | 269 | C77982 (expressed sequence C77982) | 1 | 1 | 0.000896 | 0.001474 |
| A (U74A) | 160947_at | 270 | AI851258 (expressed sequence AI851258) | 1 | 1 | 0.002375 | 0.000034 |
| A (U74B)2 | 162618_at | 271 | AI785475 (uj42f11.x1 Sugano mouse liver m1ia) | 1 | 1 | 0.001152 | 0.001304 |
| A (U74A) | 92338_f_at | 272 | Mus musculus cDNA clone IMAGE:2136264 3' | 1 | 1 | 0.000467 | 0.001991 |
| A (U74A) | 166692_at | 273 | AI450803 (expressed sequence AI450803) | 1 | 1 | 0.000896 | 0.001566 |
| A (U74A) | 166999_at | 274 | ESTs, AV152718 Mus musculus hippocampus C57BL/6J | 1 | 1 | 0.001991 | 0.000499 |
| A (U74A) | 96695_at | 275 | Ube2a (ubiquitin-conjugating enzyme E2A) | 1 | 1 | 0.001991 | 0.000499 |
| A (U74C) | 167626_r_at | 276 | ESTs, Weakly similar to T22586 hypothetical protein F53F4. 14 - Caenorhabditis elegans | 1 | 1 | 0.001248 | 0.001248 |
| A (U74C) | 168057_f_at | 277 | ESTs, Weakly similar to T00268 hypothetical protein KIAA0597 | 1 | 1 | 0.001767 | 0.000739 |
| A (U74A) | 94043_at | 278 | Atp6s1 (integral membrane protein) | 1 | 1 | 0.002112 | 0.000499 |
| A (U74B)2 | 111381_r_at | 279 | AV216087 (vn21e07.rl Knowles Solter mouse blastocyst B1) | 1 | 1 | 0.00057 | 0.00224 |
| A (U74A) | 160442_at | 280 | Cctb gene for chaperonin containing TCP-1 beta subunit | 1 | 1 | 0.001664 | 0.001226 |
| A (U74C) | 169904_r_at | 281 | Ebaf (endometrial bleeding associated factor) | 1 | 1 | 0.001304 | 0.001664 |
| A (U74A) | 102017_at | 282 | Prpk (pre-mRNA protein kinase) | 1 | 1 | 0.00224 | 0.001017 |
| A (U74A) | 161377_at | 283 | Emr1 (EGF-like module containing, mucin-like, hormone receptor-like sequence 1) | 1 | 1 | 0.001876 | 0.001387 |
| A (U74C) | 168277_r_at | 284 | D14Ertd226e, AV232952 RIKEN full-length enriched, 0 day neonate skin | 1 | 1 | 0.001664 | 0.001991 |
| A (U74A) | 104489_at | 285 | Sntb2 (syntrophin, basic 2) | 1 | 1 | 0.001474 | 0.00224 |

Fig. 1E

| Analysis Name | Probe Set Name | | Gene Name | Change | Change | Status | Change p-value | Change p-value |
|---|---|---|---|---|---|---|---|---|
| A (U74A) | 99521_at | 286 | Ak4 (adenylate kinase 4) | 0 | 0 | 0 | 0.998009 | 0.998336 |
| A (U74B)2 | 115760_at | 287 | Mus musculus, clone MGC:11687 IMAGE:3961992, mRNA, complete cds | 0 | 0 | 0 | 0.99776 | 0.999307 |
| A (U74B)2 | 112703_at | 288 | ESTs, UI-M-AQl-aef-f-04-0-UI.sl NIH_BMAP_MHI_N | 0 | 0 | 0 | 0.999211 | 0.998233 |
| A (U74B)2 | 112889_at | 289 | AB041662 (hypothetical protein, MNCb-4193) | 0 | 0 | 0 | 0.998009 | 0.999533 |
| A (U74B)2 | 112988_at | 290 | ESTs, Weakly similar to ATIB MOUSE POTENTIAL PHOSPHOLIPID-TRANSPORTING ATPASE IB | 0 | 0 | 0 | 0.999998 | 0.997625 |
| A (U74C) | 137034_f_at | 291 | 5712828_RC, ve47g08.x1 Beddington mouse embryonic | 0 | 0 | 0 | 0.999999 | 0.997626 |
| A (U74C) | 133928_at | 292 | ESTs, vk39a06.x1 Soares_mammary_gland_NbNNG | 0 | 0 | 0 | 0.999941 | 0.99776 |
| A (U74B)2 | 164216_at | 293 | Erol (EROI-like (S. cerevisiae)) | 0 | 0 | 0 | 0.998009 | 0.99971 |
| A (U74B)2 | 113182_at | 294 | D1Ertd101e (DNA segment, Chr 1, ERATO Doi 101, expressed) | 0 | 0 | 0 | 0.998124 | 0.999689 |
| A (U74B)2 | 112401_at | 295 | AU022421 (ua72h12.r1 Soares_thymus_2NbMT) | 0 | 0 | 0 | 0.998613 | 0.999211 |
| A (U74A) | 101956_at | 296 | ESTs, Weakly similar to S21801 myosin heavy chain | 0 | 0 | 0 | 0.999946 | 0.997888 |
| A (U74A) | 98918_at | 297 | D13Wsu115e (bone morphogenetic protein 6) | 0 | 0 | 0 | 0.999915 | 0.998009 |
| A (U74C) | 93548_at | 298 | AW122942 (gene with protein product, function unknown) | 0 | 0 | 0 | 0.998009 | 0.999926 |
| A (U74C) | AFFX-MURINE_bl | 299 | Mus musculus C57/Black6 BC1 scRNA | 0 | 0 | 0 | 0.998735 | 0.999269 |
| A (U74A) | 95468_at | 300 | Egln1 (EGL nine homolog 1) | 0 | 0 | 0 | 0.998124 | 0.999999 |
| A (U74B)2 | 115354_at | 301 | AU045240 (RIKEN cDNA 1110054A24 gene) | 0 | 0 | 0 | 0.998124 | 0.999987 |
| A (U74A) | 95722_at | 302 | Glrx1 (glutaredoxin 1, glutaredoxin) | 0 | 0 | 0 | 0.998233 | 0.999941 |
| A (U74A) | 95456_r_at | 303 | Shfdg1 (split hand/foot deleted gene 1) | 0 | 0 | 0 | 0.998526 | 0.999946 |
| A (U74A) | 95643_at | 304 | Wdr6 (WD repeat domain 6) | 0 | 0 | 0 | 0.998526 | 0.99996 |
| A (U74C) | 135189_f_at | 305 | AI413331 (expressed sequrnce AI413331) | 0 | 0 | 0 | 1 | 0.998526 |
| A (U74A) | 99566_at | 306 | triosephosphate isomerase (tpi) gene | 0 | 0 | 0 | 0.998613 | 0.999971 |
| A (U74B)2 | 112767_s_at | 307 | Utrn (utrophin) | 0 | 0 | 0 | 0.999991 | 0.998774 |
| A (U74B)2 | 115920_at | 308 | EST C78892 | 0 | 0 | 0 | 0.998774 | 0.999997 |
| A (U74A) | AFFX-MURINE_bl | 309 | Mus musculus C57/Black6 BC1 scRNA | 0 | 0 | 0 | 0.999958 | 0.998835 |
| A (U74A) | 94322_at | 310 | Sqle (squalene epoxidase, integral membrane protein) | 0 | 0 | 0 | 1 | 0.998848 |
| A (U74A) | 95636_at | 311 | 1110020A23Rik (RIKEN cDNA 1110020A23 gene) | 0 | 0 | 0 | 0.999689 | 0.999211 |
| A (U74A) | 93602_at | 312 | Rps6ka4 (ribosomal protein S6 kinase) | 0 | 0 | 0 | 0.999501 | 0.999533 |
| A (U74B)2 | 107005_at | 313 | D1Ertd101e (DNA segment, Chr 1, ERATO Doi 101, expressed) | 0 | 0 | 0 | 0.999392 | 0.999667 |
| A (U74A) | 93264_at | 314 | Srebf1 (sterol regulatory element binding factor 1, integral membrane protein) | 0 | 0 | 0 | 0.999159 | 1 |
| A (U74B) 2 | 108095_at | 315 | Egln1 (EGL nine homolog 1) | 0 | 0 | 0 | 0.999211 | 0.999999 |
| A (U74B)2 | 112977-at | 316 | ESTs, UI-M-BHl-anb-a-03-0-UI, sl NIH_BMAP_M_S2 | 0 | 0 | 0 | 0.999987 | 0.999261 |
| A (U74A) | 160862_at | 317 | Ptp4a3 (protein tyrosine phosphatase 4a3) | 0 | 0 | 0 | 0.999261 | 0.999997 |

Fig. 2A-1

| Analysis Name | Probe Set Name | | Gene Name | Change | Change | Change Status | Change p-value | Change p-value |
|---|---|---|---|---|---|---|---|---|
| A (U74A) | 101930_at | 318 | Nfix (nuclear factor I/X) | 0 | 0 | 0 | 0.999999 | 0.999261 |
| A (U74A) | 95758_at | 319 | Scd2 (stearoyl-Coenzyme A desaturase 2, integral membrane protein) | 0 | 0 | 0 | 0.999999 | 0.999261 |
| A (U74B)2 | 109390_at | 320 | Siat10 (sialyltransferase 10 (alpha-2,3-sialyltransferase VI) | 0 | 0 | 0 | 0.999392 | 0.999908 |
| A (U74B)2 | 115756_at | 321 | Fgd2 (faciogenital dysplasia homolog 2 (human)) | 0 | 0 | 0 | 0.999941 | 0.999392 |
| A (U74B)2 | 107435_at | 322 | BB104748 (expressed sequence BB104748) | 0 | 0 | 0 | 0.99943 | 0.99996 |
| A (U74B)2 | 115556_s_at | 323 | AI552584 (expressed sequence AI552584) | 0 | 0 | 0 | 0.99943 | 0.999998 |
| A (U74B)2 | 111380_at | 324 | 1110011E12Rik (RIKEN cDNA 1110011E12 gene) | 0 | 0 | 0 | 0.999973 | 0.999592 |
| A (U74A) | 95674_r_at | 325 | 2610024P12Rik (RIKEN cDNA 2610024P12 gene) | 0 | 0 | 0 | 0.999893 | 0.999689 |
| A (U74A) | 160065_s_at | 326 | Csrp (cysteine rich protein) | 0 | 0 | 0 | 0.999954 | 0.999729 |
| A (U74A) | 102208_at | 327 | Siat10 (sialyltransferase 10) | 0 | 0 | 0 | 0.999977 | 0.999747 |
| A (U74A) | 96008_at | 328 | Defender against Apoptotic Death (Dad1) gene, exon 3 | 0 | 0 | 0 | 0.99995 | 0.999795 |
| A (U74A) | 98129_at | 329 | Tmsb10 (thymosin, beta 10) | 0 | 0 | 0 | 0.999795 | 0.999998 |
| A (U74B)2 | 108614_f_at | 330 | 1110012005Rik (RIKEN cDNA 1110012005 gene) | 0 | 0 | 0 | 0.999926 | 0.999876 |
| A (U74A) | 160568_at | 331 | Eno1 (enolase 1, alpha non-neuron) | 0 | 0 | 0 | 0.999908 | 0.999901 |
| A (U74C) | 166122_at | 332 | 4930583H14Rik (RIKEN cDNA 4930583H14 gene) | 0 | 0 | 0 | 0.999952 | 0.999885 |
| A (U74B)2 | 105752_f_at | 333 | Gcn512 (general control of amino acid synthesis-like 2 (yeast)) | 0 | 0 | 0 | 0.999885 | 0.999997 |
| A (U74A) | 96359_at | 334 | D1Ertd101e (DNA segment) | 0 | 0 | 0 | 0.999969 | 0.999932 |
| A (U74A) | 92232-at | 335 | Cish3 (cytokine inducible SH2-containing protein 3) | 0 | 0 | 0 | 1 | 0.999908 |
| A (U74C) | 165678_i_at | 336 | AV022454 (expressed sequence AV022454) | 0 | 0 | 0 | 0.999962 | 0.999955 |
| A (U74A) | 101495_at | 337 | MD3 mRNA | 0 | 0 | 0 | 0.999999 | 0.999932 |
| A (U74A) | 93574_at | 338 | Serpinf1 (serine proteinase inhibitor, serpin) | 0 | 0 | 0 | 0.999983 | 0.999957 |
| A (U74A) | 101571_g_at | 339 | insulin like growth factor binding protein 4 | 0 | 0 | 0 | 1 | 0.99996 |
| A (U74A) | 99024_at | 340 | Mad4 (Max dimerization protein 4) | 0 | 0 | 0 | 0.999996 | 0.999966 |
| A (U74B)2 | 112405_at | 341 | MCT4 (monocarboxylate transporter 4) | 0 | 0 | 0 | 0.999966 | 1 |
| A (U74A) | 94057_g_at | 342 | stearoyl-CoA desaturase gene, exon 6 | 0 | 0 | 0 | 0.999986 | 0.999982 |
| A (U74A) | 101587_at | 343 | Ephx1 (epoxide hydrolase 1, epoxide hydrolase) | 0 | 0 | 0 | 0.999986 | 0.999985 |
| A (U74A) | 92858_at | 344 | secretory leukoprotease inhibitor gene | 0 | 0 | 0 | 0.999983 | 0.999988 |
| A (U74B)2 | 163664_at | 345 | Fadsd2 (fatty acid desaturase 2) | 0 | 0 | 0 | 0.999987 | 0.999986 |
| A (U74A) | 160424_f_at | 346 | farnesyl pyrophosphate synthase (Fpps) mRNA | 0 | 0 | 0 | 0.999999 | 0.999979 |
| A (U74B) 2 | 163063_i_at | 347 | 1500004A08Rik (RIKEN cDNA 1500004A08 gene) | 0 | 0 | 0 | 0.999987 | 0.999991 |
| A (U74A) | 93836_at | 348 | Bnip3 (BCL2/adenovirus E1B 19 kDa-interacting protein 1, integral membrane protein) | 0 | 0 | 0 | 0.999998 | 0.999993 |
| A (U74A) | 104728_at | 349 | Pros1 (protein S (alpha)) | 0 | 0 | 0 | 0.999999 | 0.999995 |
| A (U74B)2 | 164098_at | 350 | Fzd7 (frizzled homolog 7 (Drosophila)) | 0 | 0 | 0 | 0.999998 | 0.999996 |

Fig. 2A-2

| Analysis Name | Probe Set Name | | Gene Name | Change | Change | Change Status | Change p-value | Change p-value |
|---|---|---|---|---|---|---|---|---|
| A (U74A) | 98496_at | 351 | Gys1 (glycogen synthase 1, enzyme) | 0 | 0 | 0 | 0.999997 | 0.999999 |
| A (U74A) | 101084_f_at | 352 | 1110001H19Rik (RIKEN cDNA 1110001H19 gene) | 0 | 0 | 0 | 0.999996 | 1 |
| A (U74A) | 97885_at | 353 | 1810009M01Rik (LR8 protein) | 0 | 0 | 0 | 0.999999 | 0.999999 |
| A (U74A) | 94056_at | 354 | stearoyl-CoA desaturase gene, exon 6 | 0 | 0 | 0 | 0.999999 | 0.999999 |
| A (U74A) | 99599_s_at | 355 | 1110030G05Rik (RIKEN cDNA 1110030G05 gene) | 0 | 0 | 0 | 0.999999 | 0.999999 |
| A (U74A) | 93583_s_at | 356 | Mouse germ line gene fragment for mu-immunoglobulin C-terminus (secreted form) | 0 | 0 | 0 | 0.999999 | 0.999999 |
| A (U74A) | 94304_at | 357 | Anxa6 (annexin A6, calcium binding) | 0 | 0 | 0 | 0.999999 | 0.999999 |
| A (U74A) | 96605_at | 358 | 0610011I04Rik (gene with protein product, function unknown) | 0 | 0 | 0 | 0.999999 | 0.999999 |
| A (U74A) | 99098_at | 359 | farnesyl pyrophosphate synthase (Fpps) mRNA | 0 | 0 | 0 | 0.999999 | 0.999999 |
| A (U74C) | 166934_s_at | 360 | Lamb1-1 (laminin B1 subunit 1) | 0 | 0 | 0 | 0.999999 | 0.999999 |
| A (U74A) | 92637_at | 361 | Pfk1 (6-phosphofructokinase, enzyme) | 0 | 0 | 0 | 0.999999 | 1 |
| A (U74A) | 104313_at | 362 | 2610020G18Rik (RIKEN cDNA 2610020G18 gene) | 0 | 0 | 0 | 0.999999 | 0.999999 |
| A (U74A) | 92851_at | 363 | Cp (ceruloplasmin, copper binding) | 0 | 0 | 0 | 0.999999 | |
| A (U74A) | 93351_at | 364 | Hpgd (hydroxyprostaglandin dehydrogenase 15) | 0 | 0 | 0 | 0.999999 | 1 |

Fig. 2B

EMSA (Brn-3 ACTIVITY

METHOD OF INHIBITING AN ACTIVITY OF A GENE PRODUCT IN A BONE CELL ENCODED BY A NUCLEOTIDE SEQUENCE COMPRISING SEQ ID NO: 50

RELATED APPLICATIONS

This application claims the benefit of U.S. Provisional Application No. 60/432,700, filed Dec. 11, 2002, the entire contents of which is hereby incorporated by reference.

GOVERNMENT SUPPORT

The invention was supported, in whole or in part, by grant DE-07378 from the National Institutes of Health. The Government has certain rights in the invention.

BACKGROUND OF THE INVENTION

Bone production by osteoblasts and bone resorption by osteoclasts is critical for normal bone development and remodeling. Excessive resorption is a key pathogenic component in osteopenic conditions such as osteoporosis, arthritis, periodontitis and certain malignancies. Bone resorption is regulated by a complex system of hormones and locally-produced cytokines that stimulate osteoblasts and stromal cells to express Receptor Activator of NF-κB Ligand (RANKL), which results in the differentiation and activation of osteoclasts. The processes by which osteoclast differentiation and activation occur are currently not well understood.

Additional intracellular signaling pathways may also be important regulators of osteoclastic resorption and bone production by osteoblasts. The identification of the molecules that mediate differentiation and activation of osteoclasts and production of bone by osteoblasts may lead to new methods for regulating bone resorption and bone mineral density, and to new treatments for osteopenic conditions.

SUMMARY OF THE INVENTION

The invention features methods of inhibiting osteoclast-mediated bone resorption by inhibiting activity of a gene product encoded by an osteoclast associated gene. Examples of osteoclast associated genes include OC 1-285, brn3a, brn 3b, and brn3c. Also included are methods of inhibiting osteoclast-mediated bone resorption by inhibiting expression of an osteoclast associated gene. The osteoclast associated genes encode gene products that include, for example, MIP1γ, Brn3a, Brn3b, and Brn3c.

The invention includes methods of inhibiting osteoclastogenesis by contacting an osteoclast precursor cell with an inhibitor of MIP1γ. Examples of precursor cells are monocytes and macrophages. Inhibitors include an antibody that binds to an epitope of MIP1γ. One example of an epitope is a CCR1 receptor binding domain. Inhibitors are also polypeptides that bind to a CCR1 receptor but do not activate the receptor. Inhibitors also do not induce or increase the production of MIP1γ.

The invention also involves methods of promoting osteoclast survival by contacting an osteoclast cell with a MIP1γ polypeptide resulting in a decrease in apoptotic cell death in the presence of the polypeptide compared to that in the absence of the polypeptide. Other agents or compounds for promoting osteoclast survival include RANKL, LPS and IL-1α.

The invention further includes methods of inhibiting proliferation of osteoclast cells by contacting the cells with an inhibitor of MIP1γ expression or activity.

Also described herein are methods of stimulating osteoclast-mediated bone resorption by contacting an osteoclast cell with a MIP1γ polypeptide.

The invention also includes methods of inhibiting osteoclastogenesis by contacting an osteoclast precursor cell with an inhibitor of an activity of a gene product of an osteoclast associated gene. One method for inhibiting osteoclastogenesis is to inhibit the fusion of precursor cells thereby inhibiting the formation of osteoclastic giant cells. The inhibition of fusion of a plurality of precursor cells into an osteoclastic giant cell is inhibited by at least 10%, 20%, 40%, 50%, 60%, 75%, 90%, 95%, or greater. In one example the inhibitor is a polynucleotide that is a decoy oligonucleotide. A decoy oligonucleotide is identical to or similar to the binding site or target site of a POU domain protein, such as the Brn3 family of proteins. Decoy oligonucleotides inhibit binding to endogenous target sites. The inhibitors, including decoy oligonucleotides, inhibit binding of a Brn3 polypeptide to a target site.

The invention also involves methods of inhibiting bone resorption by increasing activity of a gene product of an osteoclast associated gene, such as OC 286-364. Other methods of inhibiting bone resorption involve increasing expression of an osteoclast associated gene, such as OC 286-364.

The invention also includes a reference expression profile. An expression profile includes a pattern of gene expression of two or more genes selected from the group consisting of OC1-364.

OSTEOCLAST MARKER—is a nucleic acid or polypeptide which is differentially expressed in an mature osteoclast cell compared to a non-osteoclast cell or an osteoclast precursor cell. For example, the level of expression of an osteoclast marker (e.g., OC1-285, Brn3a, b, c) is preferentially expressed in osteoclasts. The level of expression of OC1-285 is a least 10%, 20%, 50%, 100% or 200% or greater in osteoclasts compared to non-osteoclast cells. Non-osteoclast cells include monocytes, macrophages, and osteoblasts. The level of expression of a nucleic acid and/or polypeptide is measured using methods known in the art, e.g., RT-PCR and antibody-based immunochemical assays, respectively. Alternatively, the level of expression is reduced by at least 10%, 20%, 50%, 100% or 200% or greater in osteoclasts compared to non-osteoclast cells, as in the case with OC286-364.

The invention further includes methods for determining whether a subject is suffering from or is predisposed to developing a bone disease by providing a biological sample from the subject; detecting at least one osteoclast marker in the biological sample; measuring the level of expression of said at least one osteoclast marker; and comparing the level of expression of said osteoclast marker in said biological sample to the level of expression of the osteoclast marker in a control sample. An alteration in the level of expression of the osteoclast marker in the subject compared to the control sample indicates the presence of or predisposition to a bone disease. An increase in the level of expression of at least one osteoclast marker, OC1-285, Brn3a, Brn3b, Brn3c, MIP-1γ, CCR1, MIP-1α, or RANTES or combinations thereof (for example, in an expression profile), compared to the control sample indicates the presence of or predisposition to a bone disease. A decrease in the level of expression of at least one osteoclast marker, OC 286-364 or combinations thereof (for example, in an expression profile), compared to the control sample indicates the presence of or predisposition to a bone disease.

Bone resorption diseases include osteoporosis, hyperparathyroidism, Paget's disease, inflammatory conditions, rheumatoid arthritis, osteoarthritis, and periodontitis. Bone generating diseases include osteopetrosis, axial osteosclerosis, and Osteopathia striata.

Also described herein are methods for identifying a therapeutic agent for use in treatment of a bone disease by providing a biological sample expressing an osteoclast marker; contacting the cell with a composition comprising a candidate substance; and measuring the level of expression of an osteoclast marker. A change in the level of expression of at least one osteoclast marker or a change in the expression profile of two or more osteoclast markers in the presence of the substance compared to the expression of said osteoclast marker in the absence of the substance, identifies the candidate substance as a potential therapeutic agent.

BRIEF DESCRIPTION OF THE DRAWINGS

FIGS. 1A-1E are a list of the genes expressed at higher levels in RAW 264.7 macrophage-like cells stimulated with Receptor Activator of NFκB Ligand (RANKL) and normal mouse bone marrow macrophages stimulated with Macrophage-Colony Stimulating Factor (M-CSF) and RANKL, compared to unstimulated cells (control). "I" in the "Change" columns means that expression of the indicated gene is increased upon stimulation compared to control samples. The first column marked "Change" refers to samples of normal bone marrow cells and the second column marked "Change" refers to samples of RAW264.7 cells. "Status" refers to the net result (increased expression) of the indicated gene. "Change p value" is calculated by Affymetrix software for normal bone marrow cells and for RAW264.7 cells. "Average" refers to the average p values of the two samples.

FIGS. 2A-2B are a list of the genes expressed at lower levels in RAW 264.7 macrophage-like cells stimulated with Receptor Activator of NFκB Ligand (RANKL) and normal mouse bone marrow macrophages stimulated with Macrophage-Colony Stimulating Factor (M-CSF) and RANKL, compared to unstimulated cells (control). "D" in the "Change" columns means that expression of the indicated gene is decreased upon stimulation compared to control samples. The first column marked "Change" refers to samples of normal bone marrow cells and the second column marked "Change" refers to samples of RAW264.7 cells. "Status" refers to the net result (decreased expression) of the indicated gene. "Change p value" is calculated by Affymetrix software for normal bone marrow cells and for RAW264.7 cells. "Average" refers to the average p values of the two samples.

DETAILED DESCRIPTION OF THE INVENTION

Figure 3A:
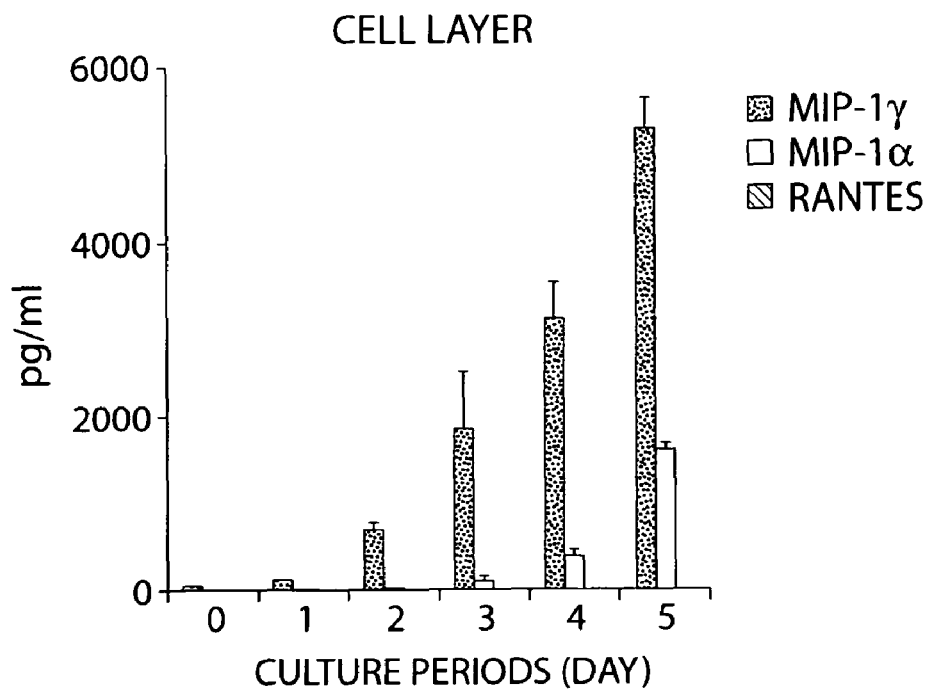
FIGS. 3A-3D are bar graphs of the kinetics of chemokine production by RANKL-stimulated RAW264.7 and bone marrow cells. (A) RAW264.7 cells were stimulated with RANKL (10 ng/ml) for 5 days. (B) Bone marrow cells were stimulated with RANKL (20 ng/ml) and M-CSF (50 ng/ml) for 7 days. Chemokine levels were measured by ELISA. Results represent the mean±SD of triplicate cultures.

MIP-1 Gamma Promotes RANKL-Induced Osteoclast Formation and Survival

Osteoclastic bone resorption consists of multiple steps, including the differentiation of osteoclast precursors, the fusion of mononuclear cells to form mature multinucleated osteoclasts, activation to resorb bone and finally the survival of activated osteoclasts. RANKL (Receptor Activator of NF-κB Ligand), also known as TRANCE or OPGL, is a member of the TNF family and is one of key molecules that regulates both osteoclastogenesis and bone resorption. RANKL expression by osteoblasts as well as by activated T cells has been shown to regulate these processes. However, the participation of additional factors, including autocrine factors induced by RANKL stimulation, is less well characterized.

Chemokines play an important role in immune and inflammatory responses by inducing the migration and adhesion of leukocytes. Several chemokines regulate the migration and differentiation of OC, including MIP-1α and IL-8. However, the cellular source(s) of these chemokines, and their role in the overall regulation of bone mass remains unclear.

Macrophage inflammatory protein-1 gamma (MIP-1γ) is a CC chemokine family member. MIP-1γ induces the chemotaxis of $CD4^+$ and $CD8^+$ T cells and monocytes in vitro, and shows potent suppressive activity on the colony formation of murine bone marrow myeloid progenitor cells. MIP-1γ mRNA is widely expressed in most tissues of normal mice except brain.

Using gene microarrays, we found that MIP-1γ mRNA expression was strongly upregulated in RANKL-induced OC. MIP-1γ is involved in RANKL-induced OC formation, survival, and activation in bone resorption, likely via an autocrine pathway.

Mice and Reagents

Three to five week-old BALB/c mice were obtained from the Jackson Laboratory, Bar Harbor, Me. Recombinant mouse RANKL (RANKL) and recombinant mouse M-CSF (M-CSF) were purchased from PeproTech Inc (Rocky Hill, N.J.). Recombinant mouse MIP-1γ, anti-mouse MIP-1γ antibody and control $IgG_1$ antibody ($IgG_1$ antibody) were obtained from R&D Systems (Minneapolis, Minn.).

Cell Culture and Differentiation of RAW264.7 and Bone Marrow Cells.

RAW264.7, a mouse macrophage/monocyte cell line, was purchased from ATCC (TIB-71). Cells were cultured in Dulbecco's modification of Eagle's medium (DMEM; JRE Biosciences, Lenexa, Kans.) supplemented with 10% FBS (Gibco, Grand Island, N.Y.), 1.5 g/l sodium bicarbonate and penicillin/streptomycin (Gibco). To generate osteoclasts, RAW 264.7 cells were plated in 24-well plates at a density of $1 \times 10^4$ cells/well. Cells were stimulated with 10 ng/ml of recombinant mouse RANKL for 5 days. Mouse bone marrow (BM) cells were collected from femora and tibiae. Three to five week-old female mice were killed by cervical dislocation under light ether anesthesia. Femora and tibiae were dissected, BM cells were flushed out and cultured in α-MEM (Cambrex, Walkersville, Md.) supplemented with 10% FBS, 2.0 g/l sodium bicarbonate and penicillin/streptomycin. BM cells were seeded into 24-well plates at a density of $2 \times 10^6$ cells/well in medium supplemented with 20 ng/ml of RANKL and 50 ng/ml of recombinant mouse M-CSF for 7 days. All cultures were maintained at 37° C. in a humidified atmosphere of 5% $CO_2$ in air, with changes of medium every other day. Osteoclast numbers were evaluated by counting tartrate-resistant acid phosphatase (TRAP)-positive giant cells. At culture termination, cells were washed with PBS and fixed in 10% formalin for 5 min followed by ethanol/acetone (1:1) for 1 min. Osteoclasts were stained for TRAP in the presence of 0.05 M sodium tartrate (Sigma-Aldrich, St. Louis, Mo.), napthol AS-MX phosphate (Sigma-Aldrich) as substrate, and fast red LB salt (Sigma-Aldrich). TRAP-positive multinuclear cells (3 or more nuclei/cell) were counted under light microscopy.

Gene Array Analysis

Two array systems were used to detect differences in gene expression between undifferentiated precursor cells and osteoclasts: the Atlas™ Mouse 1.2 array (Clontech Laboratories, Inc. Palo Alto, Calif.) and the MG-U73 chip (Affymetrix Santa Clara, Calif.). To enrich for differentiated OC, RANKL-stimulated cultures were gently trypsinized for 1 min to remove other less adherent cells. This treatment generated a population of >80% OC.

For analysis of gene expression in OC, total RNA was isolated from both undifferentiated cells and purified OC using TRIzol reagent (Invitrogen Co., Carlsbad, Calif.). Total RNA was subsequently treated with DNase I, (Ambion, Austin, Tex.) to remove contaminating genomic DNA and quantified by spectrophotometry. The Atlas™ array, was hybridized to a radioactively labeled mixed cDNA probe obtained by reverse transcription of 4 µg of total RNA, according to the manufacturer's instructions. After hybridization, the arrays were washed to remove unbound probe and exposed to X-ray film. The level of gene expression was analyzed and normalized using NIH Image™ software. The MG-U73 chip was hybridized to a biotinylated mixed cDNA probe, washed and stained according to the standard Affymetrix GeneChip protocol. The level of gene expression was analyzed and normalized using statistical algorithms provided by Affymetrix.

Modulation of RANKL-Induced Osteoclastogenesis

MIP-1γ (0.1, 0.5, 2.0 ng/ml) was added to cultures of RAW264.7 and BM cells to examine its effect on RANKL-induced osteoclast differentiation. To eliminate possible effects of contaminating LPS, 1 µg/ml of polymyxin B (Sigma-Aldrich) was simultaneously added to some cultures. To assess the effect of endogenous MIP-1γ, anti-MIP-1γ antibody or $IgG_1$ control antibody (0.5, 5.0 µg/ml) was added to cultures of RAW264.7 and BM cells stimulated with RANKL.

Measurement of Chemokines

Chemokines were measured in culture supernatants and cell lysates of RAW264.7 and BM cells. After supernatants were collected, cells were washed with PBS and lysed in 500 µl of protein extraction buffer (0.5% Triton-X100, 50 mM Tris-HCl, 0.3 M NaCl and 5 mM EDTA). MIP-1γ, MIP-1α and RANTES levels were determined using commercially available ELISA kits (R&D Systems).

Semi-Quantitative RT-PCR

Semi-quantitative RT-PCR was used to examine CCR1 receptor gene expression in undifferentiated cells and purified osteoclasts. For this, 1 µg total RNA was reverse transcribed using Superscript II (Invitrogen) and random primers according to the manufacturer's instructions. cDNA was subjected to PCR amplification with Taq polymerase (Qiagen, Valencia, Calif.) using specific mouse CCR1 primers:

```
sense:
5'-GTGTTCATCATTGGAGTGGTGG-3',    (SEQ ID NO: 1)

antisense:
5'-GGTTGAACAGGTAGATGCTGGTC-3'.   (SEQ ID NO: 2)
```

Evaluation of Osteoclast Survival and Activity

For cell survival analysis, OC's were generated from RAW264.7 cells for 5 days. Adherent OC's were washed extensively with PBS to completely remove RANKL. Cells were subsequently cultured without or with 10 ng/ml of RANKL in the presence/absence of 2.0 ng/ml of MIP-1γ. Neutralizing anti-MIP-1γ antibody (5 µg/ml) or control $IgG_1$ antibody (5 µg/ml) was simultaneously added with RANKL to determine the role of MIP-1γ in apoptosis of RANKL-induced osteoclasts. After 24, 48, and 72 hr, survival was determined by counting adherent TRAP-positive osteoclasts.

To determine the effect of MIP-1γ on bone resorbing activity, OC's were generated in three-dimensional collagen gels (Chemicon, Temecula, Calif.). Sixty mm dishes were covered with a collagen gel solution prepared according to the manufacturer's instructions. RAW264.7 cells were seeded onto the gels and cultured with 10 ng/ml of RANKL for 5 days. Cells were removed following digestion of gels with 1000 U/ml collagenase (Sigma-Aldrich) at 37° C. for 30 min. Aliquots of the harvested cell suspension were seeded onto sub-micron calcium phosphate films (Osteologic™; BD Biosciences, Bedford, Mass.) in 250 µl of medium. Cells were unstimulated (control), or stimulated with 10 µg of RANKL or MIP-1γ (2.0, 5.0, 10 ng/ml). After 24 hr, the cells were removed with 5% sodium hypochlorite and resorbed areas were visualized using light microscopy. The size of resorbed areas was quantified using NIH Image™.

Preparation of Nuclear Extracts

Osteoclasts were generated by RANKL stimulation of RAW264.7 cells for 5 days, and were enriched by a brief trypsinization which removed most mononuclear cells. Osteoclasts were washed twice with PBS, pH 7.4, followed by suspension in 800 µl ice-cold lysis buffer (mmol/l: HEPES 10; KCL 10; EDTA 0.1; EGTA 0.1; DTT 1.0; PMSF 1.0; aprotinin 10 µg/ml, pepstatin 10 µg/ml, leupeptin 10 µg/ml). The collected samples were incubated on ice for 30 min, vortexed for 30 sec after addition of 50 µl 10% Nonidet-P40, and centrifuged for 10 min at 4° C. at 5,500×g. The nuclei-containing pellets were suspended in ice-cold buffer (mmol/l: HEPES 20; NaCl 400; EDTA 1.0; EGTA 1.0; DTT 1.0; PMSF 1.0; aprotinin 10 µg/ml, pepstatin 10 µg/ml; leupeptin 10 µg/ml), incubated on ice for 2 h with frequent mixing, and centrifuged for 10 min at 4° C. at 14,000×g. The supernatants were collected as nuclear extract and stored at −70° C. The total protein concentration was determined using a protein assay kit (Pierce, Rockford, Ill.).

Electrophoretic Mobility Shift Assays (EMSA)

NF-κB binding studies were performed using double stranded oligonucleotides containing an NF-κB consensus binding site. The oligonucleotides were end-labeled with $^{32}$[P]-ATP using T4 polynucleotide kinase (Promega, Madison, Wis.) and incubated with the nuclear extract for 20 min at room temperature. The samples were loaded on a 4% non-denaturing polyacrylamide gel. After electrophoresis, the gel was dried and exposed to Kodak film.

Apoptosis Assays

Caspase-3 activity and degradation of DNA were examined for detection of apoptosis of OC's. OC's were obtained by RANKL stimulation of RAW 264.7 cells for 5 days, extensively washed, and re-stimulated with MIP-1γ or RANKL in the presence/absence of anti-MIP-1γ antibody. After 24 hr, cells were fixed in 4% paraformaldehyde, and were labeled with the caspase-3 substrate Rhodamine 110 (100 μM) and 2.4 nM of TOTO-3 for nuclear staining (Molecular Probes, Eugene, Oreg.) at 37° C. for 30 min. Cells were washed and viewed using a fluorescence microscope. Apoptotic cells exhibited bright green fluorescence. For DNA fragmentation determinations, OC's were washed with PBS, and lysed in a buffer consisting of 5 mM Tris-HCl (pH 8.0), 20 mM EDTA, 0.5% (v/v) Triton X-100 and 0.1% SDS. High-molecular mass DNA was removed by centrifugation at 14000×g for 30 min. The supernatants were sequentially extracted with equal volumes of phenol/chloroform/isoamyl alcohol (25:24:1), and the soluble DNA was precipitated with 1 ml ethanol in the presence of 0.3 M sodium acetate. The DNA was resuspended in TE buffer and treated with DNase-free RNase (0.1 μg/μl) (Roche Diagnostics Corporation, Indianapolis, Id.) for 1 hr at 30° C. DNA fragmentation was analyzed by 1.5% agarose-gel electrophoresis.

Statistical Analysis

In all studies, differences between groups were analyzed using Student's t test with the Bonferroni correction for multiple comparisons.

Induction of MIP-1γ Expression by RANKL During Osteoclastogenesis

Osteoclast formation was induced by RANKL stimulation of RAW 264.7 macrophages for 5 days, or by stimulation of normal mouse bone marrow cells for 7 days with M-CSF and RANKL. RANKL-stimulated RAW264.7 and bone marrow cells differentiated into TRAP positive osteoclasts that expressed high levels of the osteoclast markers TRAP, cathepsin K and the proton pump subunit ATP6I, and produced resorption pits on bone slices and calcium phosphate-coated slides.

Two gene array systems (Atlas™ and Affychip™) were used to study gene expression following RANKL induction of osteoclast formation. Total RNA was extracted from RANKL-induced osteoclasts, and was used as a template to generate mixed cDNA probes. In the Atlas system (1100 genes), a highly significant up-regulation of mRNA was obsweved for the chemokine MIP-1γ in RANKL-stimulated osteoclasts derived from RAW264.7 cells, compared to unstimulated precursor cells (Table 1). This result was confirmed and extended using the Affymetrix system (32,000 genes) and mRNA derived from osteoclasts induced from normal bone marrow as well as RAW264.7 cells. The induction of MIP-1γ was more significant than any other chemokine or cytokine genes represented on these arrays.

TABLE 1

Array analysis of MIP-1γ gene expression in osteoclasts

| Atlas ™ | RAW264.7 | |
|---|---|---|
| Differentiated osteoclasts/ undifferentiated cells | 5.54* | |
| MG-U73 chips | RAW264.7 | Bone Marrow |
| Differentiated osteoclasts vs undifferentiated cells | <0.000001** | <0.000001** |

*Ratio of intensity of gene expression, normalized to housekeeping genes.
**p value, Wilcoxon's signed rank test.

Expression of C-C Chemokines in Developing Osteoclasts

MIP-1γ binds to the CCR1 receptor, which is also activated by related C-C chemokines MIP-1α and RANTES. The production of MIP-1γ, MIP-1α, and RANTES proteins was examined during the process of RANKL-induced osteoclastogenesis from RAW264.7 cells. As shown in FIG. 3A, RANKL strongly stimulated the production of MIP-1γ in both cell lysates and culture supematants over the 5-day culture period. MIP-1α was also induced by RANKL at about 10-fold lower levels. The levels of MIP-1α in supernatants peaked by day 2, although cell-associated levels continued to increase to day 5. RANTES was also weakly induced by RANKL, at levels about 1-2% of those of MIP-1γ at any time point (maximum: 50 pg/ml).

Figure 3B:
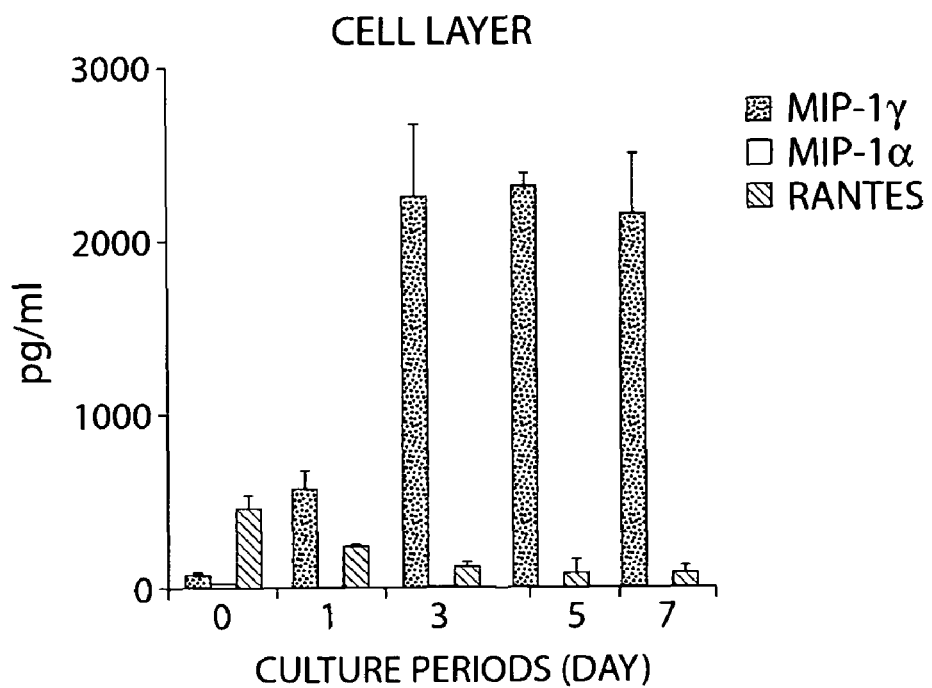
Figure 3C:
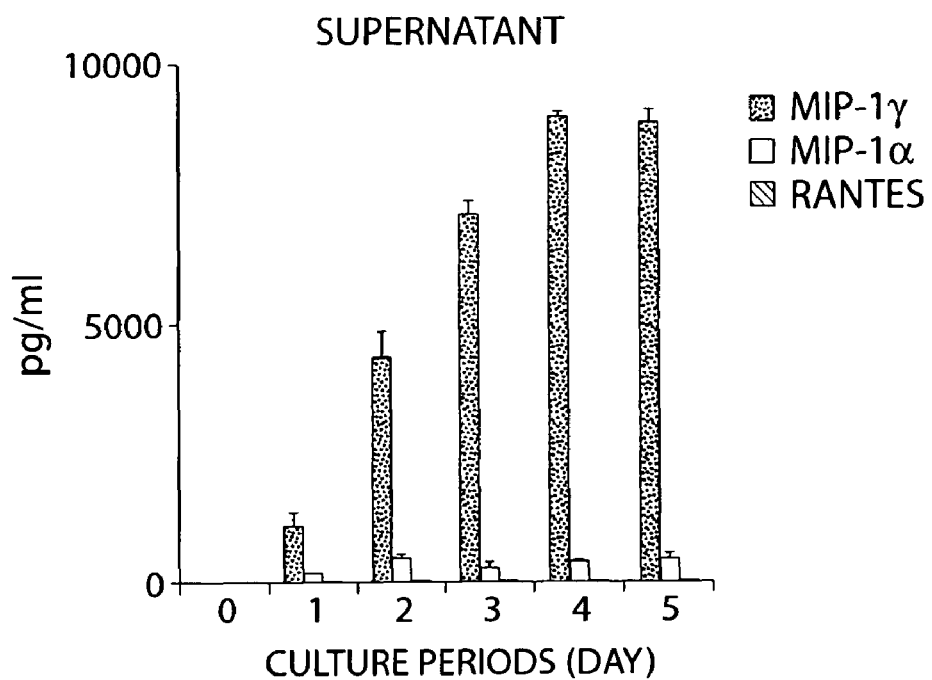
Figure 3D:
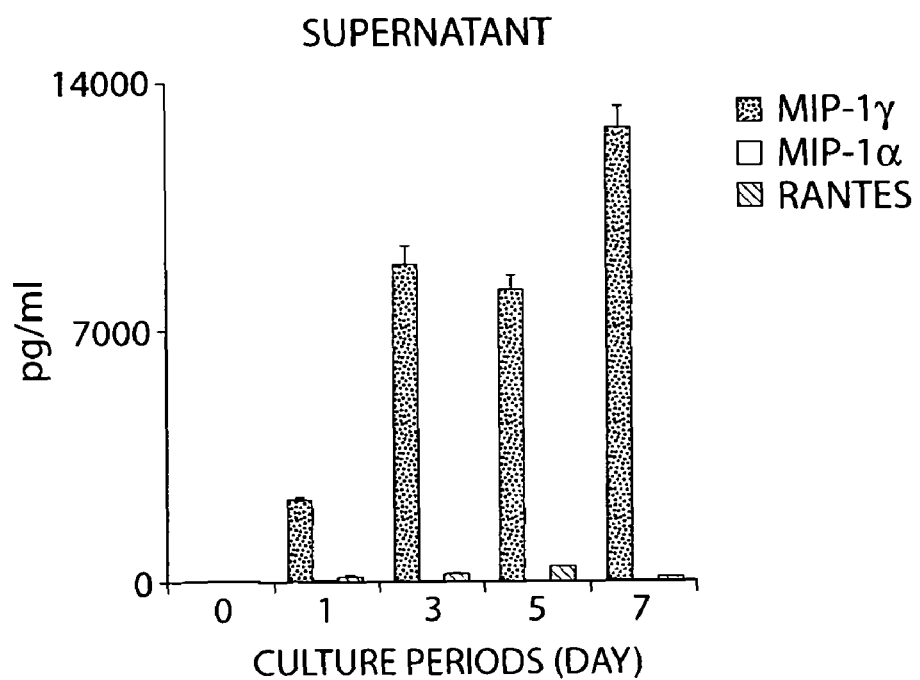
Figure 4A:
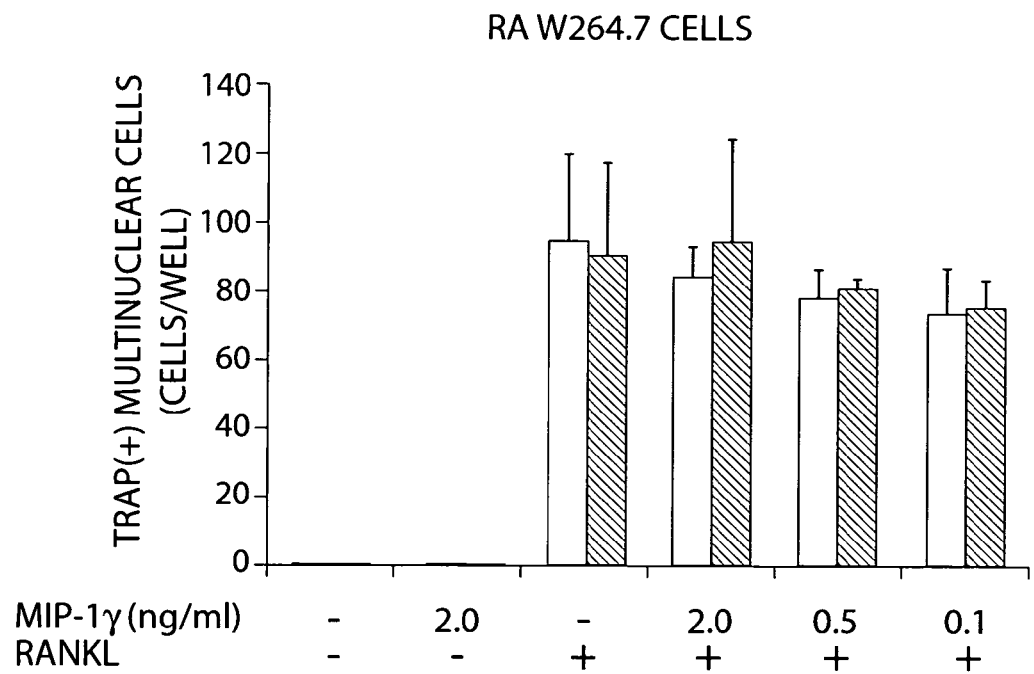
FIGS. 4A-4B are bar graphs of the effect of exogenous MIP-1γ on RANKL-induced osteoclast differentiation. (A) RAW264.7 cells were stimulated for 5 days with the indicated doses of MIP-1γ, in the presence or absence of RANKL (10 ng/ml). (B) Bone marrow cells were stimulated for 7 days with MIP-1γ in the presence or absence of RANKL (20 ng/ml) and M-CSF (50 ng/ml). The culture medium was supplemented with (hatched columns) or without (open columns) 1 μg/ml of polymyxin B to block any contaminating LPS. TRAP-positive cells with >3 nuclei were counted as osteoclasts. The results shown are the mean±SD of three independent experiments.
Figure 4B:
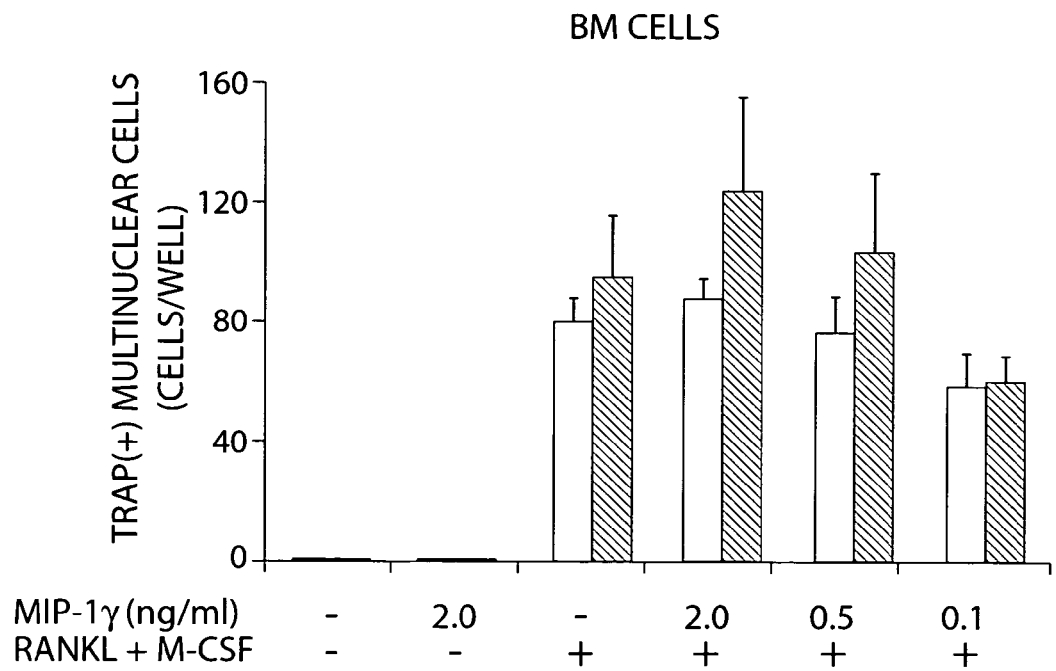

MIP-1γ was similarly induced following RANKL stimulation of normal bone marrow cells (FIG. 3B). However, compared to RAW264.7 cells, RANTES was expressed initially at higher levels, but expression declined with increasing times after culture induction, and MIP-1α was nearly undetectable. MIP-1γ is the predominant C-C chemokine produced by RANKL-stimulated precursor cells during osteoclastogenesis.

CCR1 Receptor Expression by Osteoclasts

RAW 264.7 and bone marrow cells were examined for the expression of CCR1 receptor mRNA upon RANKL stimulation. As shown in FIG. 3, CCR1 mRNA was undetectable in unstimulated RAW 264.7 cells, whereas it was present at low levels in unstimulated bone marrow cells. RANKL stimulation strongly induced CCR1 mRNA in RAW 264.7 and, to a lesser extent, in bone marrow cells. Thus, RANKL induces both MIP-1γ and its receptor during osteoclast differentiation, indicating the operation of an autocrine pathway.

Modulation of Osteoclastogenesis MIP-1γ

Figure 5A:
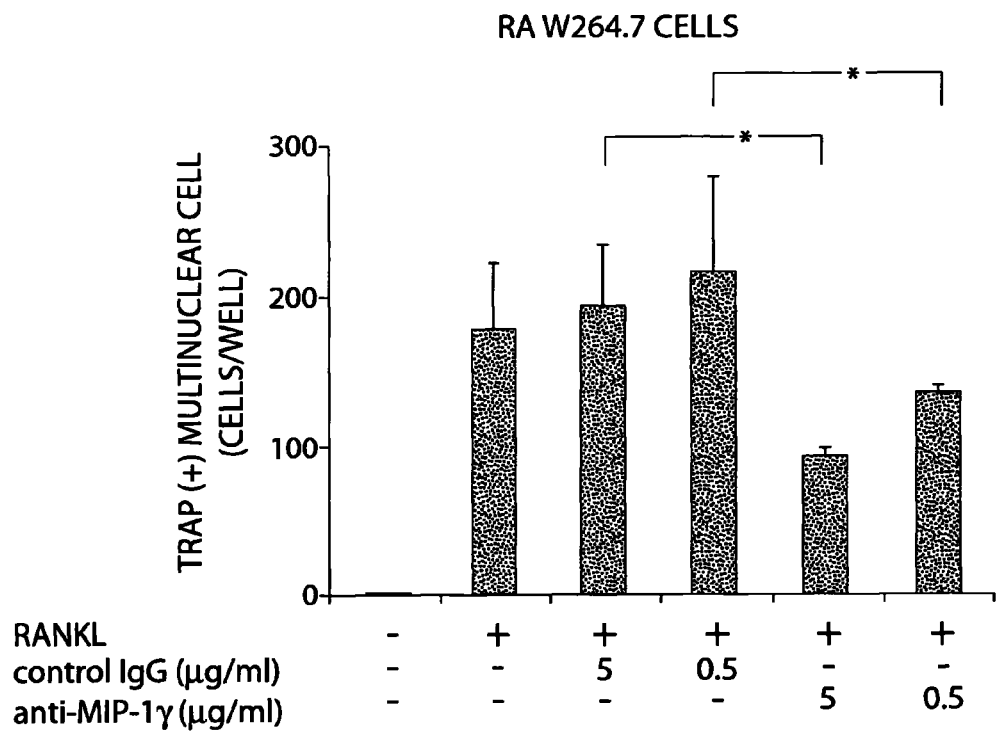
FIGS. 5A-5B are graphs of the anti-MIP-1γ antibody reduction of RANKL-induced osteoclast differentiation. (A) RAW264.7 cells were cultured with RANKL (10 ng/ml) and neutralizing anti-MIP-1γ antibody or an unreactive control IgG1 antibody for 5 days. (B) Bone marrow cells were cultured in the presence of RANKL (20 ng/ml) and M-CSF (50 ng/ml), in the presence of neutralizing anti-MIP-1γ antibody or unreactive control IgG1 antibody for 7 days. TRAP-positive cells with >3 nuclei were counted as osteoclasts. The results shown are the mean±SD of three independent experiments. *p<0.05; **p<0.01.
Figure 5B:
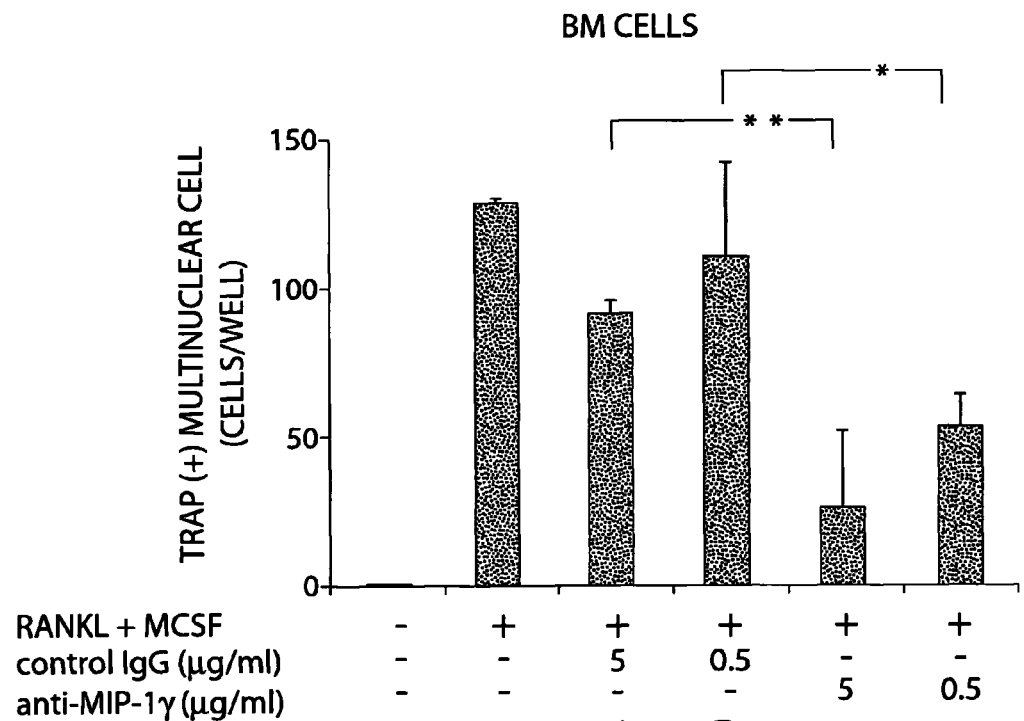

The role of endogenously produced MIP-1γ was examined in RANKL-induced osteoclastogenesis in RAW 264.7 and normal bone marrow cells. A neutralizing anti-MIP-1γ antibody was added to cultures beginning on day 0, and was replenished periodically throughout the osteoclast induction period. As seen in FIG. 5, in both cell systems the addition of anti-MIP-1γ antibody resulted in a decreased number of TRAP positive osteoclasts, relative to control IgG1 antibody. The reduction was approximately 60%, in cultures treated with 5 μg/ml of anti-MIP-1γ antibody, and 45% in cultures treated with 0.5 μg/ml antibody. These findings were replicated in two additional experiments.

Figure 6:
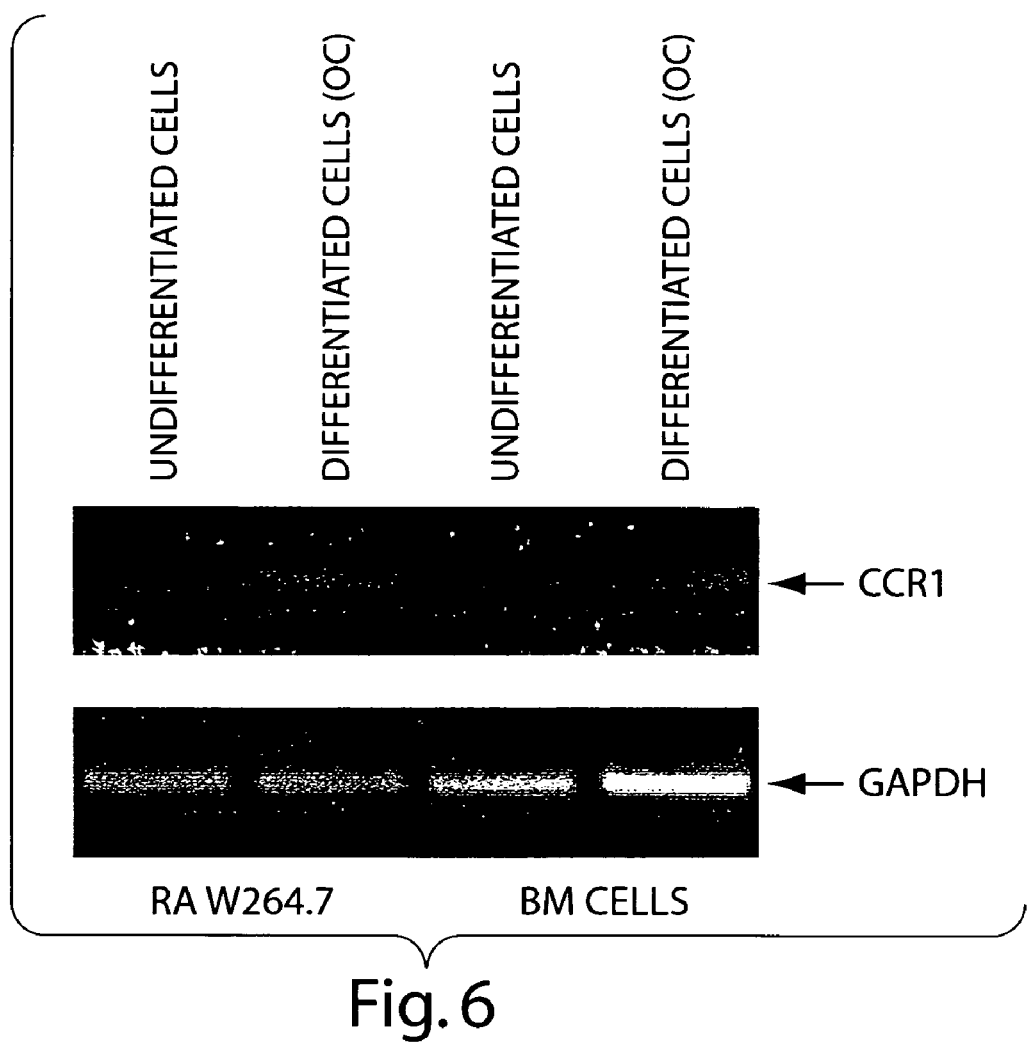
FIG. 6 is a series of photographs of gels, which show CCR1 chemokine receptor expression in RANKL-induced osteoclasts. Osteoclasts were induced by RANKL from RAW264.7 and bone marrow cells. mRNA specific for CCR1 was amplified by semi-quantitative RT-PCR for CCR1 and GAPDH as a control. PCR was performed under conditions determined to be in the liner range of product formation.

The effect of adding exogenous recombinant MIP-1γ on osteoclast formation was also determined. As seen in FIG. 6, TRAP positive osteoclasts were not induced by MIP-1γ alone, nor did exogenous MIP-1γ have a synergistic effect with RANKL on osteoclastogenesis in either cell system. These results are consistent with the high level of endogenous MIP-1γ production. Endogenous MIP-1γ increases RANKL-induced osteoclast formation, but has no independent ability to induce osteoclastogenesis.

Effect of MIP-1γ on Osteoclast Survival

Figure 7:
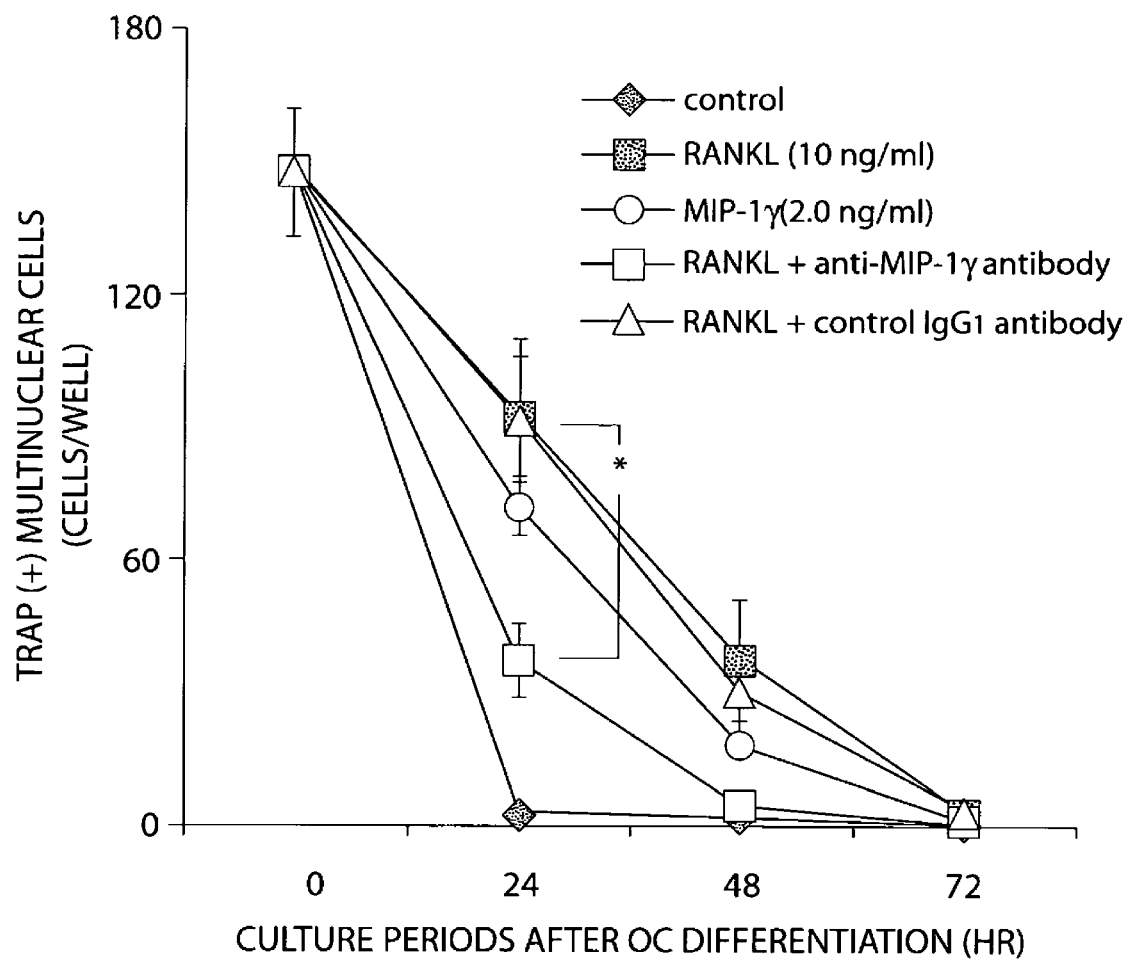
FIG. 7 is a line graph of MIP-1γ enhancement of osteoclast survival. RAW264.7 cells were stimulated with RANKL (10 ng/ml) for 5 days, extensively washed, and subsequently stimulated with RANKL (10 ng/ml), MIP-1γ (2 ng/ml) or medium as a control. Neutralizing anti-MIP-1γ antibody (5 μg/ml) or control IgG$_1$ antibody (5 μg/ml) were simultaneously added with RANKL to determine the role of MIP-1γ in RANKL-stimulated osteoclast survival. TRAP-positive cells with >3 nuclei were counted as osteoclasts. The results shown are the mean±SD of three independent experiments. *p<0.05 RANKL+control antibody vs RANKL+anti-MIP-1γ.

Mature osteoclasts rapidly undergo apoptosis in the absence of bone resorptive stimuli such as RANKL, LPS or IL-1α. RANKL was removed from cultures of differentiated osteoclasts by extensive washing of cells on day 5. Cells were then recultured for an additional 24 to 72 hours in the presence or absence of MIP-1γ or RANKL as a positive control. As shown in FIG. 7, the number of osteoclasts was reduced by 90% after 24 hours in the absence of a stimulating agent (medium alone). RANKL re-stimulation promoted osteoclast survival, as indicated by a 30% reduction in viable TRAP positive cells after 24 hours. The addition of MIP-1γ alone also prevented cell death, albeit somewhat less effectively than RANKL itself. As indicated (FIG. 7), the pro-survival activity of RANKL was reduced by approximately 60% in the presence of anti-MIP-1γ antibody whereas an isotype-matched control IgG1 antibody had no effect.

Figure 8A:
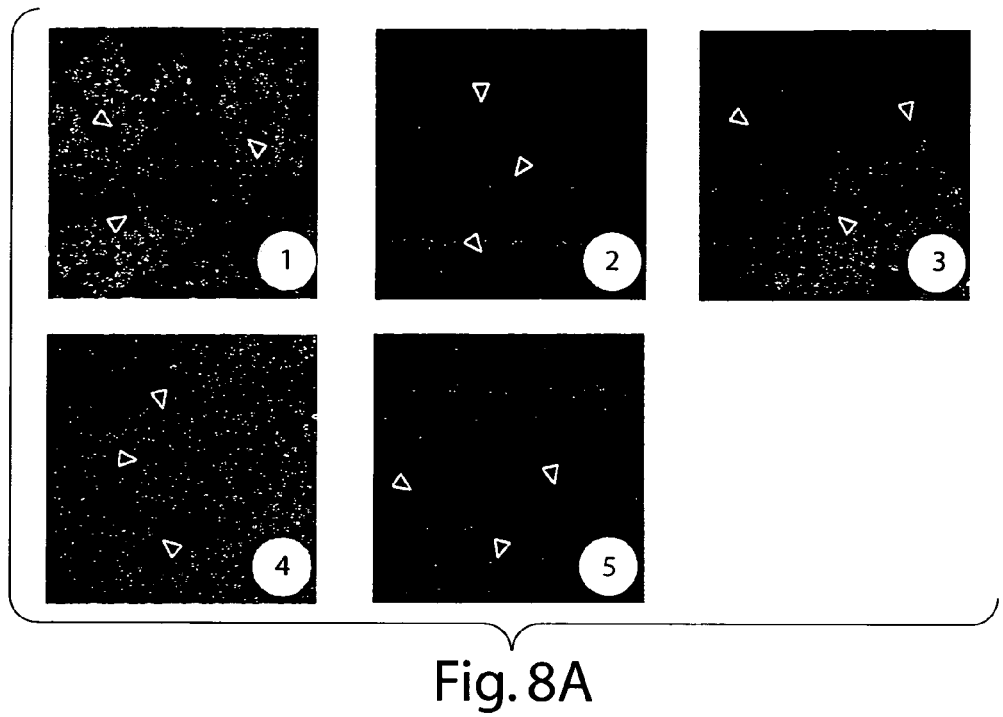
FIGS. 8A-8B are a series of photographs (A) and an autoradiograph (B). (A) Shows the anti-apoptotic effect of MIP-1γ on mature osteoclasts. RANKL induced osteoclasts were washed and re-cultured with (1) medium, (2) RANKL, (3) MIP-1γ (4) RANKL+anti-MIP-1γ antibody (5 μg/ml), or (5) RANKL+control IgG$_1$ antibody (5 μg/ml) for 24 hr. Cell staining with Rhodamine 110 (green) indicates caspase-3 activity; TOTO-3 (blue) counterstains nuclei. Arrowhead: osteoclast. Magnification: 100×. (B) Effect of MIP-1γ on NF-κB activation in osteoclasts. Osteoclasts were generated by RANKL stimulation of RAW264.7 cells for 5 days, washed, and re-stimulated with RANKL (10 ng/ml) (lane 4), MIP-1γ (10 ng/ml) (lane 5) or medium (lane 3) as a control for 12 hr. Nuclear extracts were assessed for NF-κB activity by EMSA. Positive control: day 5 RANKL-stimulated osteoclasts (lane 2); negative control; no nuclear extract (lane 1).

That the loss of osteoclasts was the result of apoptosis rather than necrosis was demonstrated using a fluorescence-based assay for the specific activity of caspase 3 (FIG. 8A). Osteoclasts cultured in the presence of RANKL exhibited minimal apoptosis (panel 2), compared to cells from which RANKL was removed (panel 1). Cells cultured with MIP-1γ alone were partially protected from apoptosis (panel 3). The pro-survival inhibiting effect of RANKL was demonstrated to be partially dependent on its ability to induce MIP-1γ, as shown by anti-MIP-1γ antibody blockade of the protective effect of RANKL (panel 4 vs 5). These results were further confirmed in parallel by DNA fragmentation studies.

Figure 8B:
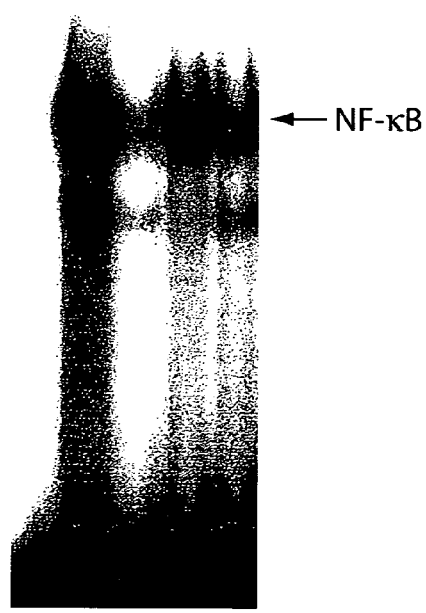

Given that many of the factors that promote osteoclast survival, including RANKL, act by stimulating NF-κB, the effect of MIP-1γ on NF-κB transcription factor was examined. As shown in FIG. 8B, following extensive washing of mature osteoclasts, RANKL restimulation strongly induced NF-κB DNA binding activity in mature osteoclasts, as assessed by electrophoretic mobility shift assay. MIP-1γ by itself also stimulated NF-κB, but less strongly than RANKL, which correlated with the level of its pro-survival activity (FIG. 8A). Thus, MIP-1γ promotes the survival of mature osteoclasts by preventing apoptosis.

Effect of MIP-1γ on Bone Resorbing Activity of Mature Osteoclasts

Figure 9A:
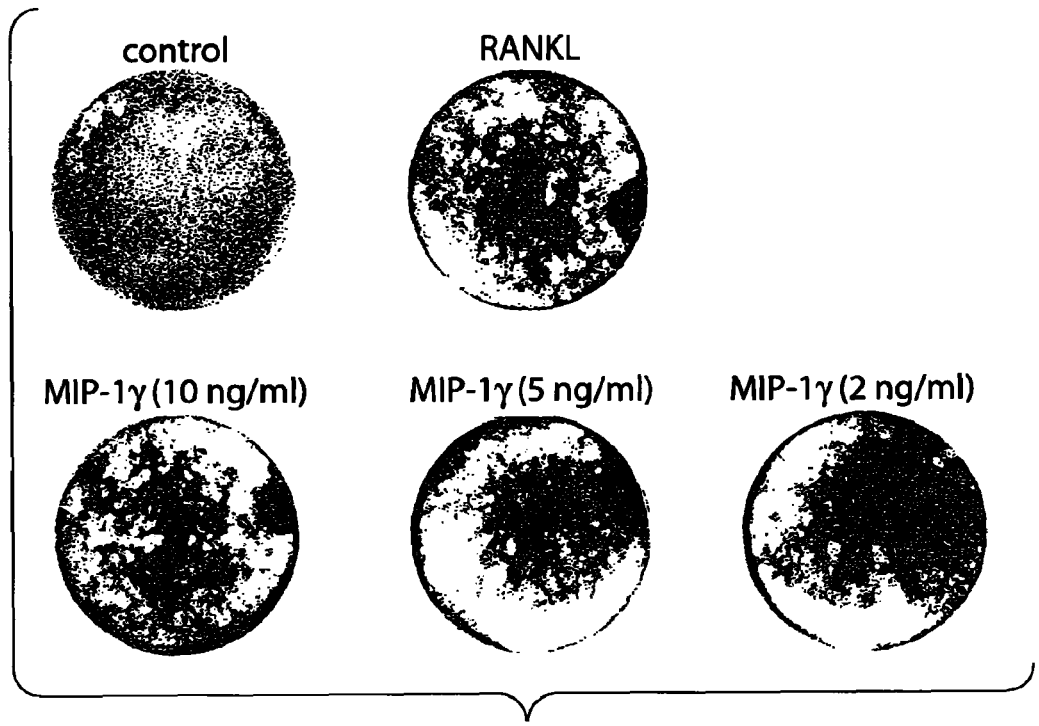
FIGS. 9A-9B are a series of photomicrographs (A) and a bar graph (B) showing that MIP-1γ enhances the activation of pre-formed osteoclasts. RAW264.7-derived osteoclasts recovered from collagen gel cultures, and were plated on Osteologic Multitest Slide™ to assess resorptive activity without/with RANKL (10 ng/ml) or MIP-1γ (2, 5 and 10 ng/ml). (A) Photomicrograph of resorption areas visualized by light microscopy (10×). (B) The size of resorbed areas was quantified using NIH Image™. Data represent the mean±SD of triplicate cultures.
Figure 9B:
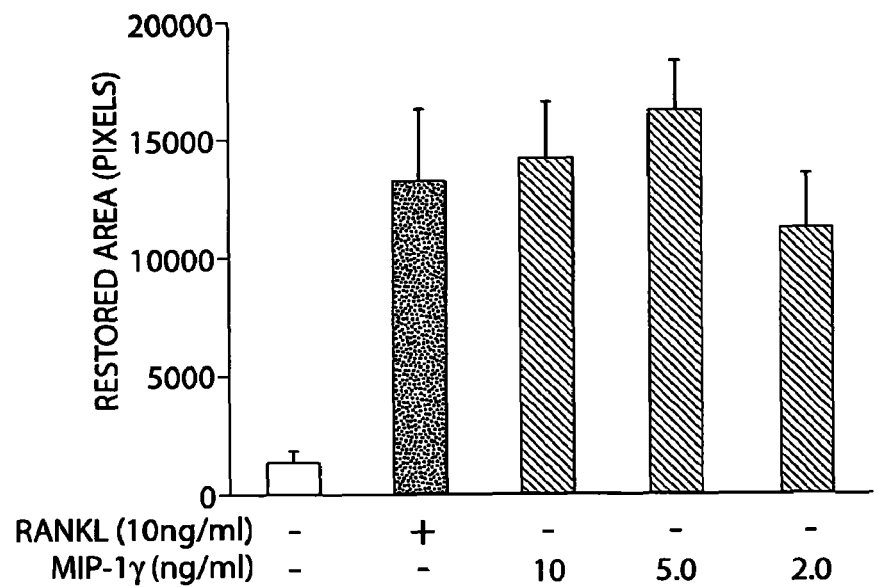

RANKL-induced RAW264.7 cells were cultured in three-dimensional collagen gels, isolated by enzymatic digestion, and replated onto sub-micron calcium phosphate films for an additional 24 hours in the presence/absence of MIP-1γ or RANKL as a positive control. As shown in FIG. 9, osteoclasts were stimulated to form numerous resorption pits in the presence of added RANKL, but not in its absence. The addition of MIP-1γ alone also resulted in a marked stimulation of resorption, to a level similar to that seen with RANKL stimulated cells. Therefore, MIP-1γ stimulates the activation as well as the survival of mature osteoclasts.

Extensive cross talk occurs between the immune and skeletal systems. In particular, the differentiation and activity of osteoclasts, and hence bone mass, can be modulated by cytokines/chemokines, many of which derive from immune cells. Gene arrays were used herein to identify mediators that were up-regulated following RANKL stimulation of osteoclast precursor cells. MIP-1γ was most strongly up-regulated in osteoclasts derived from RANKL-stimulated monocyte/macrophages. Expression of CCR1, the high affinity receptor for MIP-1γ, was also increased following RANKL stimulation. Inhibition of MIP-1γ expression or activity resulted in decreased osteoclast formation and reduced resorptive activity. Furthermore, MIP-1γ promoted osteoclast survival and prevented apoptosis, and was responsible for a major proportion of the pro-survival activity of RANKL itself. MIP-1γ regulates osteoclastic bone resorption, via effects on cell differentiation, survival and activation.

MIP-1γ is a C-C chemokine with a predicted length of 100 amino acids, which is identical with CCF 18. MIP-1γ is constitutively expressed by a wide variety of tissues, and exclusively binds to the CCR1 receptor on mouse neutrophils in vitro. MIP-1γ expression is increased in rat bone marrow cells stimulated with RANKL.

Two other C-C chemokines, MIP-1α and RANTES, also bind to CCR1, and are therefore involved in modulating osteoclast development and function. However, MIP-1γ iss by far the predominant chemokine protein produced by RANKL-stimulated RAW264.7 and bone marrow cultures, compared to relatively minor amounts of MIP-1α and RANTES. MIP-1α and IL-8 inhibit the resorption of isolated rat osteoclasts, and these chemokines participate in osteoclast migration, but not resorption and survival. Conversely, increased levels of MIP-1α, which is produced and secreted by osteoblasts, correlates with an increase in the number of osteoclasts in a porcine bone marrow culture system. MIP-1α also stimulates osteoclast formation in human marrow cultures and also enhances formation of osteoclasts induced by PTHrP and RANKL. The RANTES gene is upregulated in RANKL-induced osteoclasts derived from mouse bone marrow cells. Neutralization of MIP-1γ reduced osteoclast formation by approximately 60%. MIP-1α and RANTES also participate in RANKL-induced osteoclastogenesis following interaction with CCR1, albeit with a more modest effect. Alternatively, residual MIP-1γ independent RANKL-induced osteoclast formation may proceed via pathways independent of these chemokines.

Osteoclasts rapidly undergo apoptosis unless stimulated by exogenous mediators, which include M-CSF, RANKL, IL-1, FGF2, or LPS. With the exception of M-CSF and FGF2, these survival-promoting stimuli act by inducing NF-κB, which is an anti-apoptogen. FGF-2, which directly stimulates activation and survival of mature osteoclasts, mediates its effects through p42/p44 MAP kinase. MIP-1γ, like RANKL, stimulated NF-κB activity, and the pro-survival activity of RANKL was partially dependent on its ability to induce MIP-1γ. MIP-1γ also stimulated the activation of mature osteoclasts. Thus, in contrast to most survival factors that act in a paracine manner, osteoclasts protect themselves from apoptosis through production of MIP-1γ as an autocrine survival factor.

MIP-1γ is an important factor in the bone microenvironment that regulates osteoclastic bone resorption, and plays a role in both normal bone turnover and in osteolytic diseases. MIP-1γ

MIP-1γ is also referred to herein as Scya9 (small inducible cytokine A9), which corresponds to OC #3 (FIG. 1A).

MIP-1 gamma is closely related to MIP-1 alpha, MIP-1 beta, and C10. It shares a high-affinity receptor with MIP-1 alpha and activates calcium release in neutrophils. Moreover, MIP-1 alpha and MIP-1 gamma are cross-desensitizing, suggesting that they utilize a common signalling pathway. Like MIP-1 alpha, MIP-1 gamma is pyrogenic in mice. However, distinct from other chemokines, MIP-1 gamma is constitutively expressed by many tissues in vivo and circulates at relatively high concentrations in the plasma of normal mice. Presumably, it occupies a large fraction of the receptors available for CC chemokines in the plasma compartment.

```
U49513
>>gi|1234834|gb|U49513.1|MMU49513 Mouse macrophage inflammatory protein-1 gamma
mRNA, complete cds
                                                                    (SEQ ID NO: 3)
>GGGCCAGCTGGGTCTGCCCACTAAGAAGATGAAGCCTTTTCATACTGCCCTCTCCTTCCTCATTCTTACA

>ACTGCTCTTGGAATCTGGGCCCAGATCACACATGCAACAGAGACAAAAGAAGTCCAGAGCAGTCTGAAGG

>CACAGCAAGGGCTTGAAATTGAAATGTTTCACATGGGCTTTCAAGACTCTTCAGATTGCTGCCTGTCCTA
```

```
>TAACTCACGGATTCAGTGTTCAAGATTTATAGGTTATTTTCCCACCAGTGGTGGGTGTACCAGGCCGGGC

>ATCATCTTTATCAGCAAGAGGGGGTTCCAGGTCTGTGCCAACCCCAGTGATCGGAGAGTTCAGAGATGCA

>TTGAAAGATTGGAGAAAAACTCACAACGACGGAGCTACAAACAATAACATTTGCTTTAGAGAAGGGTGTG

>AACTGCCAGCTACTTTCTTTGGTCTTCCCCAGTGACCACCTAAGTGGCTCTAAGTGTTTATTTTTATAGG

>TATATAAACATTTTTTTTTCTGTTTCCACTTTAAAGTGGCATATCTGGCTTTGTCACAGAGGGGAAACT

>TGTCTGTGCCAACCCCAGTCATCTGAAAACTCAGATGCCTGGGAAGGTCTGAAGCTGACCTCAATGACTA

>CACATAATATTTGATTGAGATAAATGGGCAAGGTCTGGAGAGATGGCTTGGTGGTTAAGAGCACCTGCTG

>CTCTTCCAGAGGACCTGGGTTCAATTCCCACTTAGATGGCAGCTCAAACTATCTATAATTCCAATTCCAA

>AGAAAACTGATGCCCTATTTTGCCCCTTTAGTTACTAGTATTTACAGTATTCTTTATAAATTCACCTTGA

>CATGACCATCTTGAGCTACAGCCATCCTAACTGCCTCAGAATCACTCAAGTTCTTCCACTCGGTTTCCCA

>GCGGATTTTAAGTGGATAAACTGTGAGAGTGGTCTGTGGGACTTTGGAATGTGTCTGGTTCTGATAGTCA

>CTTATGGCAACCCAGGTACATTCAACTAGGATGAAATAAATTCTGCCTTAGCCCAGTAGTATGTCTGTGT

>TTGTAAGGACCCAGCTGATTTTCCCACCACCCCTCCATCAGTCCGCCACTAATAAAGTGCATCTATGC

The ORF is nucleotides 29-397.
Mouse macrophage inflammatory protein-1 gamma
protein_id=AAB02198.1/db_xref="GI:1234835"
                                                              (SEQ ID NO: 4)
MKPFHTALSFLILTTALGIWAQTTHATETKEVQSSLKAQQGLEIEMFHMGFQDSSDCCLSYNSRIQCSRFIGYFPTS

GGCTRPGIIFISKRGFQVCANPSDRRVQRCIERLEKNSQPRTYKQ
```

CCR1

This gene encodes a member of the beta chemokine receptor family, which is predicted to be a seven transmembrane protein similar to G protein-coupled receptors. The ligands of this recrptor include macrophage inflammatory protein 1 alpha (MIP-1 alpha), regulated on activation normal T expressed and secreted protein (RANTES), monocyte chemoattractant protein 3 (MCP-3), and myeloid progenitor inhibitory factor-1 (MPIF-1). Chemokines and their receptors mediated signal transduction are critical for the recruitment of effector immune cells to the site of inflammation. Knock-out studies of the mouse homolog suggested the roles of this gene in host protection from inflammatory response, and susceptibility to virus and parasite. This gene and other chemokine receptor genes, including CCR2, CCRL2, CCR3, CCR5 and CCXCR1, are found to form a gene cluster on chromosome 3p.

```
Homo sapiens chemokine (C-C motif) receptor 1 (CCR1), mRNA.
     ACCESSION NM_001295
   (SEQ ID NO:5)
     1 ggcacgagcc cagaaacaaa gacttcacgg acaaagtccc ttggaaccag agagaagccg 61 ggatggaaac tccaaacacc acagaggact atgacacgac cacagagttt gactatgggg 121 atgcaactcc gtgccagaag gtgaacgaga gggcctttgg ggcccaactg ctgcccctc 181 tgtactcctt ggtatttgtc attggcctgg ttggaaacat cctggtggtc ctggtccttg 241 tgcaatacaa gaggctaaaa aacatgacca gcatctacct cctgaacctg gccatttctg 301 acctgctctt cctgttcacg cttcccttct ggatcgacta caagttgaag gatgactggg 361 tttttggtga tgccatgtgt aagatcctct ctgggtttta ttacacaggc ttgtacagcg 421 agatctttt catcatcctg ctgacgattg acaggtacct ggccatcgtc cacgccgtgt 481 ttgccttgcg ggcacggacc gtcacttttg gtgtcatcac cagcatcatc atttgggccc 541 tggccatctt ggcttccatg ccaggcttat acttttccaa gacccaatgg gaattcactc 601 accacacctg cagcottoac tttcctcacg aaagcctacg agagtggaag ctgtttcagg 661 ctctgaaact gaacctcttt gggctggtat tgcctttgtt ggtcatgatc atctgctaca 721 cagggattat aaagattctg ctaagacgac caaatgagaa gaaatccaaa gctgtccgtt 781 tgatttttgt catcatgatc atcttttttc tcttttggac ccctacaat ttgactatac 841 ttatttctgt tttccaagac ttcctgttca cccatgagtg tgagcagagc agacatttgg
```

```
                          -continued
 901 acctggctgt gcaagtgacg gaggtgatcg cctacacgca ctgctgtgtc aacccagtga 961 tctacgcctt cgttggtgag aggttccgga agtacctgcg gcagttgttc cacaggcgtg 1021 tggctgtgca cctggttaaa tggctcccct tcctctccgt ggacaggctg agagggtca 1081 gctccacatc tccctccaca ggggagcatg aactctctgc tgggttctga ctcagaccat 1141 aggaggccaa cccaaaataa gcaggcgtga cctgccaggc acactgagcc agcagcctgg 1201 ctctcccagc caggttctga ctcttggcac agcatggagt cacagccact tgggatagag 1261 agggaatgta atggtggcct ggggcttctg aggcttctgg ggcttcagtc ttttccatga 1321 acttctcccc tggtagaaag aagatgaatg agcaaaacca aatattccag agactgggac 1381 taagtgtacc agagaagggc ttggactcaa gcaagatttc agatttgtga ccattagcat 1441 ttgtcaacaa agtcacccac ttcccactat tgcttgcaca aaccaattaa acccagtagt 1501 ggtgactgtg ggctccattc aaagtgagct cctaagccat gggagacact gatgtatgag 1561 gaatttctgt tcttccatca cctccccccc cccgccaccc tcccactgcc aagaacttgg 1621 aaatagtgat ttccacagtg actccactct gagtcccaga gccaatcagt agccagcatc 1681 tgcctcccct tcactcccac cgcaggattt gggctcttgg aatcctgggg aacatagaac 1741 tcatgacgga agagttgaga cctaacgaga aatagaaatg ggggaactac tgctggcagt 1801 ggaactaaga aagcccttag gaagaatttt tatatccact aaaatcaaac aattcaggga 1861 gtgggctaag cacgggccat atgaataaca tggtgtgctt cttaaaatag ccataaaggg 1921 gagggactca tcatttccat ttacccttct tttctgacta tttttcagaa tctctcttct 1981 tttcaagttg ggtgatatgt tggtagattc taatggcttt attgcagcga ttaataacag 2041 gcaaaaggaa gcagggttgg tttcccttct ttttgttctt catctaagcc ttctggtttt 2101 atgggtcaga gttccgactg ccatcttgga cttgtcagca aaaaaaaaaa aaaaaa
The ORF is nucleotides 63-1130
(SEQ ID NO: 6)
METPNTTEDYDTTTEFDYGDATPC-
QKVNERAFGAQLLPPLYSLVFVIGLVGNILVVLVLVQYKRLKNMTSIYLLNLA

ISDLLFLFTLPFWIDYKLKDDWVFGDAM-
CKILSGFYYTGLYSEIFFIILLTIDRYLAIVHAVFALRARTVTFGVITS

IIIWALAILASMPGLYFSK-
TQWEFTHHTCSLHFPHESLREWKLFQALKLNLFGLVLPLLVMIICYTGIIKILLRRPN

EKKSKAVRLIFVIMIIFFLFWTPYNLTI-
LISVFQDFLFTHECEQSRHLDLAVQVTEVIAYTHCCVNPVIYAFVGERF

RKYLRQLFHRRVAVHLVKWLPFLSVDRLERVSSTSPSTGEHELSAGF
```

MIP-1α

Homo sapiens macrophage inflammatory protein-1-alpha/RANTES receptor mRNA, complete cds.

```
ACCESSION L10918
                                                              (SEQ ID NO: 8)
    1    ggcacgagcc cagaaacaaa gacttcacgg acaaagtccc ttggaaccag agagaagccg 61    ggatggaaac tccaaacacc acagaggact atgacacgac cacagagttt gactatgggg 121    atgcaactcc gtgccagaag gtgaacgaga gggcctttgg ggcccaactg ctgcccctc 181    tgtactcctt ggtatttgtc attggcctgg ttggaaacat cctggtggtc ctggtccttg 241    tgcaatacaa gaggctaaaa aacatgacca gcatctacct cctgaacctg gccatttctg 301    acctgctctc cctgttcacg cttcccttct ggatcgacta caagttgaag gatgactggg 361    tttttggtga tgccatgtgt aagatccctc tgggttttta ttacacaggc ttgtacagcg 421    agatcttttt catcatcctg ctgacgattg acaggtacct ggccatcgtc cacgccgtgt
```

-continued

```
 481  ttgccttgcg  ggcacggacc  gtcactttt g  gtgtcatcac  cagcatcatc  atttgggccc
 541  tggccatctt  ggcttccatg  ccaggcttat  acttttccaa  gacccaatgg  gaattcactc
 601  accacacctg  cagccttcac  tttcctcacg  aaagcctacg  agagtggaag  ctgtttcagg
 661  ctctgaaact  gaacctcttt  gggctggtat  tgcctttgtt  ggtcatgatc  atctgctaca
 721  cagggattat  aaagattctg  ctaagacgac  caaatgagaa  gaaatccaaa  gctgtccgtt
 781  tgattttgt   catcatgatc  atctttttc   tcttttggac  ccctacaat   ttgactatac
 841  ttatttctgt  tttccaagac  ttcctgttca  cccatgagtg  tgagcagagc  agacatttgg
 901  acctggctgt  gcaagtgacg  gaggtgatcg  cctacacgca  ctgctgtgtc  aacccagtga
 961  tctacgcctt  cgttggtgag  aggttccgga  agtacctgcg  gcagttgttc  cacaggcgtg
1021  tggctgtgca  cctggttaaa  tggctcccct  tcctctccgt  ggacaggctg  gagagggtca
1081  gctccacatc  tccctccaca  ggggagcatg  aactctctgc  tgggttctga  ctcagaccat
1141  aggaggccaa  cccaaaataa  gcaggcgtga  cctgccaggc  acactgagcc  agcagcctgg
1201  ctctcccagc  caggttctga  ctcttggcac  agcatggagt  cacagccact  tgggatagag
1261  agggaatgta  atggtggcct  ggggcttctg  aggcttctgg  ggcttcagtc  ttttccatga
1321  acttctcccc  tggtagaaag  aagatgaatg  agcaaaacca  aatattccag  agactgggac
1381  taagtgtacc  agagaagggc  ttggactcaa  gcaagatttc  agatttgtga  ccattagcat
1441  ttgtcaacaa  agtcacccac  ttcccactat  tgcttgcaca  aaccaattaa  acccagtagt
1501  ggtgactgtg  ggctccattc  aaagtgagct  cctaagccat  gggagacact  gatgtatgag
1561  gaatttctgt  tcttccatca  cctccccccc  cccgccaccc  tcccactgcc  aagaacttgg
1621  aaatagtgat  ttccacagtg  actccactct  gagtcccaga  gccaatcagt  agccagcatc
1681  tgcctcccct  tcactcccac  cgcaggattt  gggctcttgg  aatcctgggg  aacatagaac
1741  tcatgacgga  agagttgaga  cctaacgaga  aatagaaatg  ggggaactac  tgctggcagt
1801  ggaactaaga  aagcccttag  gaagaatttt  tatatccact  aaaatcaaac  aattcaggga
1861  gtgggctaag  cacgggccat  atgaataaca  tggtgtgctt  cttaaaatag  ccataaaggg
1921  gagggactca  tcatttccat  ttacccttct  tttctgacta  tttttcagaa  tctctcttct
1981  tttcaagttg  ggtgatatgt  tggtagattc  taatggcttt  attgcagcga  ttaataacag
2041  gcaaaaggaa  gcagggttgg  tttcccttct  ttttgttctt  catctaagcc  ttctggtttt
2101  atgggtcaga  gttccgactg  ccatcttgga  cttgtcagca  aaaaaaaaaa  aaaaaa
```

The ORF is nucleotides 63..1130.
macrophage inflammatory protein-1-alpha; protein_id=AAA36543.1; db_xref=GI:292417
(SEQ ID NO: 8)
METPNTTEDYDTTTEFDYGDATPCQKVNERAFGAQLLPPLYSLVFVIGLVGNILVVLVLVQYKRLKNMTSTYLLNLA

ISDLLFLFTLPFWIDYKLKDDWVFGDAMCKILSGFYYTGLYSEIFFIILLTIDRYLAIVHAVPALRARTVTFGVITS

IIIWALAILASMPGLYFSKTQWEFTHHTCSLHFPHESLREWKLFQALKLNLFGLVLPLLVMIICYTOTIKILLRRPN

EKKSKAVRLTFVIMIIFFLFWTPYNLTILISVFQDFLFTHECEQSRHLDLAVQVTEVIAYTHCCVNPVIYAFVGERF

RKYLRQLFHRRVAVHLVKWLPFLSVDRLERVSSTSPSTGEHELSAGF

Rantes

RAMTES (the acronym for "Regulated upon Activation, Normal T-cell Expressed and Secreted") is a small chemotactic protein that mediates many immunological, allergic, and inflammatory responses. RANTES is rapidly up-regulated in response to a variety of stimuli and, once secreted, it recruits monocytes, eosinophils, and basophils to the inflammation site. RANTES has been implicated in both acute and chronic phases of inflammation associated with pathological conditions such as asthma, autoimmune diseases, transplant reject, cancer and AIDS.

The human RANTES gene maps to chromosome 17q11.2-q12 and spans approximately 7.1 kb. The mRNA transcribed from the RANTES gene is 1.2 kb long. It encodes a 10 kD protein, including a cleavable amino-terminal signal sequence of 23 amino acids. The secreted protein is 68 amino acids long with a predicted mass of approximately 8 kD.

```
Homo sapiens RANTES precursor, mRNA, complete cds.
ACCESSION AF043341
                                                                    (SEQ ID NO:9)
    1    accatgaagg  tctccgcggc  agccctcgct  gtcatcctca  ttgctactgc  cctctgcgct 61    cctgcatctg  cctccccata  ttcctcggac  accacaccct  gctgctttgc  ctacattgcc 121    cgcccactgc  cccgtgccca  catcaaggag  tatttctaca  ccagtggcaa  gtgctccaac 181    ccagcagtcg  tctttgtcac  ccgaagaac   cgccaagtgt  gtgccaaccc  agagaagaaa 241    tgggttcggg  agtacatcaa  ctctttggag  atgagctagg  atggagagtc  cttgaacctg 301    aacttacac
The ORF is nucleotides 4-279.
protein_id=AAC03541.1; db_xref="GI:2905632"
                                                                    (SEQ ID NO:10)
MKVSAAALAVILIATALCAPASASPYSSDTTPCCFAYIARPLPRAHIKEYFYTSGKCSNPAVVFVTRKNRQVCANPE
KKWVREYINSLEMS
```

Terminal Differentiation of Osteoclasts is Regulated by the Brn3 Transcription Factors The differentiation of pre-osteoclasts to mature osteoclasts following RANKL stimulation involves early activation of the transcription factors NF-κB and AP-1. Additional transcription factors are required for terminal differentiation and bone resorptive function (e.g. MITF)

Through screening arrays of transcription factor activity, we found that Brn3 family members are activated in osteoclast precursor cells in response to RANKL stimulation. Brn3 POU-domain transcription factors have been shown to be crucial in regulating differentiation and maturation of neuronal cells. There are three related proteins, Brn3a, Brn3b, and Brn3c (also known as Pou4f1, Pou4f2, Pou4f3) that are derived from distinct genes. Brn3 proteins share more than 95% identity within a bipartite DNA-binding POU domain, which consists of two highly conserved regions, connected by a variable linker of 14-26 amino acids. DNA binding site is ACTCATTAAT (SEQ ID NO:11), ACTCATTAAC (SEQ ID NO:12), GCTCATTAAT (SEQ ID NO:13), or GCTCATTAAC (SEQ ID NO:14) and similar sequences that are recognized by each of the Brn3 POU domains. Other Brn3 binding sites or target sequences include CACAGCTCATTAACGCGC (SEQ ID NO:44), CACTCCTCATTAACGCGC (SEQ ID NO:45), CACAGCTCATTAAGTCGC (SEQ ID NO:46), or CACGCATGCGTAATGCGC (SEQ ID NO:47). A general POU domain recognition site is GCATNNNTAAT (SEQ ID NO:48), where N represents any base pair. For the Brn3 protein class, high-affinity binding requires that N=3. Brn3 transcription factors can regulate specific target genes through interactions with these sites. The Brn3 class of proteins have been shown to bind with high affinity to a recognition element derived from the rat corticotropin-releasing hormone (CRH) gene promoter, GCATAAATAAT (SEQ ID NO:49).

The human Brn3 POU domains are amino acids 270-418 in Brn3a, amino acids 257-405 in Brn3b, and amino acids 185-333 in Brn3c. The human Brn3 upstream homology domains are amino acids 44-70 in Brn3a, amino acids 98-123 in Brn3b, and amino acids 43-68 in Brn3c.

Brn3 family members are expressed mainly in neurons in the trigeminal and dorsal root ganglia, in retinal ganglion cells, in cochlear hair cells and in several brainstem nuclei, both during development and in adulthood, but have not previously been identified in bone.

The expression and activation of Brn3 family members during RANKL-induced osteoclast development and activation was examined. An increase in brn3a, brn3b, and brn3c expression was measured in response to RANKL stimulation of osteoclast precursor cells. In addition, DNA binding activity of Brn3a and Brn3b reached a maximum parallel to the appearance of first osteoclastic giant cells. Functional inhibition of Brn3 DNA-binding activity using decoy oligonucleotides containing a Brn3 consensus site resulted in an inhibition of pre-osteoclast fusion, and a reduction in the bone resorption activity of mature osteoclasts. Targeted deletion of brn3b in mice caused altered bone structure with increased bone mass. Thus, Brn3 transcription factors are important regulators of the terminal differentiation of osteoclasts that are targets for treatment of bone diseases.

Screening of Transcriptional Activation in Osteoclast Differentiation

Incubation of RAW 264.7 cells with RANKL, an art recognized model for osteoclast differentiation/function, for 5 days resulted in the formation of multinucleated osteoclast-like cells. As previously shown, these cells express the osteoclast-specific markers tartrate resistant acid phosphatase (TRAP), cathepsin K, matrix metalloproteinase-9 (MMP-9), the proton pump protein Atp6i, and form resorption pits on bone slices and sub-micron calcium phosphate films.

Figure 10A:
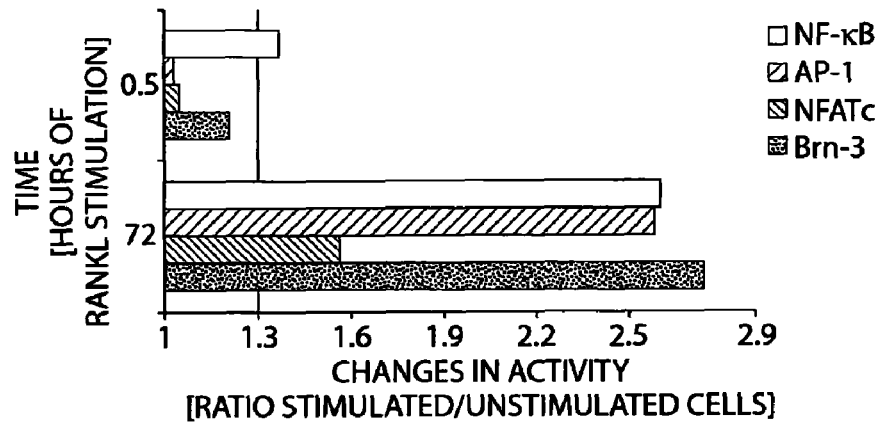
FIGS. 10A-10D are bar graphs (A-C) and an autoradiograph (D) showing RANKL-induced transcriptional activation in osteoclast differentiation. A, Transcriptional screening analysis performed on macrophage-like RAW264.7 cells at 30 min and 3 days after RANKL stimulation showed a time-dependant activation of Brn3. The screening system was evaluated by the activation profiles of the transcription factors NF-κB, AP-1 and NFATc known to be activated in osteoclastogenesis. Activation ratios above 1.3 were considered as an increase in transcriptional activity compared to unstimulated cells. B, Time course of RANKL induced Brn3/DNA-binding activity; combined results of three separate experiments. *p<0.01, compared to non-stimulated cells. C, Supershift experiments showed the presence of Brn3a and Brn3b in the Brn3/DNA binding complex. A specific antibody was not available for Brn3c. Combined results of three separate experiments. *p<0.05, compared to day 4 nuclear extract.

A transcriptional screening analysis was performed on RAW 264.7 cells after RANKL stimulation using the Tran-Signal Screen (Panomics, Calif.). The differential activation of 54 different transcription factor binding sites was explored over a time course of 3 days and compared to non-stimulated cells. This analysis revealed a specific time-dependent activity of Brn3 transcription factors, which increased significantly on day 3 (FIG. 10A). In addition, NF-κB transcriptional activity increased after 30 min, and AP-1 and NFATc showed a delayed increase of binding activity in response to RANKL stimulation, consistent with previous findings of other investigations.

Figure 10B:
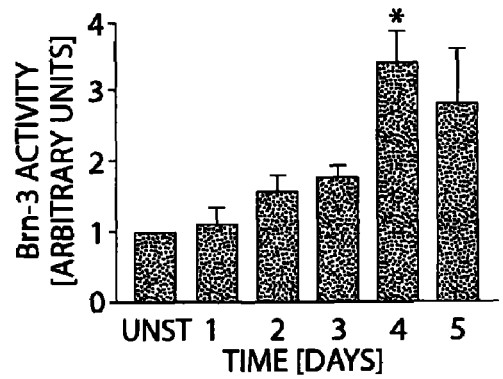
Figure 10C:
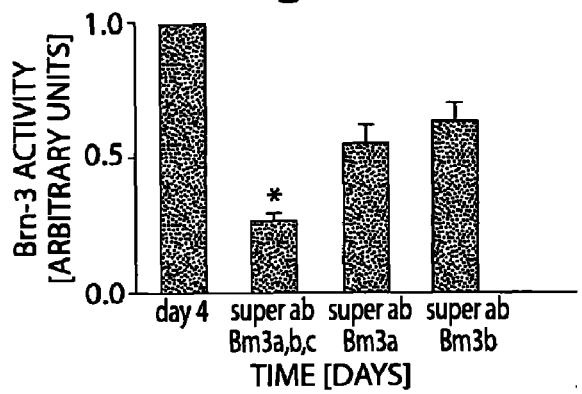
Figure 10D:
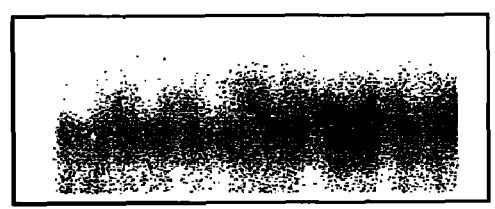
Figure 11A:
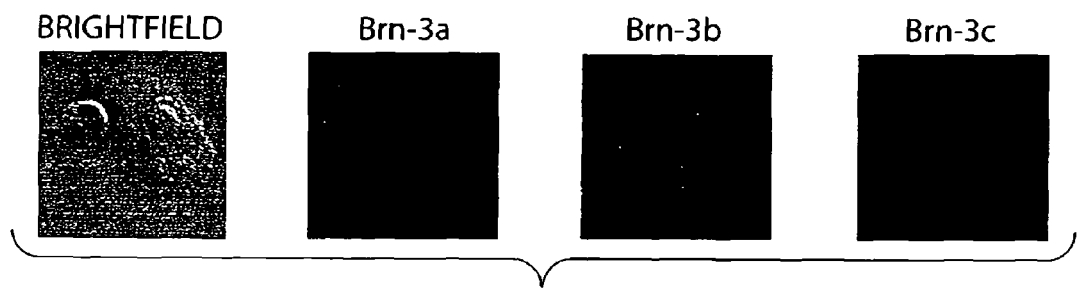
FIGS. 11A-11D are a series of photographs (A), a line graph (B), and bar graphs (C and D) showing the induction of Brn3 gene and protein expression during osteoclast differentiation. A, Immunofluorescence staining illustrates nuclear and cytoplasmic localization of Brn3a, Brn3b and Brn3c in RAW264.7-derived osteoclasts after 4 days in culture. B, Expression of brn3a, brn3b and brn3c mRNA increases in response to RANKL stimulation of RAW264.7 cells. *p<0.05 vs. baseline. C, Brn3a and Brn3b Western blot analysis revealed an increase in protein levels after stimulation with RANKL. Combined results of three separate experiments. *p<0.05 vs. baseline.

To verify these results and identify the involved Brn3 transcription factors, EMSA analysis was performed using specific Brn3 consensus oligonucleotides. These experiments demonstrated a selective activation of the Brn3/DNA binding complex beginning on day 1, and peaking at day 4 after RANKL stimulation (FIG. 10B). Supershift experiments revealed the presence of two related POU family members Brn3a and Brn3b in the Brn-3/DNA binding complexes (FIG. 10C). In addition, immunohistochemical analysis by confocal microscopy demonstrated both nuclear and cytoplasmic localization of Brn3 proteins a, b, and c in RAW264.7 cells that were stimulated with RANKL for 4 days (FIG. 11A).

Induction of Brn3 Gene and Protein Expression

Figure 11B:
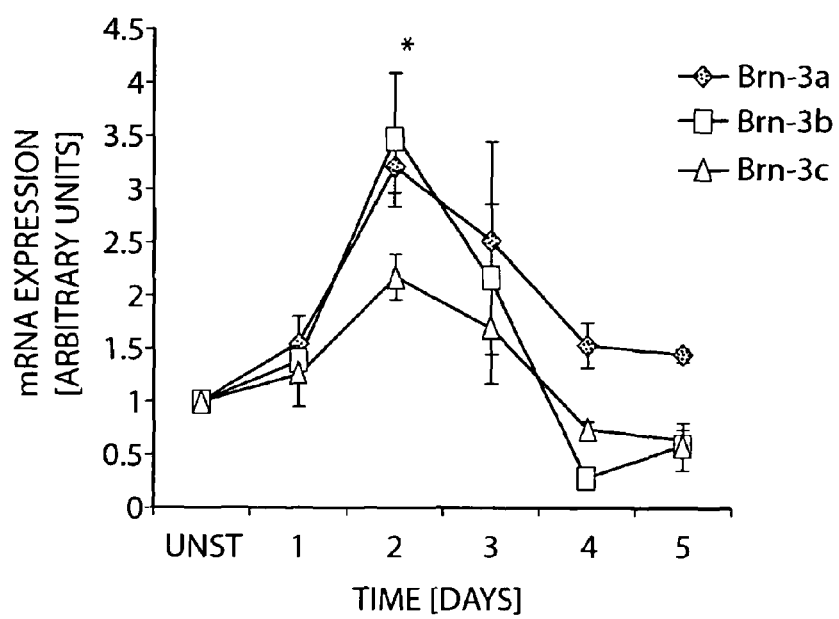
Figure 11C:
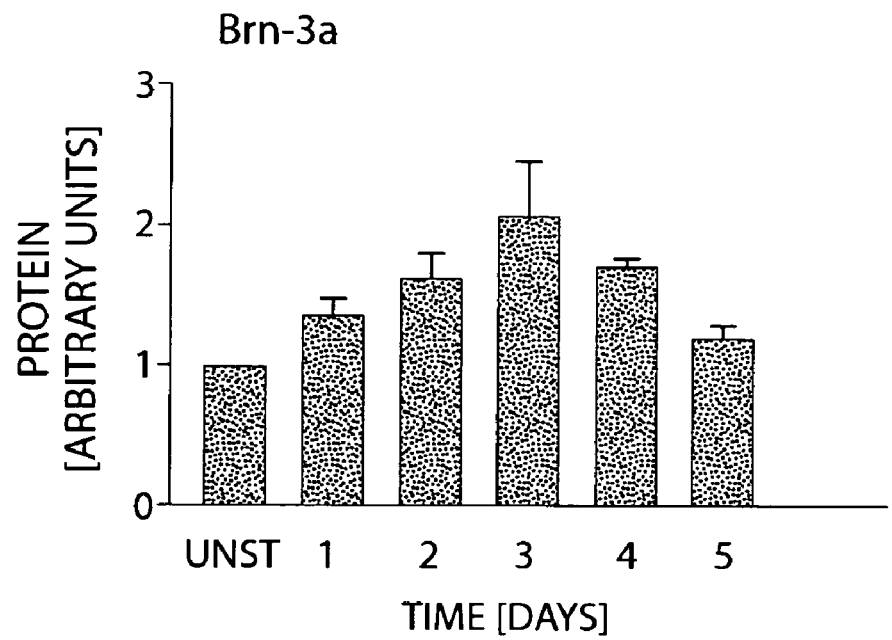
Figure 11D:
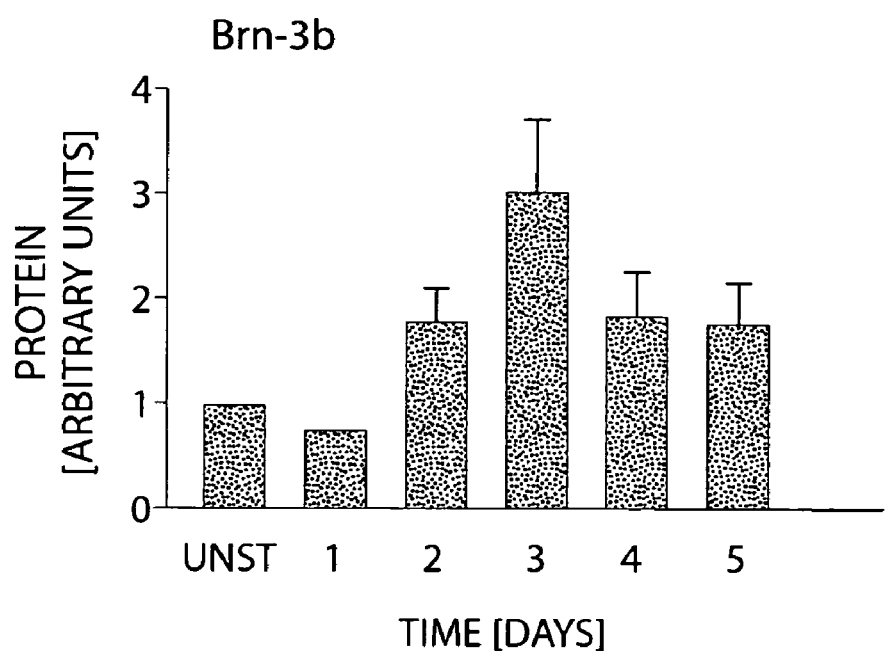

Using semi-quantitative RT-PCR, a strong increase in expression of Brn3b and Brn3a mRNA was measured, along with a modest increase in Brn3c expression level that peaked on day 2 after RANKL stimulation (FIG. 11B). Western blot analysis revealed a delayed increase in protein levels that peaked on day 3, with Brn3b showing higher expression than Brn3a (FIG. 11C). Brn3 proteins are induced in response to RANKL stimulation and that Brn3b is the major POU4 family member expressed in developing osteoclasts.

Effect of Inhibition of Brn3 Transcriptional Activity by Decoy Oligonucleotides

Figure 12A:
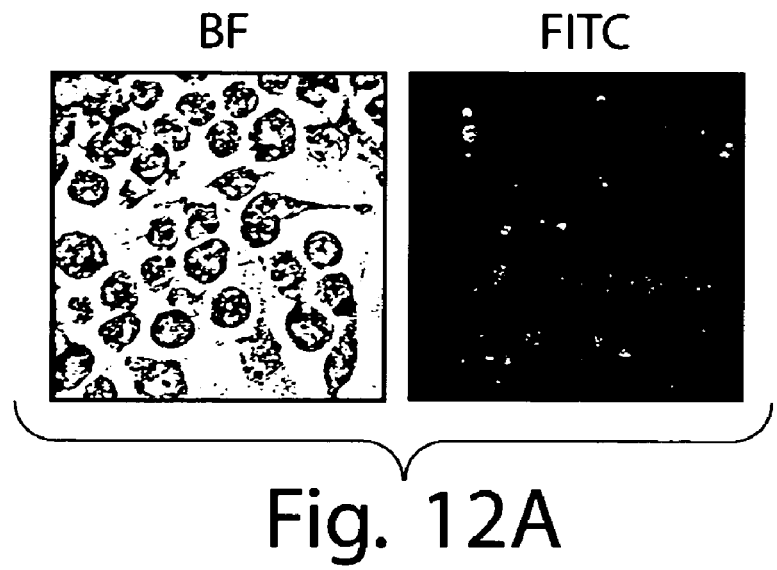
FIGS. 12A-12E are a series of photographs (A), bar graphs (B and E), an autoradiograph (C), and a photograph of a gel (D) showing the functional inhibition of transcriptional activity by Brn3 decoy oligonucleotides. A, FITC labeled decoy and mutant oligonucleotides as a control were transfected into cells, and transfection efficiency was monitored by fluorescence microscopy (FITC). BF: brightfield. B, Decoy oligonucleotides almost completely abolished RANKL-induced Brn3 binding activity in nuclear extracts, compared to mutant transfected control cells. C, RANKL stimulated expression of the Brn3 target gene synaptotagrnin 1 (Syt 1) was inhibited by functional blockade of Brn3. *p<0.05 vs. mutant transfected cells.
Figure 12B:
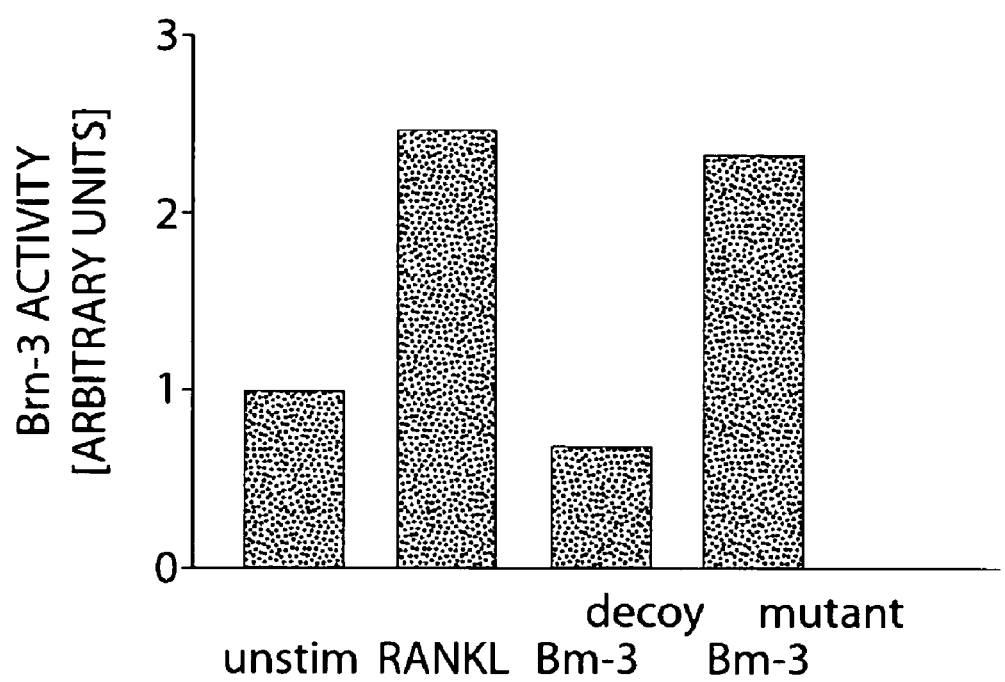

Decoy oligonucleotides that contain a consensus binding site which is recognized by each of the Brn3 POU domain factors were used to inhibit the transcription activity of Brn3 proteins. The transfection efficiency of FITC-labeled decoy oligonucleotides was approximately 80% as assessed by fluorescence microscopy (FIG. 12A). Transfected cells were extracted for their content of nuclear proteins and the residual Brn3 transcriptional activity was analyzed by EMSA. As seen in FIG. 12B, Brn3 activity was reduced by approximately 70% compared to non-transfected cells or cells transfected with mutant oligonucleotides.

Figure 12C:
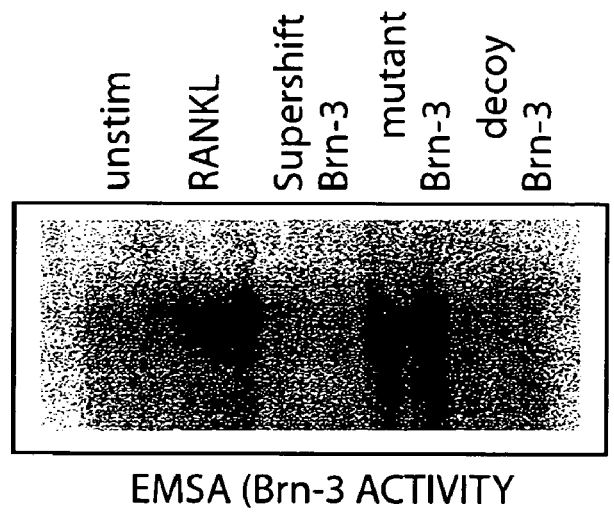
Figure 12D:
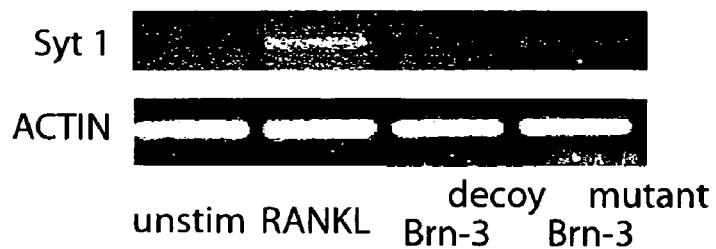
Figure 12E:
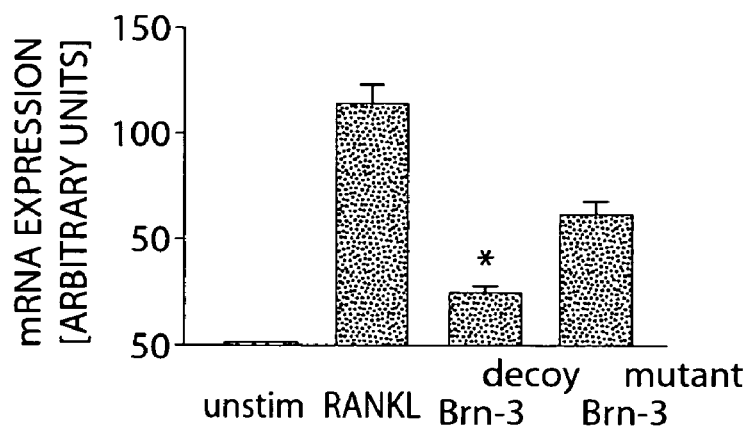

Decoy oligonucleotides in RANKL-stimulated RAW264.7 cells were used to examine the expression of synaptotagmin-1 (Syt1), a known Brn3 regulated gene. As shown in FIG. 12C, Brn3 decoy oligonucleotides reduced Syt1 expression by 60% compared to control cells transfected with mutant Brn3 oligonucleotides. These data indicate that the transfection of RAW 264.7 cells with Brn3 decoy oligonucleotides results in a specific inhibition of the activity of these transcription factors in vitro.

Reduction of Osteoclast Fusion by Inhibition of Brn3 Transcriptional Activity

Figure 13A:
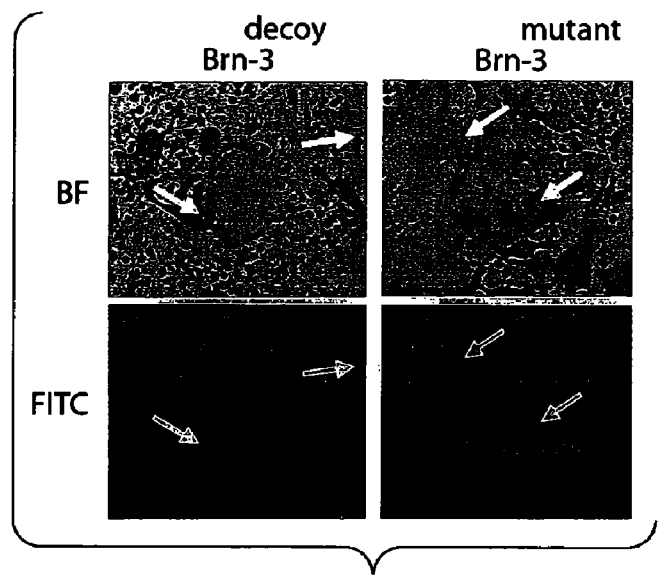
FIGS. 13A-13C are a series of photographs (A), a line graph (B), and a bar graph (C) showing the reduction of giant cell formation by functional inhibition of Brn3. A, Brightfield (BF) and fluorescence microscopy (FITC) of RANKL-induced RAW264.7 cells transfected with FITC-labeled oligonucleotides. As indicated by arrows, FITC-labeled Brn3 mutant oligonucleotides transfected into cell nuclei did not interfere with giant cell formation. In the Brn3 decoy oligonucleotide culture, multinucleated giant cells appear almost non-transfected compared to cells that integrated Brn3 decoy oligonucleotides and therefore remained smaller and less differentiated. B, Functional inhibition of Brn3 by using decoy oligonucleotides resulted in a 40% reduction of giant cell formation assessed by total osteoclast surface area. *p<0.05 vs. mutant transfected cells. C, Effect of functional inhibition of Brn3 on multinuclearity of osteoclasts. *p<0.05 vs. mutant transfected cells.
Figure 13B:
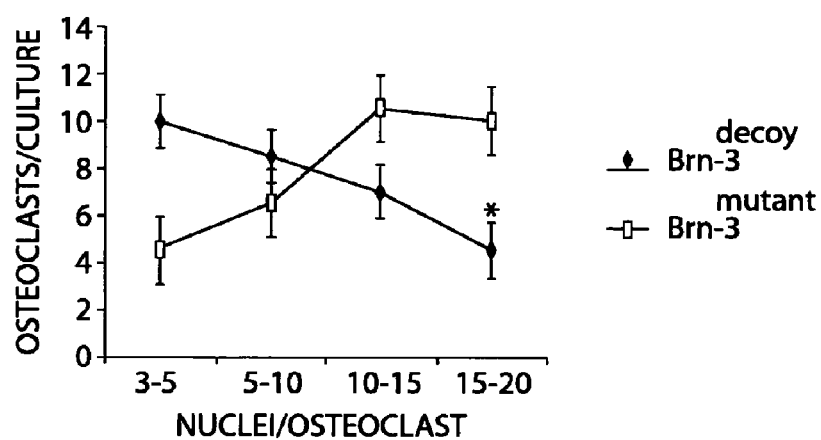
Figure 13C:
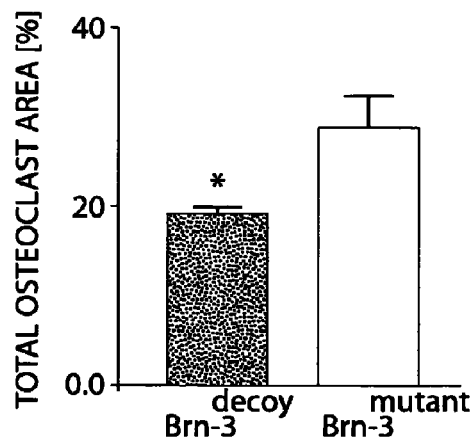

The effects of selective inhibition of Brn3 transcriptional activity on osteoclast formation was investigated. Cells were stimulated with RANKL, transfected on day 2, and monitored daily for RANKL-induced formation of osteoclastic giant cells from RAW264.7 cells. Transfection of Brn3 decoy oligonucleotides resulted in similar total numbers of TRAP+ osteoclasts. However, cell fusion was inhibited by up to 40% on day 5 compared to controls, as assessed by total osteoclast surface area (FIG. 13A). FITC-labeled Brn3 mutant oligonucleotides were incorporated into cell nuclei without affecting cell fusion and differentiation. In contrast, those multinucleated cells that did form in the Brn3 decoy oligonucleotide cultures were consistently non-transfected, whereas cells that integrated Brn3 decoy oligonucleotides remained smaller and less differentiated (FIG. 13A). Further analysis of multinucleated cells also demonstrated a significant reduction in the number of nuclei per cell due to inhibition of Brn3 by decoy oligonucleotides vs. cells transfected with Brn3 mutant oligonucleotides (FIG. 13B). However, there was no reduction in the expression of either TRAP or cathepsin K by decoy oligonucleotides as assessed by Northern analysis. These results indicate that Brn3 proteins regulate very late events in osteoclast differentiation, in particular terminal cell fusion processes, but do not affect earlier gene expression.

Effect of Functional Inhibition of Brn3 on Osteoclast Bone Resorptive Activity

Figure 14A:
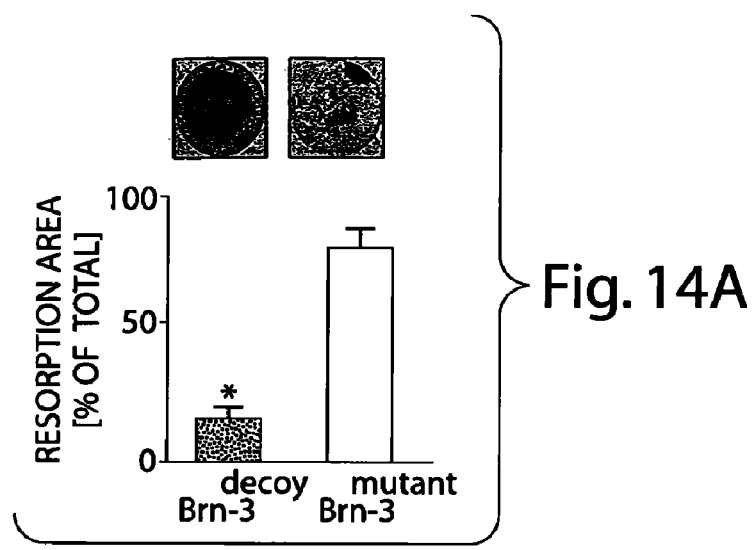
FIGS. 14A-14C are bar graphs with accompanying photographs showing that the functional inhibition of Brn3 reduces osteoclast resorptive activity. A, RANKL-induced osteoclastic resorption activity is diminished in differentiated RAW264.7 cells transfected with decoy oligonucleotides. Resorption was assessed on submicron calcium phosphate slides. *p<0.01 vs. mutant transfected cells. B, RANKL-induced osteoclasts derived from normal bone marrow cells. C, RANKL-induced osteoclasts derived from RAW264.7 cells exhibited greater than 80% reduction in pit formation on bovine bone slides by functional inhibition of Brn3; scanning electron microscopy. *p<0.05 vs. mutant transfected cells.
Figure 14B:
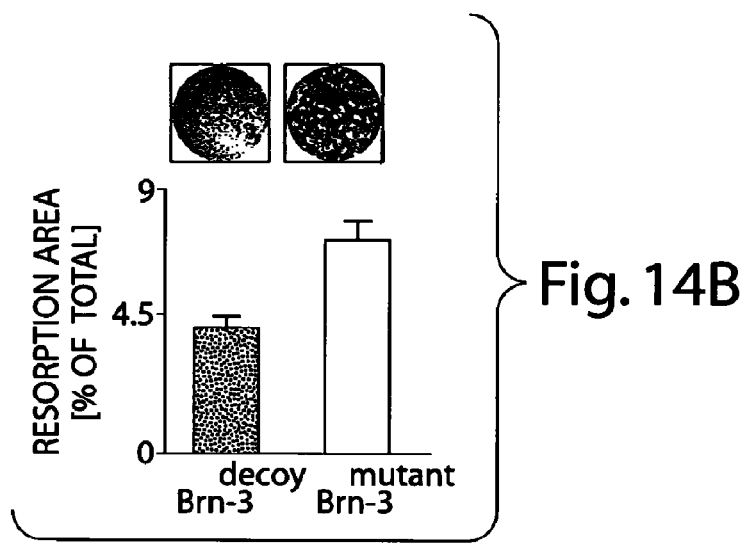
Figure 14C:
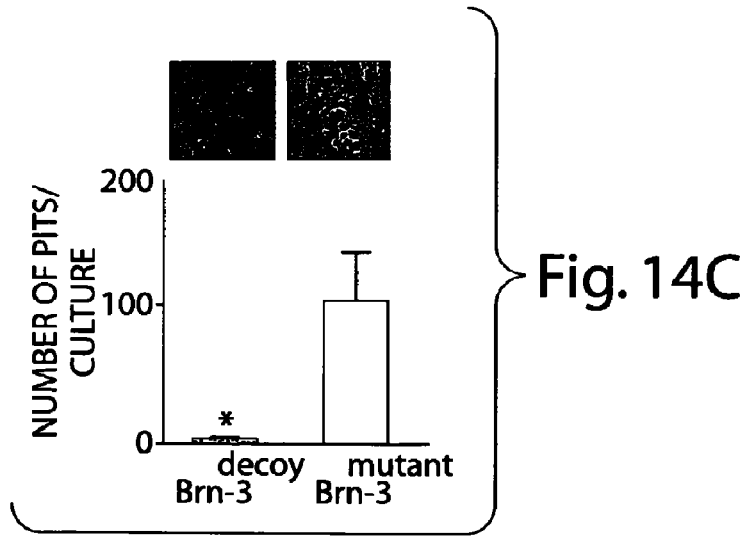

The impact of Brn3 on RANKL induced osteoclast resorptive activity was also analyzed. Differentiated RAW264.7 cells, seeded onto Osteologic™ slides and transfected with decoy oligonucleotides, exhibited 80% reduction of resorption activity in the decoy transfected cells compared to mutant oligonucleotide controls (FIG. 14A). This result was confirmed using bovine bone slides. Functional inhibition of Brn3 by decoy oligonucleotides resulted in more than 80% reduction of the number of resorption pits compared to mutant control transfected cells (FIG. 14C). Osteoclasts were generated by co-culture of bone marrow cells with calvarial cells in the presence of $10^{-8}$M $1\alpha$, $25$-$(OH)_2D_3$ for 7 days. After transfer of osteoclasts to Osteologic™ slides, cells were transfected with decoy or mutant oligonucleotides to block Brn3 activity. Similar to findings with RAW264.7 cells, a 41% reduction in osteoclastic resorption activity was seen following functional inhibition of Brn3 (FIG. 14B). Thus, the Brn3 family are important factors in terminal stages of osteoclast differentiation and activation processes in response to RANKL stimulation.

Effect of Brn3 Gene Deletion on Bone Mass and Micro-Architecture

Figure 15A:
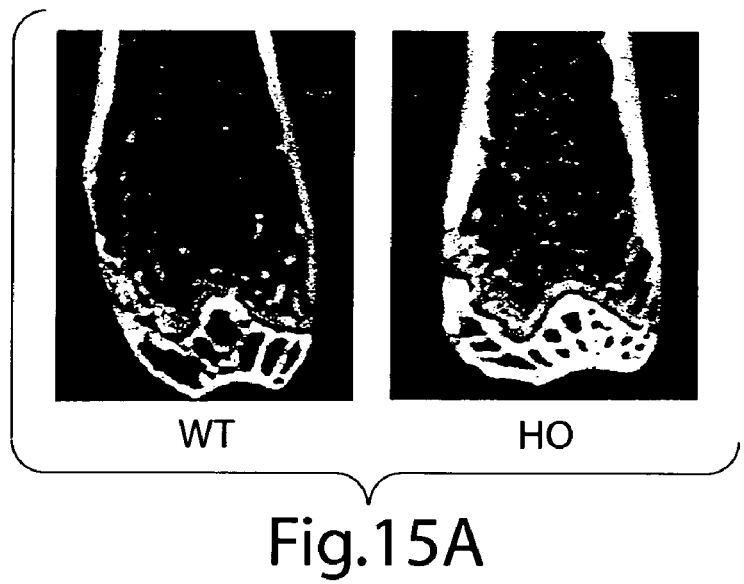
FIGS. 15A-15H are a series of photographs (A) and bar graphs (B-H) showing that Brn3b gene deletion results in increased bone mass and altered bone micro-architecture in vivo. A, Representative micro-CT sections of femurs from wild type (WT) and homozygous Brn3b knockout mice (HO). B, Bone mineral density of wild type, heterozygous (HE) and homozygous knockouts was determined by densitometry. C-H: Micro-CT derived parameters of femurs in WT, HE and HO mice. C, apparent bone volume; D, cortical percent bone volume; E, cortical thickness; F, cortical percent marrow volume; G, trabecular separation; H, trabecular number. **p<0.01, *p<0.05.
Figure 15B:
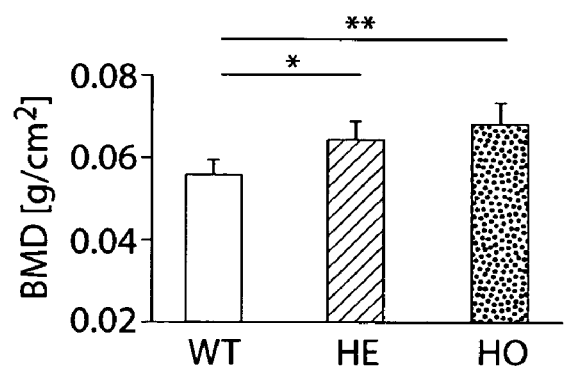
Figure 15C:
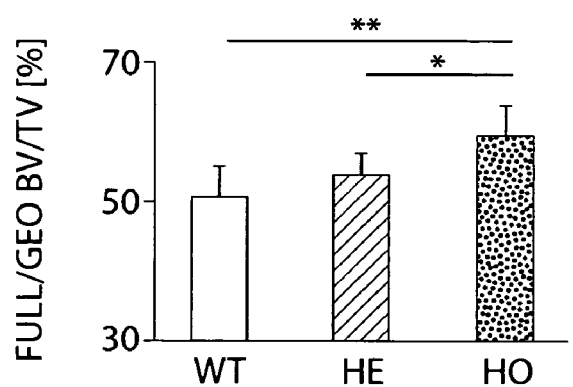
Figure 15D:
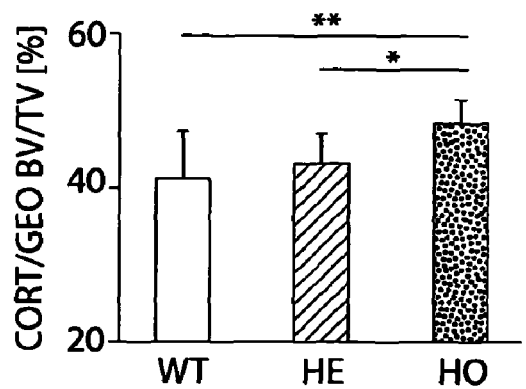
Figure 15E:
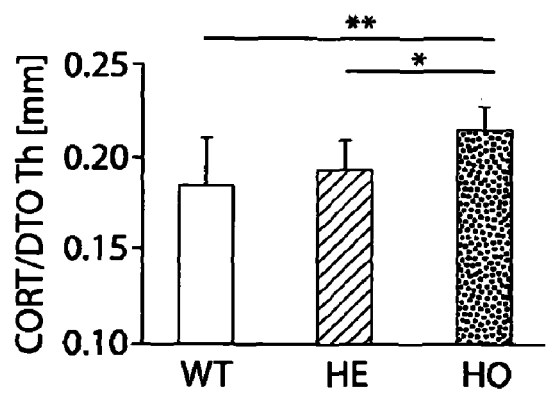
Figure 15F:
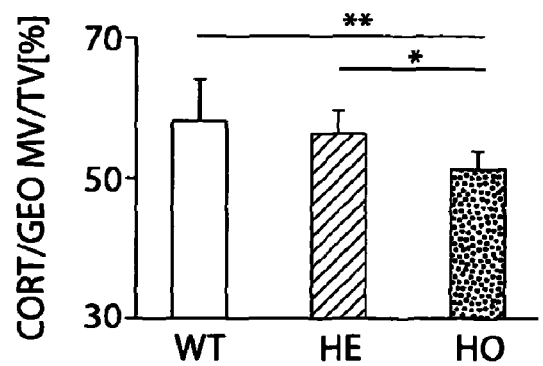
Figure 15G:
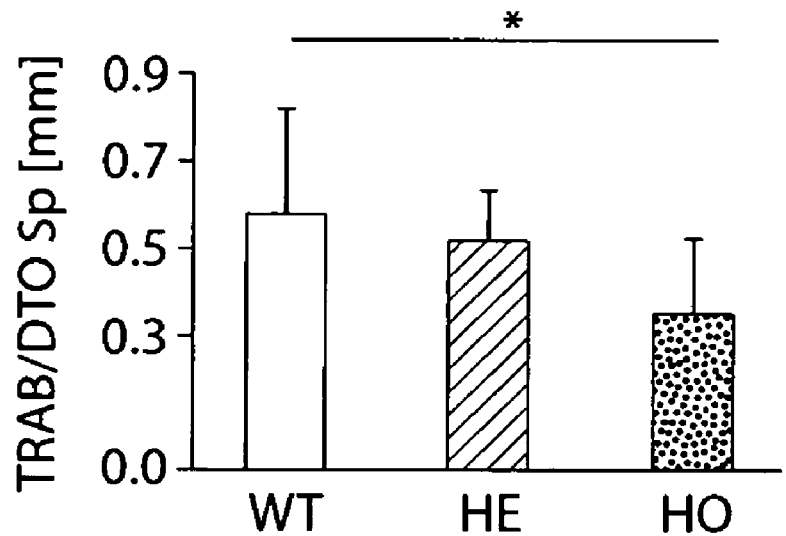
Figure 15H:
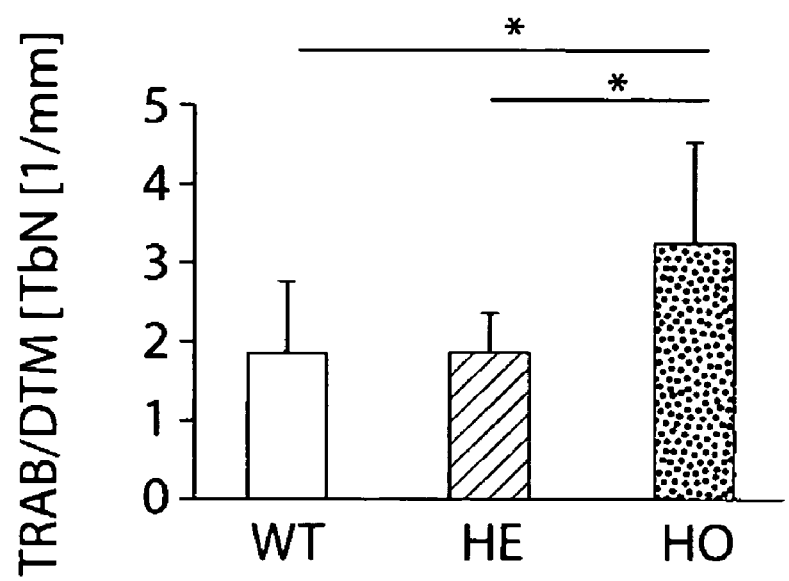

Brn3b null mice are viable but exhibit severe damage in retinal cells, whereas Brn3a mice die shortly after birth. Therefore, the bone phenotype of $Brn3b^{+/+}$, $^{+/-}$ and $^{-/-}$ mice was determined by DEXA. Consistent with the in vitro findings, total bone mineral density was higher in the homozygous and heterozygous mice than in wildtype controls (FIG. 15B). To further investigate the effect of brn3b deletion on trabecular and cortical bone, femurs were analyzed by microcomputed tomography (FIG. 15A). As shown in FIG. 15C, Brn3b null mice showed an increased bone volume fraction of the femur compared to both heterozygous and wildtype mice, confirming the DEXA findings. Analyses of cortical and trabecular bone in the midshaft region of the femur demonstrated higher cortical bone volume (FIG. 15D), increased cortical thickness (FIG. 15E), and a smaller bone marrow cavity (FIG. 15F) in the Brn3b null mice compared to controls. In addition, trabeculae in Brn3b null mice showed less separation (FIG. 15G) and a higher trabecular number. Therefore, Brn3b has an important role in maintenance of bone mass, likely via effects on osteoclast differentiation.

Induction and Activation of Brn3 Proteins by RANKL

The mature, multinucleated osteoclast derives from the monocyte/macrophage lineage in a differentiation process that ultimately involves the fusion of precursor cells to form multinucleated giant cells. As a mandatory inducing factor, RANKL activates osteoclast precursors to develop into bone resorbing cells. Differentiation results in profound morphological changes accompanied by a restricted gene expression pattern. The regulation of osteoclast differentiation is driven by a complex network of transcription factors, which includes NF-κB, AP-1, NFATc, E-box factor MITF and others.

To systematically analyze the transcriptional regulation of macrophage-like cells undergoing osteoclast differentiation an activated transcription factor array approach was used. One of the most prominently bound consensus binding sites was occupied by activated Brn3 POU domain factors. Analysis in more detail revealed a continually increasing activity of Brn3a and Brn3b peaking at day 4 in vitro, concurrent with detection of the first fused multinucleated osteoclasts. Since all the Brn3 proteins (a, b, c) have very similar DNA recognition and binding properties, a decoy oligonucleotide approach was chosen which was able to simultaneously inhibit the transcriptional activity of all three family members. The data clearly established that inhibition of Brn-3 proteins reduces osteoclast formation, fusion and activation in vitro. In vivo, Brn3b null mice had higher bone mass with increased cortical and trabecular bone.

Brn3 transcription factors were first described in neuronal differentiation, in which there is a clearly distinctive but overlapping pattern of brn3a, brn3b, brn3c gene expression, as well as in some non-neuronal cells such as in testis during germ cell development. The phenotypes exhibited by Brn3 null mice reflect the temporal expression patterns of the three POU4 transcription factors. In dorsal root and trigeminal ganglia, brn3a is the first of the Brn3 family members that is expressed. Brn3a gene deletion in vivo causes impairment of somatosensory and motor control in large part secondary to selective neuronal destruction in these regions. Brn3b is the first brn3 gene to be detected in the developing retina followed by brn3a and brn3c expression. Brn3b null mice show severe defects in the retina and are missing about 70% of their retinal ganglion cells. In cochlear and vestibular hair cells of the inner ear, brn3c is first expressed, and brn3c absence leads to hair cells degeneration with a secondary loss of spiral and vestibular ganglion neurons.

Studies in chick ganglion cells indicate a functional redundancy of the Brn3 family members, since all showed a similar ability to promote cell differentiation and development when ectopically expressed in retinal progenitor cells. Brn3a and Brn3b could both function as transcriptional activators with no observed inhibitory effect of Brn3b on the transactivation activity of Brn3a, in contrast to earlier studies that described antagonistic effects of these factors. In addition, Brn3b/3c double knockout mice exhibit even more severe retinal ganglion cell defects, also indicative of a partial functional redundancy. In osteoclast precursor cells nearly equal brn3a and brn3b expression was seen in response to RANKL-stimulation, with less brn3c expression. However, a specific effect of brn3b deletion in vivo on bone structure and mass suggests a predominant role for Brn3b since its related family proteins Brn3a and Brn3c do not compensate its function. This is also consistent with findings that Brn3b can activate brn3a and Brn3a can regulate itself.

Brn3 is Essential for Terminal Osteoclast Differentiation and Bone Resorptive Activity The functional effect of Brn3 transcription factors on osteoclast differentiation was investigated by transfecting decoy oligonucleotides into cells, which causes a suppression of Brn3 DNA binding activity. Functional inhibition of Brn3 factors resulted in a reduction of macrophage-derived multinucleated giant cell formation. The cells underwent morphological changes toward mature osteoclasts and expressed normal levels of TRAP and cathepsin K, but demonstrated a significant reduction in multinuclearity. This finding, along with the kinetics of Brn3 DNA binding activity, indicates an involvement of Brn3 proteins in late differentiation including terminal cell fusion processes. In addition, functional inhibition of Brn3 factors in differentiated macrophage-like RAW264.7 cells and in osteoclasts derived from co-cultured bone marrow cells decreased their bone resorptive activity dramatically.

Thus, it appears that Brn3 factors are downstream of NF-κB and AP-1, as well as another RANKL-induced intermediate-late transcription factor, MITF. In contrast to Brn3, MITF deficiency results in reduced expression of both TRAP and cathepsin K. Computer-based promoter analysis of the brn3 family genes indicates the presence of several E-boxes (MITF/TFE3 responsive sites) in addition to multiple NF-κB binding sites. The phenotypic changes observed following inhibition of Brn3 proteins are consistent with effects on the cytoskeleton. Terminal differentiation and resorptive activity are reduced, the latter of which is highly dependent on the establishment of cell polarity with a change of internal cytoskeletal structures. Similarly, in retinal cells, studies of Brn3b null mice indicate that Brn3b is essential for controlling genes whose products are required for the organization of the cytoskeleton, normal cell polarity and axon outgrowth. Therefore, Brn3b is not required for the initial commitment of retinal ganglion cell fate, but without it the terminal differentiation and the formation of axons is disturbed. Similar effects of gene deletion on cell development were found in Brn3c null mice which show an initial generation and differentiation of hair cells but fail to fully develop to form stereociliar bundles. Forced expression of Brn3a in vitro led to outgrowth of mature neuronal processes under conditions when this would normally not occur.

Targeted Deletion of Brn3b Results in Impaired Bone Micro Architecture

Brn3b knockout mice exhibited increased total bone mineral density and bone volume fraction. Micro-architectural changes included thicker cortical bone, a higher number of trabeculae with decreased spacing, and a smaller bone marrow cavity. Since bone development and remodeling require fully functioning osteoclasts, Brn3b deletion results in an osteopetrosis-like syndrome, which, however, is milder than that induced by deletion of other RANKL-induced factors such as NF-κB and AP-1.

The activation of Brn3 transcription factors is enhanced in RANKL-induced osteoclast differentiation and the inhibition of Brn3 proteins results in a suppression of giant cell formation and a reduction in osteoclast resorptive activity. The Brn3 transcription factors are new targets for the modulation of bone mass, and the treatment of bone diseases caused by excessive bone resorption.

Cell Culture

Mouse macrophage-like RAW 264.7 cells (ATCC, Manassas, Va.) were cultured in DMEM supplemented with 1.5 g/l sodium bicarbonate and 10% fetal bovine serum (FBS, Invitrogen, Calif.). To induce osteoclast differentiation, recombinant mouse RANKL (R&D Systems, Minneapolis, Minn.) was added at a concentration of 10 ng/ml. In some experiments, normal mouse bone marrow cells were obtained from the femurs of four week old BALB/c mice, and were cocultured with calvarial cells isolated from 1-2 day old newborn mice for 10 days in αMEM/10% FBS supplemented with $10^{-8}$ M 1α, 25-$(OH)_2$D3 (Biomol, Plymouth Meeting, Pa.) to induce osteoclast formation.

Preparation of Nuclear Extracts

Cells were washed twice with PBS, pH 7.4, followed by suspension in 800 μl ice-cold lysis buffer (mmol/l: HEPES 10; KCl 10; EDTA 0.1; EGTA 0.1; DTT 1.0; PMSF 1.0; aprotinin 10 μg/ml, pepstatin 10 μg/ml, leupeptin 10 μg/ml). The collected samples were incubated on ice for 30 min, vortexed for 30 sec after addition of 50 μl 10% Nonidet-P40, and centrifuged for 10 min at 4° C. The nuclei-containing pellets were suspended in ice-cold buffer (mmol/l: HEPES 20; NaCl 400; EDTA 1.0; EGTA 1.0; DTT 1.0; PMSF 1.0; aprotinin 10 μg/ml, pepstatin 10 μg/ml; leupeptin 10 μg/ml), incubated on ice for 2 h with frequent mixing, and centrifuged for 10 min at 4° C. The supernatants were collected as nuclear extract and stored at −70° C. The total protein concentration was determined using a protein assay kit (Pierce, Rockford, Ill.).

Screening of Transcriptional Activation

Nuclear extracts of cells at different times after RANKL stimulation (baseline, 30 min and 72 h) were incubated with biotin-labeled DNA-binding oligonucleotides (Panomics, Redwood City, Calif.). The protein/DNA complexes were separated from the free unbound probe by loading onto a 2% agarose gel in TBE buffer (M/l: TRIS1, boric acid 0.9, EDTA 0.01). After extraction of the protein/DNA complexes from the gel, the oligonucleotides were isolated following heating of the sample to 95° C. for 3 min. The collected probes were hybridized overnight to a TranSignal Array membrane (Panomics) containing the consensus binding sequences for 54 different transcription factors. After conjugating with streptavidin-alkaline phosphatase (Perkin Elmer, Wilmington, Del.), the bound probes were visualized on a Kodak film by using CDP-Star chemiluminescence reagent (Tropix, Bedford, Mass.).

Electrophoretic Mobility Shift Assays (EMSA)

Brn3 binding studies were performed using double stranded oligonucleotides containing a Brn3 consensus site (5'-CACAGCTCATTAACGCGC-3' (SEQ ID NO:16), 3'-GTGTCGAGTAATTGCGCG-5' (SEQ ID NO:17)) (Panomics, Redwood City, Calif.). The oligonucleotides were end-labeled with $^{32}$-ATP using T4 polynucleotide kinase (Promega, Madison, Wis.) and incubated with nuclear extract for 20 min at room temperature. The samples were loaded on a 4% non-denaturing polyacrylamide gel. After electrophoresis, the gel was dried and exposed to Kodak film. Antibody supershift assays were carried out to confirm the identity of proteins in the Brn3 binding complex. Nuclear extracts were incubated with the appropriate antibody (Santa Cruz Biotechnology, Santa Cruz, Calif.) overnight at 4° C. followed by the addition of the labeled oligonucleotide probe.

RT-PCR

Total RNA was extracted using TRIZOL reagent (Invitrogen, Carlsbad, Calif.), reverse transcribed to cDNA with SuperScript II (Invitrogen, Carlsbad, Calif.), and used as a template for the PCR reaction. The PCR was done using the following primers:

```
                                                      (SEQ ID NO:18)
brn3a sense:              5'GCCAACCTCAAG-ATCCCGGGCG'3;

(SEQ ID NO:19)
brn3a anti-sense:         5'CCAGTTTCTCGGCGATGGCGGC'3;

(SEQ ID NO:20)
brn3b sense:              5'CACGGTGGTGTCCACTCCGG'3;

(SEQ ID NO:21)
brn3b anti-sense:         5'CCGCGATCTTCTCCGAGGAG'3;

(SEQ ID NO:22)
brn3c sense:              5'GGCCATGAACGCCAAGCAGCCTTTCGGC'3;

(SEQ ID NO:23)
brn3c anti-sense:         5'GCGCCT-AGATGATGCGGGTGGATCTGCG'3;

(SEQ ID NO:24)
synaptotagmin 1(Syt 1) sense: 5'-GACCGCTTCTCC-AAGCACGAC-'3;

(SEQ ID NO:25)
Syt 1 anti-sense:         5'-CTGCGCCGGTGCTGTTGTAG-'3.
```

Western Blot Analysis

Cells were washed twice with PBS and lysed with buffer (mmol/l: Tris HCL 20; NaCl 150; EDTA 1; sodium orthovanadate 1; PMSF 0.5; 10 µg/ml aprotinin; 1% Nonidet p40; 0.1% SDS). The samples were incubated on ice for 1.5 h, and centrifuged for 10 min at 4° C. in an Eppendorf centrifuge. The supernatants were collected and stored at −20° C. The protein concentration was determined using a protein assay reagent (Pierce, Rockford, Ill.). The samples were mixed with loading buffer (Sigma, St. Louis, Mo.), heated at 95° C. for 5 min, electrophoresed on a 12% SDS-polyacrylamide gel, and proteins were transferred onto a PVDF membrane. The proteins were detected with a primary anti-Brn3a or anti-Brn3b antibody (Santa Cruz Biotechnology, Santa Cruz, Calif.) using a Western blot kit (Invitrogen). Positive bands were visualized using the chemiluminescence reaction (Invitrogen) followed by exposure to photographic film.

Immunohistochemistry

Differentiated RAW264.7 cells were analyzed using a monoclonal antibody against Brn3a, and polyclonal antibodies against Brn3b (Santa Cruz Biotechnology, Santa Cruz, Calif.) and Brn3c (Covance Research Products, Berkeley, Calif.). The complementary secondary antibodies were conjugated with Alexa 488, Alexa 648 (Molecular Probes, Eugene, Oreg.) and rhodamine (Santa Cruz Biotechnology, Santa Cruz, Calif.) respectively. Samples were analyzed on a Leica TCS SP2 confocal microscope.

Histological Analysis of Osteoclast Differentiation

Tartrate-resistant acid phosphatase (TRAP) was detected using a commercially available system (Sigma-Aldrich, St. Louis, Mo.). after RANKL stimulation, RAW264.7 or bone marrow cells were washed twice with PBS (pH 7.4), fixed, washed again, and incubated with TRAP staining solution for 30 min at 37° C. TRAP-positive cells containing three or more nuclei were counted as osteoclasts. Images of the osteoclasts were taken under a bright field microscope and normalized onto a standardized quadrangle. The measurement of total osteoclast area was done using the Scion program (NCBI).

Analysis of Osteoclast Resorptive Activity

RAW264.7 or bone marrow cells in coculture with calvarial cells were induced to differentiate for 4-5 days or 7-10 days, respectively, on a 3D Collagen Cell Culture System matrix following the manufacturer's instructions (Chemicon International Inc., Temecula, Calif.). Cells were removed by dissolving the matrix in 0.2% collagenase, and were replated on 16-well Osteologic Multitest Slides (BD Bioscience, Bedford, Mass.) or 100 µm thick bovine bone slides. Cells were cultured for an additional 2 days in either DMEM/10%FBS with 10 ng/ml RANKL (RAW264.7), or αMEM/FBS with 25 ng/ml RANKL for osteoclasts derived from bone marrow. Resorption lacunae were photographed by bright field (Osteologic) or electron microscopy (bone slides) and analyzed using an image analyzing software (Scion Image NCBI).

Inhibition of Transcriptional Activation of Brn3-Proteins

Double-stranded oligonucleotides were prepared from complementary single stranded phosphorothioate-bonded fluorescence-labeled oligonucleotides by melting at 95° C. for 5 min followed by a cooling phase at room temperature. The sequences of the oligonucleotides were as follows: Brn3 sense: 5'-CACAGCTCATTAACGCGC-'3 (SEQ ID NO:26); Brn3 anti-sense: 5'-GCGCGTTAA-TGAGCTGTG-'3 (SEQ ID NO:27); Brn3 mutated sense: 5'-GCGCGTTGCT-GAGCTCTG-'3' (SEQ ID NO:28); Brn3 mutated anti-sense: 5'-CAGAGCTCAGCAACGCGC-'3 (SEQ ID NO:29). All decoy oligonucleotides were transfected into the cells using Oligofectamine Reagent (Invitrogen, Carlsbad, Calif.) and efficiency of transfection was monitored by fluorescence microscopy.

Analysis of Bone Micro-Architecture

The bone micro-architecture of mice carrying a targeted mutation of the brn3b gene was compared with heterozygous and wild type controls. Femurs were isolated and first analyzed by bone densitometry using dual-energy x-ray absorptiometry (DEXA, Piximus, Faxitron X-ray, Wheeling, Ill.). Bone micro-architecture was assessed in detail by micro-computed tomography using a fan-beam-type tomograph (μCT 40, Scanco Medical AG, Bassersdorf, Switzerland) and directed three-dimensional morphometry.

Statistical Analysis

Means were compared by using one-way analysis of Variance (ANOVA) or Students t test. $P<0.05$ was considered as significant.

```
brn3a
S69350 Mus sp. class V POU transcription factor (Brn3a) gene, complete cds.
                                                                    (SEQ ID NO:30)
    1 gagcagtgcg agcgagcgca cgctcgggac ggaggccggg cgagccggcg tgcgcacttt
   61 gccgcggact tgcgagtgt tttgtggatt tttacatgcc aaggcgccaa gatgatgtcc
  121 atgaacagca agcagcctca ctttgccatg catcccaccc tccctgagca caagtacccg
  181 tcgctgcact ccagctccga ggccatccgg cgggcctgcc tgcccacgcc gccggtaagc
  241 gccccacgcc gcggccccgg tccggcccg cgcgctcgcc ccctcccgcg tccgcgggtg
  301 gcggcagctg ccccgggcgg ctccgggccg ctcgcgggcg ggactgctct tagagggatc
  361 ccgctgccag gcacgcgtgg cccggggccg ctggaggccc gggtcccatc cgcctgtgcc
  421 tctgtccagc gcctgccatc cgcggggagc tctcgggccg cggctgtcga cttggctcca
  481 ctttgtcggt taattttacg cctgcacaag gcgatctctg ctcgctcgct cgctcgctcg
  541 ctcgctcgct cgctttctcg ttcgggtgtg tggcacgggt ccttagcttc gagtgacatc
  601 tccatttctt cttttcttc ttcttttcgc tctttttttgt cgtctcccac tgtcttcccc
  661 ggaatgtgtt tccgtgtgcg tcccttcta cccttccctg gccctgtgcc tctcccttc
  721 tatttccccc accccggcat gttctcaaat cgtccccgg tcctccgttg accctgctct
  781 tcccaccccc cgttgttatt ttggtcgctt tgtgttttgc cttttgcccg tgctttcctg
  841 cttgtgtgtt tgttttgtgg tttcttggt gtttgtcccc cctttttct tttttttct
  901 ttttctttct tcttttttt ttctttcctt ttctttttgg tttggtttgt gtcgcctgca
  961 gctgcagagc aacctcttcg ccagcctgga cgagacgctg ctggcgcggg ccgaggcgct
 1021 ggcggccgtg gacatcgcgg tgtcccaggg caagagccac cctttcaagc cggacgccac
 1081 gtaccacacg atgaatagcg tgccctgcac gtccacgtcc accgtgccgc tggcgcacca
 1141 ccaccaccac caccaccacc accaggcgct cgagcccggt gacctgctgg accacatctc
 1201 gtcgccgtcg ctcgcgctca tggccggcgc aggggcgca ggcgcggcgg gaggcggcgg
 1261 cggcgcccac gacggccccg ggggcggagg cggaccgggg ggcggcggtg gccgggcgg
 1321 cggcggcccc gggggtggcg gcggcggcgg cggcccgggg ggcggcggcg gcgccccggg
 1381 cggcgggctc ttgggcggct cggcgcatcc gcacccgcac atgcacggcc tgggccacct
 1441 gtcgcacccc gcggcggcgg cggccatgaa catgccgtcc gggctgccgc atcccgggct
 1501 cgtggccgcg gcggcgcacc acgcgcggc ggcggcagcg gcggcggcgg cggcggggca
 1561 ggtggcggcg gcgtcggccg cggcggcggt ggtgggcgcg gcgggcctgg cgtccatctg
 1621 cgactcggac acggaccccgc gcgagctcga ggcgttcgcc gagcgcttca agcagcggcg
 1681 catcaagctg ggcgtgacgc aggccgacgt gggctcggcg ctggccaacc tcaagatccc
 1741 gggcgtgggc tcgctcagcc agagcaccat ctgcaggttc gagtcgctca cgctctcgca
 1801 caacaacatg atcgcgctca gcccatcct gcaggcgtgg ctggaggagg ccgagggcgc
 1861 gcagcgtgag aaaatgaaca agccggagct cttcaacggc ggcgagaaga agcgcaagcg
 1921 gacttccatc gccgcgcccg agaagcgctc cctcgaggcc tattttgccg tacaacccg
```

-continued

```
1981 gccctcgtct gagaagatcg ccgccatcgc cgagaaactg gacctcaaaa agaacgtggt 2041 gcgggtgtgg ttttgcaacc agagacagaa gcagaagcgg atgaaattct ctgccactta 2101 ctgaggaggg tgtgagacgc gggtggggc acactgggga gctgaggggt gcgtttctgg
```
protein_id=AAB30577.2; db_xref=GI:8490223

(SEQ ID NO:31)

MMSMNSKQPHFAMHPTLPEHKYPSLHSSSEAIRRACLPTPPLQSNLFASLDETLLARAEALAAVDIAVSQGKSHPFK

PDATYHTMNSVPCTSTSTVPLAHHHHHHHHHQALEPGDLLDHISSPSLALMAGAGGAGAAGGGGGAHDGPGGGGGPG

GGGGPGGGGPGGGGGGGPGGGGGAPGGGLLGGSAHPHPHMHGLGHLSHPAAAAAMNMPSGLPHPGLVAAAAHHGAA

AAAAAAAAGQVAAASAAAAVVGAAGLASICDSDTDPRELEAFAERFKQRRIKLGVTQADVGSALANLKIPGVGSLSQ

STICRFESLTLSHNNMIALKPILQAWLEEAEGAQREKMNKPELFNGGEKKRKRTSIAAPEKRSLEAYFAVQPRPSSE

KIAAIAEKLDLKKNVVRVWFCNQRQKQKRMKFSATY

Human POU domain factor (Brn-3a) gene, exon 1.
ACCESSION U10062 U09783

(SEQ ID NO:32)
```
  1 atgatgtcca tgaacagcaa gcagcctcac tttgccatgc atcccaccct ccctgagcac 61 aagtacccgt cgctgcactc cagctccgag gccatccggc gggcctgcct gcccacgccg 121 ccg
```
Human POU daomain factor (Brn-3a) gene, exon 2, complete cds.
ACCESSION U10063 U09783

(SEQ ID NO:33)
```
  1 ctgcagagca acctcttcgc cagcctggac gagacgctgc tggcgcgggc cgaggcgctg 61 gcggccgtgg acatcgccgt gtcccagggc aagagccatc ctttcaagcc ggacgccacg 121 taccacacga tgaacagcgt gccgtgcacg tccacttcca cggtgcctct gggoaccac 181 caccaccaco accaccacca ccaggcgctc gaacccggcg atctgctgga ccacatctcc 241 tcgccgtcgc tcgcgctcat ggccggcgcg ggcggcgcgg gcggcgcggg cgcggcggcc 301 ggcggcggcg gcgcccacga cggcccgggg ggcggtggcg gcccgggcgg cggcggcggc 361 ccgggcggcg gcggccccgg gggaggcggc ggtggcggcc cggggggcgg cggcggcggc 421 ccgggcggcg ggctcctggg cggctccgcg caccotoaco cgcatatgca cagcctgggc 481 cacctgtcgc accccgcggc ggcggccgcc atgaacatgc cgtccgggct gccgcacccc 541 gggctggtgg cggcggcggc gcaccacggc gcggcagcgg cagoggoggo ggcggcggcc 601 gggcaggtgg cagcggcatc ggcggcggcg gccgtggtgg gcgcagcggg cctggcgtcc 661 atctgcgact cggacacgga cccgcgcgag ctcgaggcgt tcgcggagcg cttcaagcag 721 cggcgcatca gctgggcgt gacgcaggcc gacgtgggct cggcgctggc caacctcaag 781 atcccggggcg tgggctcact cagccagagc accatctgca ggttcgagtc gctcacgctc 841 tcgcacaaca acatgatcgc gctcaagccc atcctgcagg cgtggctcga ggaggccgag 901 ggcgcccagc gcgagaaaat gaacaagcct gagctcttca cggcggcga gaagaagcgc 961 aagcggactt ccatcgccgc gcccgagaag cgctccctcg aggcctactt cgccgtgcag 1021 ccccggccct cgtccgagaa gatcgccgcc atcgccgaga aactggacct caaaaagaac 1081 gtggtgcggg tgtggttttg caaccagaga cagaagcaga gcggatgaa attctctgcc 1141 acttactga
```
The ORF is nucleotides 1-123 of exon 1 and nucleotides 1-1149 of exon 2.

(SEQ ID NO: 34)

MMSMNSKQPHFAMHPTLPEHKYPSLHSSSEAIRRACLPTPPLQSNLFASLDETLLARAEALAAVDTAVSQGKSHPFK

PDATYHTMNSVPCTSTSTVPLRHHHHHHHHQALEPGDLLDHISSPSLALMAGAGGAGGAGAAAGGGGAHDGPGGGG

GPGGGGGPGGGGPGGGGGGGPGGGGGGPGGGLLGGSAHPHPHMHSLGHLSHPAAAAANNMPSGLPHPGLVAAAAHHG

AAAAAAAAAAGQVAAASAAAAVVGAAGLASICDSDTDPRELEAFAERFKQRRIKLGVTQADVGSALANLKIPGVGSL

SQSTICRFESLTLSHNNMIALKPILQAWLEEAEGAQREKMNKPELFNGGEKKRKRTSIAAPEKRSLEAYFAVQPRPS

SEKIAAIAEKLDLKKNVVRVWFCNQRQKQKRMKFSATY

-continued brn3b
S69351 Mus musculus BRN-3b (Brn-3b) gene, complete cds.
(SEQ ID NO:35)

```
   1 tttcaggatc actgtcatta ttattatttt aacgttctgg gaatgctgta ggcacggtgg
  61 cggtggcgag ccctgggccg ggggcttccg gagagagcgc tcacaattcc ctgctgagcg
 121 taatgtgtgc cttctactta caattgcaga gcaatatatt cggcgggctg gatgagagtc
 181 tgctggcccg tgccgaggct ctggccgccg tggacatcgt ctcccagagt aagagccacc
 241 accaccatcc gccccaccac agccccttca gccggacgc cacttaccac accatgaaca
 301 ccatcccgtg cacgtcggca gcctcctctt cttctgtgcc catctcgcac ccgtccgctc
 361 tggctggcac ccatcaccac caccaccacc accatcacca ccatcaccag ccgcaccagg
 421 cgctggaggg cgagctgctt gagcacctaa gccccgggct ggccctggga gctatggcgg
 481 gccccgacgg cacggtggtg tccactccgg ctcacgcacc acacatggcc accatgaacc
 541 ccatgcacca agcagccctg agcatggccc acgcacatgg gctgccctca cacatgggct
 601 gcatgagcga cgtggatgca gacccgcggg acctggaggc gttcgccgag cgtttcaagc
 661 agcgacgcat caagctggga gtgacccagg cagatgtggg ctcggcgctg gccaacctca
 721 agatcccggg cgtgggctcg ctcagccaga gcaccatctg caggtttgag tctctcacgc
 781 tgtcacacaa caacatgatc gcgctcaagc ccatcctgca ggcgtggctg gaggaagctg
 841 agaaatccca ccgcgagaag ctcactaagc cggagctctt caatggcgcg gagaagaagc
 901 gcaagcgcac gtccatcgcg gcgccggaga gcgctctct ggaagcctac ttcgccatcc
 961 agccaaggcc ctcctcggag aagatcgcgc ccatcgccga aaagctggat ctcaagaaaa
1021 atgtggtgcg cgtctggttc tgcaaccaga ggcagaaaca gaaggtg aaatactctg
1081 ccggcattta g
``` protein_id=AAB30578.1; db_xref=GI:546434
(SEQ ID NO:36)

MCAFYLQLQSNIFGGLDESLLARAEALAAVDIVSQSKSHHHHPPHHSPFKPDATYHTMNTIPCTSAASSSSVPISHP
SALAGTHHHHHHHHHHHHQPHQALEGELLEHLSPGLALGAMAGPDGTVVSTPAHAPHMATMNPMHQAALSMAHAHGL
PSHMGCMSDVDADPRDLEAFAERFKQRRIKLGVTQADVGSALANLKIPGVGSLSQSTICRFESLTLSHNNMIALKPI
LQAWLEEAEKSHREKLTKPELFNGAEKKRKRTSIAAPEKRSLEAYFAIQPRPSSEKIAAIAEKLDLKKNVVRVWFCN
QRQKQKKVKYSAGI

Human POU domain protein (Brn-3b) mRNA, complete cds.
ACCESSION U06233
(SEQ ID NO:37)

```
   1 agacctcggc acccgttcag actgacagca gaggoggoga aggagcgcgt agccgagatc
  61 aggcgtacag agtccggagg cggcggcggg tgagctcaac ttcgcacagc ccttcccagc
 121 tccagccccg gctggcccgg cacttctcgg agggtcccgg cagccgggac cagtgagtgc
 181 ctctacggac cagcgccccg gcgggcggga agatgatgat gatgtccctg aacagcaagc
 241 aggcgtttag catgccgcac ggcggcagcc tgcacgtgga gcccaagtac tcggcactgc
 301 acagcacctc gccgggctcc tcggctccca tcgcgccctc ggccagctcc cccagcagct
 361 cgagcaacgc tgttggtggc ggcggcggcg gcggcggcg cggcggcggc ggcggaggcc
 421 gaagcagcag ctccagcagc agtggcagca gcggcggcgg gggctcggag gctatgcgga
 481 gagcctgtct tccaaccca ccgagcaata tattcggcgg gctggatgag agtctgctgg
 541 cccgcgccga ggctctggca gccgtggaca tcgtctccca gagcaagagc caccaccacc
 601 atccacccca ccacagcccc ttcaaaccgg acgccaccta ccacactatg aataccatcc
 661 cgtgcacgtc ggccgcctct tcttcatcgg tgcccatctc gcacccttgc gcgttggcgg
 721 gcacgcacca ccaccaccac catcaccacc accaccacca ccaaccgcac caggcgctgg
 781 agggcgagct gctggagcac ctgagtcccg gcctggccct gggcgctatg gcgggccccg
```

```
 841 acggcgctgt ggtgtccacg ccggctcacg cgccgcacat ggccaccatg aaccccatgc 901 accaagcagc gctcagcatg gcccacgcgc acgggctgcc gtcgcacatg ggctgcatga 961 gcgacgtgga cgccgacccg cgggacctgg aggcattcgc cgagcgcttc aagcagcgac 1021 gcatcaagct gggggtgacc caggcagatg tgggctccgc gctggccaac ctcaagatcc 1081 ccggcgtggg ctcgcttagc cagagcacca tctgcaggtt cgagtccctc acactgtccc 1141 acaataatat gatcgcgctc aaacccatcc tgcaggcatg gctcgaggag gccgagaagt 1201 cccaccgcga gaagctcacc aagcctgaac tcttcaatgg cgcggagaag aagcgcaagc 1261 gcacgtccat cgctgcgcca gagaagcgct cgctcgaagc ctactttgcc attcagcctc 1321 ggccctcctc tgaaaagatc gccgccatcg cggagaagct ggacctgaag aaaaacgtgg 1381 tgcgcgtctg gttctgcaac cagaggcaga acagaaaag aatgaaatat ccgccggca 1441 tttagaagac tcttggcctc tccagagacg cccctttcct cgtccgctct tttctctcct 1501 ctcttctgcc tctttcact tttggcgact agaaacaatt ccagtaaatg tgaatctcga 1561 caaatcgagg actgaagagg gagcgaacga gcgaacaact gagcccaagc cggtgagaat 1621 gtgaaacagt ttctcaaagg aaagaataac aaaagatggt atttgtctgt tgtagcaaag 1681 ttgtcccttt gaaccccacc tcggcttctt cagaggaagt gtggagatgg ctgtttgcag 1741 gaaggcagac gagacagtgt ttaaaaagtc cacaagaatg atcaagtaag atttgttttt 1801 attcttacag acatcacccg tgttcaagtt taaaagtaca ctttgcaact atttttcaga 1861 aatgaaatt gattcaggac taaaacttta aactagagtt gatgcttaat gtgatagaga 1921 catctctaaa gtattttgaa ttttaaaaaa agatggcaga ttttctgcat ttacactgta 1981 tattatatat atatttttat tgtggttctt accccctttt ccttctctga agtgttaatg 2041 cttaagaaaa gagttgcgcc tgctgtgttc actgatcttg aaagctatta ttagattatt 2101 gcagaacaac cctctgtaaa ttattaattt atctctctag caacttaatt ttgtgcacat 2161 tctaattaat taaacttctt ccgtctaaaa aaagtgggg aaatgtatag ctagtaacgt 2221 tcaaaaaatt ttgtttgatg agtttaccga attttacag cttttcctcct atactgtgtt 2281 ccttttgacc catttgtata ttctcacttg aatgaagatt gttttttct ttgttttac 2341 tggtagtgtt ctgatttgtg agtcgacact cagtaatgga tgtcttaatc gtgtagacct 2401 gattcactgt ctgaagtatt gtttacttcg ttacatattt aatggggatt cccacattgt 2461 ccccatgaca catgagcgct ctcacttacc cttacacaca cacacacaca cacacacaca 2521 cctctaacag aagggaagaa gcagttggaa gcatgaccga tgcaccattt tctagtttta 2581 ggtgcatttg ccacttggtg tttgcccttc agattttaga tttcaccaag gtatttcagt 2641 cttccagttt tcaattgctt tgttggctac atgttaatat ttataggaat acttcagttt 2701 ttccttttgg aggtttgttt gtagaaaaac taatttgaac tataagaaag acagtgcact 2761 gcttgtaaat tcacattgtt tggaaaaatt cttttggaac aaaaaattag gtacatgata 2821 actggtacct tatctactgt aaatatttca ttaaaaatga tgcacacata gatatattct 2881 tacaaatttt gctgtattgc tgttctcttt gaggctctcc aaagtcttga gttctgtata 2941 tggcctggtt tcttgttttt attaatagat ggtttattta ctatggtaat gtattaattt 3001 atttttggtg ttgttcgatt gtctttcatt gaagagataa ttttaatgtt ttattggcaa 3061 cgtatgctgc ttttcatta aaatatgcta ttaaaattaa atggctttta
```
The ORF is nucleotides 213-1445.
protein_id=AAA16509.1; db_xref="GI:458391"

(SEQ ID NO:38)
MMMMSLNSKQAFSMPHGGSLHVEPKYSALHSTSPGSSAPIAPSASSPSSSSNAGGGGGGGGGGGGGGGRSSSSSSS

GSSGGGGSEAMRRACLPTPPSNIFGGLDESLLARAEALAAVDIVSQSKSHHHHPPHHSPFKPDATYHTMNTIPCTSA

ASSSSVPTSHPCALAGTHHHHHHHHHHHQPHQALEGELLEHLSPGLALGAMAGPDGAVVSTPAHAPHMATMNPMHQ

AALSMAHAHGLPSHMGCMSDVDADPRDLEAFAERFKQRRIKLGVTQADVGSALANLKIPGVGSLSQSTICRFESLTL

SHNNMIALKPILQAWLEEAEKSHREKLTKPELFNGAEKKRKRTSIAAPEKRSLEAYFAIQPRPSSEKIAAIAEKLDL

KKNVVRVWFCNQRQKQKRMKYSAGI brn3c
S69352 Mus musculus BRN-3c (Brn-3c) gene, complete cds.

(SEQ ID NO:39)

```
   1 caagcgagag ggcgagggga gcgctggcgc tgagcggcgc tcacttggag cgcggagagc
  61 tagcaagacg agcttgattc catgtccccc gctgcctccc tgccagactc ccgaagatga
 121 tggccatgaa cgccaagcac cgtttcggca tgcaccccgt actgcaagaa cccaaattct
 181 ccagcctaca ctccggctct gaggccatgc gccgagtttg tctcccagcc ccgcaggtac
 241 gtagcggacg ataattaccg ctctaaggca cattttttga caggcactag cttcatgttt
 301 ttttcatgtc gcccagaaca atcgccgctg tctgaacccc tcgccttgtc tccccgcgc
 361 tctctcgcgg ctctctctct ctctctctct ctctctctct ctctcattca
 421 tgtctctgat ccacacgtct gttccaacag agaggctgcc tccgtattaa tttttatgac
 481 ctgggctttg aggagaggca tctcggttgc ttgaaaatgt gttttaatcc tgagttgaca
 541 gtattcccca ctgaccgtgc tgtgcgcctt ctcgcttgca gctgcagggt aatatatttg
 601 gaagctttga tgagagcctg ctggcacgcg ccgaagctct ggcggcggtg gatatcgtct
 661 cccacggcaa gaaccatccg ttcaagcccg acgccaccta ccataccatg agcagcgtgc
 721 cctgcacttc tacctcgccc acggtgccca tctctcaccc ggctgcactc acctcgcacc
 781 cgcatcacgc ggtacatcag ggcctcgagg gcgacttact tgagcacatc tcgcccacgc
 841 tgagcgtgag tggcctaggg gccccggagc actcggtgat gccggcgcag atccacccgc
 901 atcatctagg cgccatgggc cacttgcatc aggccatggg catgagtcac ccgcatgccg
 961 tagcaccgca cagtgccatg cccgcgtgtc tcagcgatgt ggagtcagac cctcgagagc
1021 tggaagcgtt cgccgagcgc ttcaagcaga ggcgcatcaa gttggggtc acccaggcgg
1081 acgtgggcgc ggctttagcc aatcttaaga tccccggtgt gggctcgctc agccagagca
1141 ccatctgcag gttcgagtct cttactctgt cgcacaacaa catgatcgct ctcaagccgg
1201 tcctccaggc ctggctggag gaggccgagg ccgcctaccg agagaagaac agcaagccag
1261 agctcttcaa cggcagtgag cgtaagcgca aacgcacgtc catcgccgcg ccagagaagc
1321 gctcactcga agcctatttc gccatccagc cacgtccttc atccgagaag atcgcggcca
1381 tcgcggagaa actggacctt aaaaagaatg tggtgagggt ctggttctgt aaccagagac
1441 agaaacagaa acgaatgaaa tactctgctg tggactgatt gcggcgggtg ctgcgtccgg
1501 aggagcctgg agagcctaat gcatcgcccc cttccgatgg gaggggagct tacgggacac
1561 tccagggtgt ttcctggcag gtcaggttct ttcc
``` protein_id=AAB30579.1; db_xref=GI:546436

(SEQ ID NO:40)

MMAMNAKHRFGMHPVLQEPKFSSLHSGSEAMRRVCLPAPQLQGNIFGSFDESLLARAEALAAVDIVSHGKNHPFKPD

ATYHTMSSVPCTSTSPTVPISHPAALTSHPHHAVHQGLEGDLLEHISPTLSVSGLGAPEHSVMPAQIHPHHLGAMGH

LHQAMGMSHPHAVAPHSAMPACLSDVESDPRELEAFAERFKQRRIKLGVTQADVGAALANLKIPGVGSLSQSTICRF

ESLTLSHNNMIALKPVLQAWLEEAEAAYREKNSKPELFNGSERKRKRTSIAAPEKRSLEAYFAIQPRPSSEKIAAIA

EKLDLKKNVVRVWFCNQRQKQKRDdKYSAVD

Human POU domain factor (Brn-3c) gene, exon 1.
ACCESSION U10060 U09718

(SEQ ID NO:41)

```
   1 atgatggcca tgaactccaa gcagcctttc ggcatgcacc cggtgctgca agaacccaaa
```

```
-continued
 61 ttctccagtc tgcactctgg ctccgaggct atgcgccgag tctgtctccc agccccgcag
```
Human POU domain factor (Brn-3c) gene, exon 2, complete cds.
ACCESSION U10061 U09718

(SEQ ID NO:42)
```
  1 ctgcagggta atatatttgg aagctttgat gagagcctgc tggcacgcgc cgaagctctg 61 gcggcggtgg atatcgtctc ccacggcaag aaccatccgt tcaagcccga cgccacctac 121 cataccatga gcagcgtgcc ctgcacgtcc acttcgtcca ccgtgcccat ctcccaccca 181 gctgcgctca cctcacaccc tcaccacgcc gtgcaccagg gcctcgaagg cgacctgctg 241 gagcacatct cgcccacgct gagtgtgagc ggcctgggcg ctccggaaca ctcggtgatg 301 cccgcacaga tccatccaca ccacctgggc gccatgggcc acctgcacca ggccatgggc 361 atgagtcacc cgcacaccgt ggcccctcat agcgccatgc ctgcatgcct cagcgacgtg 421 gagtcagacc cgcgcgagct ggaagccttc gccgagcgct tcaagcagcg gcgcatcaag 481 ctggggggtga cccaggcgga cgtgggcgcg gctctggcta atctcaagat ccccggcgtg 541 ggctcgctga gccaaagcac catctgcagg ttcgagtctc tcactctctc gcacaacaac 601 atgatcgctc tcaagccggt gctccaggcc tggttggagg aggccgaggc cgcctaccga 661 gagaagaaca gcaagccaga gctcttcaac ggcagcgaac ggaagcgcaa acgcacgtcc 721 atcgcggcgc cggagaagcg ttcactcgag gcctatttcg ctatccagcc acgtccttca 781 tctgagaaga tcgcggccat cgctgagaaa ctggaccta aaaagaacgt ggtgagagtc 841 tggttctgca accagagaca gaaacagaaa cgaatgaagt attcggctgt ccactga
```
The ORF is nucleotides 1-120 of exon 1 and nucleotides 1-897 of exon 2.
protein_id=AAA57160.1 db_xref=GI:602102

(SEQ ID NO:43)
MMAMNSKQPFGMHPVLQEPKFSSLHSGSEAMRRVCLPAPQLQGNIFGSFDESLLARAEALAAVDIVSHGKNHPFKPD

ATYHTMSSVPCTSTSSTVPISHPAALTSHPHHAVHQGLEGDLLEHISPTLSVSGLGAPEHSVMPAQIHPHHLGAMGH

LHQAMGMSHPHTVAPHSAMPACLSDVESDPRELEAFAERFKQRRIKLGVTQADVGAALANLKTPGVGSLSQSTICRF

ESLTLSHNNMIALKPVLQAWLEEAEAAYREKNSKPELFNGSERKRKRTSIAAPEKRSLEAYFAIQPRPSSEKIAAIA

EKLDLKKNVVRVWFCNQRQKQKRMKYSAVH

The present invention features methods of identifying a bone resorption disease or a bone generating disease, methods for prognosing and/or diagnosing a bone resorption disease or a bone generating disease, methods for identifying a compound that modulates bone resorption disease development or bone generating disease development, methods for determining the efficacy of a bone resorption disease therapy or a bone generating disease therapy, and oligonucleotide microarrays containing probes for genes involved in osteoclast development.

Accordingly, the invention features a method of identifying a bone resorption disease comprising determining a gene expression profile from a gene expression product of at least one bone resorption disease informative gene having increased expression in osteoclasts in a sample derived from bone tissue relative to a control. Increased expression of the gene expression product in the sample is indicative of a bone resorption disease.

The invention features a method of identifying a bone resorption disease comprising determining a gene expression profile from a gene expression product of at least one bone resorption disease informative gene having decreased expression in osteoclasts in a sample derived from bone tissue relative to a control. Decreased expression of the gene expression product in the sample is indicative of a bone resorption disease.

The invention features a method of identifying a bone generating disease comprising determining a gene expression profile from a gene expression product of at least one bone resorption disease informative gene having increased expression in osteoclasts in a sample derived from bone tissue relative to a control. Decreased expression of the gene expression product in the sample is indicative of a bone generating disease.

The invention features a method of identifying a bone generating disease comprising determining a gene expression profile from a gene expression product of at least one bone resorption disease informative gene having decreased expression in osteoclasts in a sample derived from bone tissue relative to a control. Increased expression of the gene expression product in the sample is indicative of a bone generating disease.

The invention features a method of identifying a Compound for use in decreasing bone resorption disease development, comprising the steps of contacting a cell or cell lysate sample with a candidate compound; and detecting an increase in expression of at least one informative gene having decreased expression in osteoclasts. A candidate compound that increases the expression of the informative gene is a compound for use in decreasing bone resorption disease development.

The invention features a method of identifying a compound for use in decreasing bone resorption disease development, comprising the steps of contacting a cell or cell lysate sample with a candidate compound; and detecting a decrease in expression of at least one informative gene having increased expression in osteoclasts. A candidate compound that decreases the expression of the informative gene is a compound for use in decreasing bone resorption disease development.

The invention features a method of identifying a compound for use in decreasing bone generating disease development, comprising the steps of contacting a cell or cell lysate sample with a candidate compound; and detecting a decrease in expression of at least one informative gene having decreased expression in osteoclasts. A candidate compound that decreases the expression of the informative gene is a compound for use in decreasing bone generating disease development.

The invention features a method of identifying a compound for use in decreasing bone generating disease development, comprising the steps of contacting a cell or cell lysate sample with a candidate compound; and detecting an increase in expression of at least one informative gene having increased expression in osteoclasts. A candidate compound that increases the expression of the informative gene is a compound for use in decreasing bone generating disease development.

The above-described compound screening methods can be carried out by detecting a change in the biological activity of an informative gene expression product as an indication that the candidate compound is useful for decreasing development of a bone resorption disease or a bone generating disease.

Screens can be carried out for compounds that further increase the expression of a gene or the biological activity of a gene expression product already overexpressed in a bone resorption disease or a bone generating disease, or that further decrease the expression of a gene or the biological activity of a gene expression product already underexpressed in a bone resorption disease or a bone generating disease. These compounds can be identified according the screening methods described herein. These compounds should be avoided during treatment regimens for a bone resorption disease or a bone generating disease. For example, a compound that further increases the expression of a gene or the biological activity of a gene expression product already overexpressed in a bone resorption disease, or that further decreases the expression of a gene or the biological activity of a gene expression product already underexpressed in a bone resorption disease can be identified as a compound that should not be administered to a patient with a bone resorption disease. In addition, a compound that further increases the expression of a gene or the biological activity of a gene expression product already overexpressed in a bone generating disease, or that further increases the expression of a gene or the biological activity of a gene expression product already underexpressed in a bone generating disease can be identified as a compound that should not be administered to a patient with a bone generating disease.

The invention features a method of identifying a polypeptide that interacts with an informative gene expression product having increased or decreased expression in osteoclasts, a bone resorption disease, or a bone generating disease in a yeast two-hybrid system. The method comprises providing a first nucleic acid vector comprising a nucleic acid molecule encoding a DNA binding domain and a polypeptide encoded by the informative gene that is increased or decreased in osteoclasts, a bone resorption disease, or a bone generating disease; providing a second nucleic acid vector comprising a nucleic acid encoding a transcription activation domain and a nucleic acid encoding a test polypeptide; contacting the first nucleic acid vector with the second nucleic acid vector in a yeast two-hybrid system; and assessing transcriptional activation in the yeast two-hybrid system. An increase in transcriptional activation relative to a control indicates that the test polypeptide is a polypeptide that interacts with the informative gene expression product having increased or decreased expression in osteoclasts, a bone resorption disease, or a bone generating disease.

The invention also relates to compounds identified according to the above-described screening methods. Such compounds can be used to treat a bone resorption disease or a bone generating disease, as appropriate.

The invention features a method of predicting the likelihood of bone resorption disease development in a subject, comprising determining a gene expression profile from a gene expression product of at least one informative gene having increased expression in osteoclasts in a sample derived from bone tissue of a subject relative to a control. Increased expression of the gene in the sample indicates an increased likelihood of bone resorption disease development in the subject.

The invention features a method of predicting the likelihood of bone resorption disease development in a subject, comprising determining a gene expression profile from a gene expression product of at least one informative gene having decreased expression in osteoclasts in a sample derived from bone tissue of a subject relative to a control. Decreased expression of the gene in the sample indicates an increased likelihood of bone resorption disease development in the subject.

The invention features a method of predicting the likelihood of bone generating disease development in a subject, comprising determining a gene expression profile from a gene expression product of at least one informative gene having increased expression in osteoclasts in a sample derived from bone tissue of a subject relative to a control. Decreased expression of the gene in the sample indicates an increased likelihood of bone generating disease development in the subject.

The invention features a method of predicting the likelihood of bone generating disease development in a subject, comprising determining a gene expression profile from a gene expression product of at least one informative gene having decreased expression in osteoclasts in a sample derived from bone tissue of a subject relative to a control. Increased expression of the gene in the sample indicates an increased likelihood of bone generating disease development in the subject.

The invention features a method of diagnosing a bone resorption disease in a subject, comprising determining a gene expression profile from a gene expression product of at least one informative gene having increased expression in osteoclasts in a sample derived from bone tissue of a subject relative to a control. Increased expression of the gene in the sample indicates the presence of a bone resorption disease in the subject.

The invention features a method of diagnosing a bone resorption disease in a subject, comprising determining a gene expression profile from a gene expression product of at least one informative gene having decreased expression in osteoclasts in a sample derived from bone tissue of a subject relative to a control. Decreased expression of the gene in the sample indicates the presence of a bone resorption disease in the subject.

The invention features a method of diagnosing a bone generating disease in a subject, comprising determining a gene expression profile from a gene expression product of at least one informative gene having increased expression in osteoclasts in a sample derived from bone tissue of a subject relative to a control. Decreased expression of the gene in the sample indicates the presence of a bone generating disease in the subject.

The invention features a method of diagnosing a bone generating disease in a subject, comprising determining a gene expression profile from a gene expression product of at least one informative gene having decreased expression in osteoclasts in a sample derived from bone tissue of a subject relative to a control. Increased expression of the gene in the sample indicates the presence of a bone generating disease in the subject.

The invention features a method of assessing efficacy of treatment of a bone resorption disease in a subject comprising the steps of determining a gene expression profile from a gene expression product of at least one informative gene having increased expression in osteoclasts in a sample derived from bone tissue of a subject relative to a control, and repeating the above step at one or more time points during treatment. Decreased expression of the gene in the sample over time indicates an effective treatment.

The invention features a method of assessing efficacy of treatment of a bone resorption disease in a subject comprising the steps of determining a gene expression profile from a gene expression product of at least one informative gene having increased expression in osteoclasts in a sample derived from bone tissue from a subject relative to a control, and repeating the above step at one or more time points during treatment. Increased expression or lack of decreased expression of the gene in the sample over time indicates a less effective treatment.

The invention features a method of assessing efficacy of treatment of a bone resorption disease in a subject comprising the steps of determining a gene expression profile from a gene expression product of at least one informative gene having decreased expression in osteoclasts in a sample derived from bone tissue of a subject relative to a control, and repeating the above step at one or more time points during treatment. Increased expression of the gene in the sample over time indicates an effective treatment.

The invention features a method of assessing efficacy of treatment of a bone resorption disease in a subject comprising the steps of determining a gene expression profile from a gene expression product of at least one informative gene having decreased expression in osteoclasts in a sample derived from bone tissue of a subject relative to a control, and repeating the above step at one or more time points during treatment. Decreased expression or a lack of increased expression of the gene in the sample over time indicates a less effective treatment.

The invention features a method of assessing efficacy of treatment of a bone generating disease in a subject comprising the steps of determining a gene expression profile from a gene expression product of at least one informative gene having increased expression in osteoclasts in a sample derived from bone tissue of a subject relative to a control, and repeating the above step at one or more time points during treatment. Increased expression of the gene in the sample over time indicates an effective treatment.

The invention features a method of assessing efficacy of treatment of a bone generating disease in a subject comprising the steps of determining a gene expression profile from a gene expression product of at least one informative gene having increased expression in osteoclasts in a sample derived from bone tissue of a subject relative to a control, and repeating the above step at one or more time points during treatment. Decreased expression or lack of increased expression of the gene in the sample over time indicates a less effective treatment.

The invention features a method of assessing efficacy of treatment of a bone generating disease in a subject comprising the steps of determining a gene expression profile from a gene expression product of at least one informative gene having decreased expression in osteoclasts in a sample derived from bone tissue of a subject relative to a control, and repeating the above step at one or more time points during treatment. Decreased expression of the gene in the sample over time indicates an effective treatment.

The invention features a method of assessing efficacy of treatment of a bone resorption disease in a subject comprising the steps of determining a gene expression profile from a gene expression product of at least one informative gene having decreased expression in osteoclasts relative to a control, and repeating the above step at one or more time points during treatment. Increased expression or a lack of decreased expression of the gene in the sample over time indicates a less effective treatment.

The gene expression product is DNA or mRNA. In another embodiment, the gene expression profile is determined utilizing specific hybridization probes. The expression profile can be determined, for example, using oligonucleotide microarrays. In another embodiment, the gene expression product is a polypeptide. When the gene expression product is a polypeptide, the gene expression profile can be determined, for example, utilizing antibodies.

The invention features a solid substrate having immobilized thereon a plurality of detection agents specific for one or more informative genes selected from the group consisting of the genes in FIGS. 1A-1E and 2A-2B. In one embodiment, the solid substrate is a microarray. In another embodiment, the detection agents are a plurality of oligonucleotide probes specific for one or more informative genes selected from the group consisting of the genes in FIGS. 1A-1E and 2A-2B. In still another embodiment, the detection agents are a plurality of gene expression products encoded by one or more informative genes selected from the group consisting of the genes in FIGS. 1A-1E and 2A-2B.

The present invention relates to one or more osteoclast markers or sets of osteoclast markers or informative genes (also referred to as osteoclast associated genes) whose expression correlates with a distinction between samples. In a particular embodiment, the distinction is a distinction between the presence or absence of bone resorbing activity or bone generating activity, or the presence or absence of a bone resorption disease or a bone generating disease in a patient from which the sample was obtained. The distinction can also be efficacy of treatment.

Osteoclast markers are listed in FIGS. 1A-1E and in FIGS. 2A-2B. Osteoclast markers include MIP-1γ, CCR1, MIP-1α, RANTES, bm3a, bm3b, and brn3c.

An "informative gene" is a gene that can be used to classify a sample. An informative gene can be, for example, a gene that is differentially expressed in samples that are compared. Genes that are increased or decreased in expression in macrophages that have been stimulated to undergo differentiation into osteoclasts compared to unstimulated macrophages are examples of informative genes, and are also referred to herein as "bone resorption disease informative genes." Informative genes that are osteoclast markers for use in the present invention are those shown in FIGS. 1A-1E (informative genes with increased expression in osteoclasts) and FIGS. 2A-2B (informative genes with decreased expression in osteoclasts). Particular informative genes are MIP-1γ, CCR1, MIP-1α, RANTES, brn3a, bm3b, and bm3c.

"Bone resorbing activity" means a body process through which bone is removed from the body, resulting in a decrease in bone mass and/or bone structure. Osteoclasts are the cells in the body responsible for bone resorption. In the body, bone resorbing activity is counteracted by "bone generating activity," a process by which new bone is formed by osteoblasts.

Too much bone resorbing activity, caused, for example, by the presence of too many osteoclasts, increased osteoclast activity, too few osteoblasts, and/or decreased osteoblast activity can lead to the development (initiation or progressions) of a "bone resorption disease," in which bone mass decreases below normal levels, resulting in structural deterioration of bone tissue. Bone mass can be measured using standard tests, for example, bone mineral density tests. Examples of bone resorption diseases include osteoporosis, hyperparathyroidism, Paget's disease, inflammatory conditions, rheumatoid arthritis, osteoarthritis, and periodontitis.

Insufficient levels of bone resorbing activity, caused, for example, by an insufficient number of osteoclasts, insufficient osteoclast activity, too many osteoblasts, and/or too much osteoblast activity, can result in development (initiation or progressions) of a "bone generating disease," in which bone mass increases above normal levels or in which bones are not remodeled by osteoclasts. Examples of bone generating diseases include osteopetrosis, axial osteosclerosis, and Osteopathia striata.

The level of expression of osteoclast markers is determined to classify a sample as to the presence or absence of bone resorbing activity or bone generating activity or the presence or absence of a bone resorption disease or a bone generating disease in the patient from which the sample was obtained. Genes having increased expression in differentiated osteoclasts or in cells undergoing differentiation into osteoclasts are compared to those in cells with the potential to differentiate into osteoclasts, but which have not undergone differentiation, or cells having decreased expression in differentiated osteoclasts or in cells differentiating into osteoclasts are compared to those in cells with the potential to differentiate into osteoclasts, but which have not undergone differentiation. Such osteoclast markers or bone disease informative genes can be, for example, all or a subset of the genes shown in FIGS. 1A-1E and FIGS. 2A-2B. FIGS. 1A-1E show informative genes (i.e., osteoclast markers) whose expression is increased in RAW 264.7 macrophage-like cells stimulated with Receptor Activator of NFκB Ligand (RANKL) and normal mouse bone marrow macrophages stimulated with Macrophage-Colony Stimulating Factor (M-CSF) and RANKL, compared to unstimulated cells (control). FIGS. 2A-2B show informative genes whose expression is decreased in RAW 264.7 macrophage-like cells stimulated with Receptor Activator of NFκB Ligand (RANKL) and normal mouse bone marrow macrophages stimulated with Macrophage-Colony Stimulating Factor (M-CSF) and RANKL, compared to unstimulated cells (control).

The invention also relates to methods of diagnosing or predicting the likelihood of development of a bone resorption disease or a bone generating disease in a patient comprising the steps of providing a sample, for example, from one or more cells (e.g., bone cells and/or bone marrow); and determining a gene expression profile of at least one informative gene or determining the level of expression of an osteoclast marker in the sample, wherein the gene expression profile or the level of expression is correlated with the presence or absence of a bone resorption disease or a bone generating disease or an increased or decreased likelihood of developing a bone resorption disease or a bone generating disease.

"Gene expression products" are proteins, polypeptides, or nucleic acid molecules (e.g., mRNA, tRNA, rRNA, or cRNA) that result from transcription or translation of genes. The present invention can be effectively used to analyze proteins, peptides or nucleic acid molecules that are the result of transcription or translation. The nucleic acid molecule levels measured can be derived directly from the gene or, alternatively, from a corresponding regulatory gene or regulatory sequence element. All forms of gene expression products can be measured. Additionally, variants of genes and gene expression products including, for example, spliced variants and polymorphic alleles, can be measured. Similarly, gene expression can be measured by assessing the level of protein or derivative thereof translated from mRNA. The sample to be assessed can be any sample that contains a gene expression product. Suitable sources of gene expression products, e.g., samples, can include intact cells, lysed cells, cellular material for determining gene expression, or material containing gene expression products.

Examples of such samples are brain, blood, bone marrow, plasma, lymph, urine, tissue, mucus, sputum, saliva or other cell samples. Methods of obtaining such samples are known in the art. The sample can be bone marrow tissue or bone cells, such as osteogenic cells, osteoblasts, osteoclasts, osteocytes, and bone lining cells, as well as bone cell progenitors (e.g., pre-osteoblasts and pre-osteoclasts i.e., cells the are destined to become or can be stimulated to become osteoblasts or osteoclasts but do not yet have osteoblast or osteoclast biological activity) are used. In another preferred embodiment, bone marrow tissue is used.

In one embodiment, the gene expression product is a protein or polypeptide. The determination of the gene expression profile can be made using techniques for protein detection and quantitation known in the art. For example, antibodies specific for the protein or polypeptide can be obtained using methods, which are routine in the art, and the specific binding of such antibodies to protein or polypeptide gene expression products can be detected and measured. Alternatively, the biological activity of the gene-expression product can be measured as an indicator of the gene expression profile.

The gene expression product can be mRNA and the gene expression levels are obtained, e.g., by contacting the sample with a suitable microarray, and determining the extent of hybridization of the nucleic acid in the sample to the probes on the microarray.

Using the methods described herein, expression of numerous osteoclast markers can be measured simultaneously to determine an expression profile. The assessment of numerous genes provides for a more accurate evaluation of the sample because there are more osteoclast markers or informative genes that can assist in classifying the sample.

"Expression profile" or "gene expression profile" is the level or amount of expression of osteoclast markers or informative genes as assessed by methods described herein. The expression profile can comprise data for one or more osteoclast markers or informative genes and can be measured at a single time point or over a period of time.

Gene expression profiles can be determined using various methods known in the art. For example, gene expression levels can be measured or assessed and assigned a value that is obtained from an apparatus that can measure gene expression levels. Gene expression levels refer to the amount of expression of the gene expression product, as described herein. The values are raw values from the apparatus, or values that are optionally rescaled, filtered and/or normalized. Such data is obtained, for example, from a GENE-CHIP® probe array or Microarray (Affymetrix, Inc.) (U.S. Pat. Nos. 5,631,734, 5,874,219, 5,861,242, 5,858,659, 5,856,174, 5,843,655, 5,837,832, 5,834,758, 5,770,722, 5,770,456, 5,733,729, and 5,556,752, all of which are incorporated herein by reference in their entirety), and the expression levels are calculated with software (e.g., Affymetrix GENE-CHIP® software). Nucleic acids (e.g., mRNA) from a sample which has been subjected to particular stringency conditions hybridize to the probes on the chip. The nucleic acid to be analyzed (e.g., the target) is isolated, amplified and labeled with a detectable label, (e.g., $^{32}P$ or fluorescent label) prior to hybridization to the arrays. Once hybridization occurs, the arrays are inserted into a scanner which can detect patterns of hybridization. The hybridization data are collected as light emitted from the labeled groups which is now bound to the probe array. The probes that perfectly match the target produce a stronger signal than those that have mismatches. Since the sequence and position of each probe on the array are known, by complementarity, the identity of the target nucleic acid applied to the probe is determined. Quantitation of gene profiles from the hybridization of labeled mRNA/DNA microarray can be performed by scanning the microarrays to measure the amount of hybridization at each position on the microarray with an Affymetrix scanner (Affymetrix, Santa Clara, Calif.).

For each stimulus, a time series of cDNA levels (C={C1, C2, C3, . . . Cn}) and a corresponding time series of mRNA levels (M={M1, M2, M3, . . . Mn}) in control medium in the same experiment as the stimulus is obtained. Quantitative data is then analyzed using methods known in the art. Microarrays are only one method of obtaining gene expression values. Other methods for obtaining gene expression values known in the art or developed in the future can be used with the present invention.

Once the gene expression values are prepared, the sample can be classified. Genes that can be used for classification (informative genes) have been identified as a result of work described herein and are shown in FIGS. 1A-1E and 2A-2B. Not all informative genes for a particular class distinction (e.g., bone resorbing activity, bone generating activity, a bone resorption disease, or a bone generating disease) must be assessed in order to classify a sample. For example, a subset of the informative genes which demonstrate a high correlation with a class distinction can be used. This subset can be, for example, one or more genes, for example, 2, 3, or 4 genes, 5 or more genes, for example, 6, 7, 8, or 9 genes, 10 or more genes, 25 or more genes, or more genes, or 50 or more genes. One subset is one or more of OC 1-285, brn3a, brn3b, and brn3c. Another subset is one or more of OC 286-364. Typically the accuracy of the classification will increase with the number of informative genes assessed.

The invention also provides methods (also referred to herein as "screening assays") for identifying agents or compounds (e.g., fusion proteins, polypeptides, peptidomimetics, prodrugs, receptors, binding agents, antibodies, small molecules or other drugs, or ribozymes) that alter or modulate (e.g., increase or decrease) the activity or expression of the osteoclast markers (e.g., polypeptides encoded by the informative genes) as described herein, or that otherwise interact with the informative genes and/or polypeptides described herein. Such compounds can be compounds or agents that bind to informative gene expression products described herein (e.g., the polypeptides encoded by the informative genes in FIGS. 1A-1E and 2A-2B), and that have a stimulatory or inhibitory effect on, for example, activity of the polypeptide encoded by an informative gene described herein; or that change (e.g., enhance or inhibit) the ability of a polypeptide encoded by an informative gene to interact with compounds or agents that bind such an informative gene polypeptide; or that alter post-translational processing of such a polypeptide (e.g., agents that alter proteolytic processing to direct the polypeptide from where it is normally synthesized to another location in the cell, such as the cell surface or the nucleus; or agents that alter proteolytic processing such that more polypeptide is released from the cell, etc.). The modulation can result in an increase or a decrease in the occurrence, severity, or progression of a bone resorption disease or a bone generating disease.

The candidate compound can cause an alteration in the activity of a polypeptide encoded by an informative gene of the present invention. For example, the activity of the polypeptide can be altered (increased or decreased) by at least 1.5-fold to 2-fold, at least 3-fold, or, at least 5-fold, relative to the control. Alternatively, the polypeptide activity can be altered, for example, by at least 10%, at least 20%, 40%, 50%, or 75%, or by at least 90%, relative to the control.

The invention provides assays for screening candidate compounds or test agents to identify compounds that bind to or modulate the activity of a polypeptide encoded by an informative gene described herein (or biologically active portion(s) thereof), as well as agents identifiable by the assays. A "candidate compound", "candidate substance" or "test agent" is a chemical molecule, be it naturally-occurring or artificially-derived, and includes, for example, peptides, proteins, synthetic molecules, for example, synthetic organic molecules, naturally-occurring molecules, nucleic acid molecules, and components thereof.

In general, candidate compounds for use in the present invention may be identified from large libraries of natural products or synthetic (or semi-synthetic) extracts or chemical libraries according to methods known in the art. The precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modifications of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. For example, candidate compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to polypeptide libraries, while the other four approaches are applicable to polypeptide, non-peptide oligomer or small molecule libraries of compounds (Lam, Anticancer Drug Des., 12: 145 (1997)). Furthermore, if desired, any library or compound is readily modified using standard chemical, physical, or biochemical methods.

When a crude extract is found to modulate (i.e., increase or decrease) the expression and/or activity of the informative genes and/or their encoded polypeptides, further fractionation of the positive lead extract is necessary to isolate chemical constituents responsible for the observed effect. Thus, the goal of the extraction, fractionation, and purification process is the careful characterization and identification of a chemical entity within the crude extract having an activity that stimulates or inhibits nucleic acid expression, polypeptide expression, or polypeptide biological activity. The same assays described herein for the detection of activities in mixtures of compounds can be used to purify the active component and to test derivatives thereof. Methods of fractionation and purification of such heterogeneous extracts are known in the art. If desired, compounds shown to be useful agents for treatment are chemically modified according to methods known in the art. Compounds identified as being of therapeutic value may be subsequently analyzed using animal models for diseases in which it is desirable to alter the activity or expression of the nucleic acids or polypeptides of the present invention.

To identify candidate compounds that alter the biological activity of a polypeptide encoded by an informative gene as described herein, a cell, tissue, cell lysate, tissue lysate, or solution containing or expressing a polypeptide encoded by the informative gene (e.g., a polypeptide encoded by a gene in any of FIGS. 1A-1E or 2A-2B), or a fragment or derivative thereof, can be contacted with a candidate compound to be tested under conditions suitable for biological activity of the polypeptide. Alternatively, the polypeptide can be contacted directly with the candidate compound to be tested. The level (amount) of polypeptide biological activity is assessed/measured, either directly or indirectly, and is compared with the level of biological activity in a control (i.e., the level of activity of the polypeptide or active fragment or derivative thereof in the absence of the candidate compound to be tested, or in the presence of the candidate compound vehicle only). If the level of the biological activity in the presence of the candidate compound differs, by an amount that is statistically significant, from the level of the biological activity in the absence of the candidate compound, or in the presence of the candidate compound vehicle only, then the candidate compound is a compound that alters the biological activity of the polypeptide encoded by an informative gene of the invention. For example, an increase in the level of polypeptide biological activity relative to a control, indicates that the candidate compound is a compound that enhances (is an agonist of) the polypeptide biological activity. Similarly, a decrease in the polypeptide biological activity relative to a control, indicates that the candidate compound is a compound that inhibits (is an antagonist of) the polypeptide biological activity.

The level of biological activity of an osteoclast marker that is a polypeptide encoded by an informative gene in the presence of the candidate compound to be tested, is compared with a control level that has previously been established. A level of polypeptide biological activity in the presence of the candidate compound that differs from (i.e., increases or decreases) the control level by an amount that is statistically significant indicates that the compound alters the biological activity of the polypeptide.

The level and/or pattern of expression of an osteoclast marker that is an informative gene in the presence of the candidate compound to be tested, is compared with a control level and/or pattern of expression that has previously been established. A level and/or pattern of expression of an osteoclast marker that is an informative gene expression in the presence of the candidate compound that differs from the control level and/or pattern of expression by an amount or in a manner that is statistically significant indicates that the candidate compound alters osteoclast marker expression.

Compounds that alter the expression of an osteoclast marker, or that otherwise interact with an osteoclast marker described herein, can be identified using a cell, cell lysate, or solution containing a nucleic acid encoding the promoter region of an osteoclast marker that is an informative gene operably linked to a reporter gene. A "promoter" is a minimal nucleotide sequence sufficient to direct transcription, and "operably linked" means that a gene and one or more regulatory sequences are connected in such a way as to permit gene expression when the appropriate molecules (e.g., transcriptional activator proteins) are bound to the regulatory sequences. Examples of reporter genes and methods for operably linking a reporter gene to a promoter are known in the art. After contact with a candidate compound to be tested, the level of expression of the reporter gene (e.g., the level of mRNA or of protein expressed) is assessed, and is compared with the level of expression in a control (i.e., the level of expression of the reporter gene in the absence of the candidate compound, or in the presence of the candidate compound vehicle only). If the level of expression in the presence of the candidate compound differs by an amount or in a manner that is statistically significant from the level in the absence of the candidate compound, or in the presence of the candidate compound vehicle only, then the candidate compound is a compound that alters the expression of the informative gene, as indicated by its ability to alter expression of the reporter gene that is operably linked to the informative gene promoter. Enhancement of the expression of the reporter gene indicates that the compound is an agonist of the informative gene polypeptide activity. Similarly, inhibition of the expression of the reporter gene indicates that the compound is an antagonist of the informative gene polypeptide activity.

In another embodiment, the level of expression of the reporter in the presence of the candidate compound to be tested, is compared with a control level that has been established previously. A level in the presence of the candidate compound that differs from the control level by an amount or in a manner that is statistically significant indicates that the candidate compound alters informative gene expression.

The present invention also features methods of detecting and/or identifying a compound that alters the interaction between a polypeptide encoded by an informative gene and a polypeptide (or other molecule) with which the polypeptide normally interacts (e.g., in a cell or under physiological conditions). In one exanple, a cell or tissue that expresses or contains a compound (e.g., a polypeptide or other molecule) that interacts with a polypeptide encoded by an informative gene (such a molecule is referred to herein as a "polypeptide substrate") is contacted with the informative gene polypeptide in the presence of a candidate compound, and the ability of the candidate compound to alter the interaction between the polypeptide encoded by the informative gene and the polypeptide substrate is determined, for example, by assaying activity of the polypeptide. Alternatively, a cell lysate or a solution containing the informative gene polypeptide, the polypeptide substrate, and the candidate compound can be used. A compound that binds to the informative gene polypeptide or to the polypeptide substrate can alter the interaction between the informative gene polypeptide and the polypeptide substrate by interfering with (inhibiting), or enhancing the ability of the informative gene polypeptide to bind to, associate with, or otherwise interact with the polypeptide substrate.

Determining the ability of the candidate compound to bind to the informative gene polypeptide or a polypeptide substrate can be accomplished, for example, by coupling the candidate compound with a radioisotope or enzymatic label such that binding of the candidate compound to the informative gene polypeptide or polypeptide substrate can be determined by directly or indirectly detecting the candidate compound labeled with $^{125}$I, $^{35}$S, $^{14}$C, or $^{3}$H, and the detecting the radioisotope (e.g., by direct counting of radioemission or by scintillation counting). Alternatively, the candidate compound can be enzymatically labeled with, for example, horseradish peroxidase, alkaline phosphatase, or luciferase, and the enzymatic label is then detected by determination of conversion of an appropriate substrate to product. In another alternative, one of the other components of the screening assay (e.g., the polypeptide substrate or the informative gene polypeptide) can be labeled, and alterations in the interaction between the informative gene polypeptide and the polypeptide substrate can be detected. In these methods, labeled unbound components can be removed (e.g., by washing) after the interaction step in order to accurately detect the effect of the candidate compound on the interaction between the informative gene polypeptide and the polypeptide substrate.

It is also within the scope of this invention to determine the ability of a candidate compound to interact with the informative gene polypeptide or polypeptide substrate without labeling of any of the interactants. For example, a microphysiometer can be used to detect the interaction of a candidate compound with a polypeptide encoded by an informative gene or a polypeptide substrate without labeling either the candidate compound, the polypeptide encoded by the informative gene, or the polypeptide substrate (McConnell et al., Science 257: 1906-1912 (1992)). A "microphysiometer" (e.g., CYTOSENSOR™) is an analytical instrument that measures the rate at which a cell acidifies its environment using a light-addressable potentiometric sensor (LAPS). Changes in this acidification rate can be used as an indicator of the interaction between ligand and polypeptide.

Assays can be used to identify polypeptides that interact with one or more polypeptides encoded by an informative gene. For example, a yeast two-hybrid system such as that described by Fields and Song (Fields and Song, Nature 340: 245-246 (1989)) can be used to identify polypeptides that interact with one or more polypeptides encoded by an informative gene.

In the above assay methods of the present invention, it may be desirable to immobilize a polypeptide encoded by an informative gene, or a polypeptide substrate, or other components of the assay on a solid support, in order to facilitate separation of complexed from uncomplexed forms of one or both of the polypeptides, as well as to accommodate automation of the assay. Binding of a candidate compound to the polypeptide, or interaction of the polypeptide with a polypeptide substrate in the presence and absence of a candidate compound, can be accomplished in any vessel suitable for containing the reactants. Examples of such vessels include microtitre plates, test tubes, and micro-centrifuge tubes. In one embodiment, a fusion protein (e.g., a glutathione-S-transferase fusion protein) can be provided that adds a domain that allows the informative gene polypeptide, or the polypeptide substrate to be bound to a matrix or other solid support.

This invention further pertains to novel compounds identified by the above-described screening assays. Accordingly, it is within the scope of this invention to further use a compound identified as described herein in an appropriate animal model. For example, a compound identified as described herein can be used in an animal model to determine the efficacy, toxicity, or side effects of treatment with such a compound. Furthermore, this invention pertains to uses of novel compounds identified by the above-described screening assays for treatments as described herein. In addition, a compound identified as described herein can be used to alter activity of a polypeptide encoded by an informative gene, or to alter expression of the informative gene, by contacting the polypeptide or the nucleic acid molecule (or contacting a cell comprising the polypeptide or the nucleic acid molecule) with the compound identified as described herein.

Compounds identified according to the methods of the above-described screens can be used to modulate (increase or decrease (inhibit)) bone resorbing activity or bone generating activity. A candidate compound that decreases the expression of an informative gene with increased expression in osteoclasts or increases the expression of an informative gene with decreased expression in osteoclasts is a compound for use in decreasing or inhibiting bone resorbing activity in a subject or for treating a bone resorption disease. Such a compound is also useful for increasing bone generating activity in a subject. In addition, a candidate compound that increases the expression of an informative gene with increased expression in osteoclasts or that decreases the expression of an informative gene with decreased expression in osteoclasts is a compound for use in decreasing or inhibiting bone generating activity in a subject or for treating a bone generating disease. Such a compound is also useful for increasing bone resorbing activity in a subject.

The cell or cell lysate sample is derived from bone tissue. In another example, the sample comprises or consists of osteoclasts and/or osteoblasts. Such cells can be primary cells or cultured cells. In another embodiment, the informative genes having increased expression in osteoclasts are selected from the group consisting of the genes in FIGS. 1A-1E and the informative genes having decreased expression in osteoclasts are selected from the group consisting of the genes in FIGS. 2A-2B.

The present invention further relates to antibodies that specifically bind a polypeptide, preferably an epitope, of an informative gene product of the present invention (as determined, for example, by immunoassays, a technique well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, for example, anti-Id antibodies to antibodies of the invention), and epitope-binding fragments of any of the above.

An "antibody," refers to immunoglobulin molecules and immunologically active portions of immunoglobulin molecules, and more specifically, molecules that contain an antigen binding site that specifically binds an antigen. The immunoglobulin molecules of the invention can be of any type (for example, IgG, IgE, IgM, IgD, IgA and IgY), and of any class (for example, IgG1, IgG2, IgG3, IgG4, IgA1 and IgA2) or subclass of an immunoglobulin molecule.

The antibodies can be antigen-binding antibody fragments and include, without limitation, Fab, Fab' and F(ab')$_2$, Fd, single-chain Fvs (scFv), single chain antibodies, disulfide-linked Fvs (sdFv) and fragments comprising either a V$_L$ or V$_H$ domain. Antigen-binding antibody fragments, including single-chain antibodies, can comprise the variable region(s) alone or in combination with the entirety or a portion of one or more of the following: hinge region, CH1, CH2, and CH3 domains. Also included in the invention are antigen-binding fragments also comprising any combination of variable region(s) with a hinge region, CH1, CH2, and/or CH3 domains.

The antibodies of the invention may be from any animal origin including birds and mammals. Preferably, the antibodies are human, murine, donkey, sheep, rabbit, goat, guinea pig, hamster, horse, or chicken.

"Human" antibodies include antibodies having the amino acid sequence of a human immunoglobulin and include antibodies produced by human B cells, or isolated from human sera, human immunoglobulin libraries or from animals transgenic for one or more human immunoglobulins and that do not express eridogenous immunoglobulins, as described in U.S. Pat. No. 5,939,598 by Kucherlapati et al., for example.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material.

Antibodies of the present invention may be described or specified in terms of the epitope(s) or portion(s) of a polypeptide of the present invention that they recognize or specifically bind. The epitope(s) or polypeptide portion(s) may be specified, for example, by N-terminal and/or C-terminal positions, or by size in contiguous amino acid residues. Antibodies that specifically bind any epitope or polypeptide encoded by an informative gene of the present invention may also be excluded. Therefore, the present invention includes antibodies that specifically bind a polypeptide encoded by an informative gene of the present invention, and allows for the exclusion of the same.

An "epitope," is a portion of a polypeptide which contacts an antigen-binding site(s) of an antibody or T cell receptor. Specific binding of an antibody to an antigen having one or more epitopes excludes non-specific binding to unrelated antigens, but does not necessarily exclude cross-reactivity with other antigens with similar epitopes.

Antibodies of the present invention may also be described or specified in terms of their cross-reactivity. Antibodies of the present invention may not display any cross-reactivity, such that they do not bind any other analog, ortholog, or homolog of a polypeptide of the present invention. Alternatively, antibodies of the invention can bind polypeptides with at least about 95%, 90%, 85%, 80%, 75%, 70%, 65%, 60%, 55%, or 50% identity (as calculated using methods known in the art) to a polypeptide encoded by an informative gene of the present invention. Further included in the present invention are antibodies that bind polypeptides encoded by informative genes that hybridize to an informative gene of the present invention under stringent hybridization conditions, as will be appreciated by one of skill in the art.

Antibodies of the present invention can also be described or specified in terms of their binding affinity to a polypeptide of the invention. Preferred binding affinities include those with a dissociation constant or Kd less than $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 11^{-10}$ M, $10^{-11}$ M, $5 \times 10^{-12}$ M, $10^{-11}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of a polypeptide of the invention, as determined by any method known in the art for determining competitive binding, for example, using immunoassays. In particular embodiments, the antibody competitively inhibits binding to the epitope by at least about 90%, 80%, 70%, 60%, or 50%.

Antibodies of the present invention can act as agonists or antagonists of polypeptides encoded by the informative genes of the present invention. For example, the present invention includes antibodies which disrupt interactions with the polypeptides encoded by the informative genes of the invention either partially or fully. The invention also includes antibodies that do not prevent binding, but prevent activation or activity of the polypeptide. Activation or activity (for example, signaling) may be determined by techniques known in the art. Also included are antibodies that prevent both binding to and activity of a polypeptide encoded by an informative gene. Likewise included are neutralizing antibodies.

Antibodies of the present invention may be used, for example, and without limitation, to purify, detect, and target the polypeptides encoded by the informative genes described herein, including both in vitro and in vivo diagnostic and therapeutic methods. For example, the antibodies have use in immunoassays for qualitatively and quantitatively measuring levels of the polypeptides in biological samples. See, for example, Harlow et al., Antibodies: A Laboratory Manual (Cold Spring Harbor Laboratory Press, 2nd ed. 1988).

The antibodies of the present invention may be used either alone or in combination with other compositions. The antibodies may further be recombinantly fused to a heterologous polypeptide at the N- and/or C-terminus or chemically conjugated (including covalent and non-covalent conjugations) to polypeptides or other compositions. For example, antibodies of the present invention may be recombinantly fused or conjugated to molecules useful as labels in detection assays, or effector molecules such as heterologous polypeptides, drugs, or toxins.

The antibodies of the invention include derivatives that are modified, for example, by the covalent attachment of any type of molecule to the antibody such that covalent attachment does not prevent the antibody from recognizing its epitope. For example, but not by way of limitation, the antibody derivatives include antibodies that have been modified by glycosylation, acetylation, pegyllation, phosphorylation, amidation, derivatization by known protecting/blocking groups, proteolytic cleavage, or linkage to a cellular ligand or other protein. Any of numerous chemical modifications can be carried out by known techniques, including, but not limited to, specific chemical cleavage, acetylation, formylation, and metabolic synthesis of tunicamycin. Additionally, the derivative can contain one or more non-classical amino acids.

The antibodies of the present invention can be generated by any suitable method known in the art. For example, a polypeptide of the invention can be administered to various host animals including, but not limited to, rabbits, mice, rats, or the like, to induce the production of sera containing polyclonal antibodies specific for the antigen. Various adjuvants can be used to increase the immunological response, depending on the host species, and include, but are not limited to, Freund's adjuvant (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and corynebacterium parvum. Such adjuvants are well known in the art.

Monoclonal antibodies can be prepared using a wide variety of techniques also known in the art, including hybridoma cell culture, recombinant, and phage display technologies, or a combination thereof. "Monoclonal antibodies" are not necessarily limited to antibodies produced through hybridoma technology, but also refer to antibodies that are derived from a single clone, including any eukaryotic, prokaryotic, or phage clone.

Human antibodies are desirable for therapeutic treatment of human patients. These antibodies can be made by a variety of methods known in the art including phage display methods using antibody libraries derived from human immunoglobulin sequences. Human antibodies can also be produced using transgenic mice that are incapable of expressing functional endogenous immunoglobulins, but which can express human immunoglobulin genes. The transgenic mice are immunized with a selected antigen, for example, all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For a detailed discussion of this technology for producing human antibodies and human monoclonal antibodies and protocols for producing such antibodies, see, for example, PCT publications WO 98/24893; WO 96/34096; WO 96/33735; and U.S. Pat. Nos. 5,413,923; 5,625,126; 5,633,425; 5,569,825; 5,661,016; 5,545,806; 5,814,318; and 5,939,598.

Antibodies to the polypeptides encoded by the informative genes as described herein can, in turn, be utilized to generate anti-idiotype antibodies that "mimic" polypeptides of the invention using techniques well known to those skilled in the art. (See, for example, Greenspan & Bona, FASEB J. 7(5): 437-444 (1989) and Nissinoff, J. Immunol. 147(8):2429-2438 (1991)). For example, antibodies that bind to and competitively inhibit polypeptide multimerization and/or binding of a polypeptide to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide encoded by an informative gene and/or to bind its ligands, and thereby block its biological activity.

The antibodies or fragments thereof of the present invention can be fused to marker sequences, such as a peptide to facilitate their purification. For example, marker amino acid sequences include a hexa-histidine peptide, an HA tag, or a FLAG tag.

The present invention further encompasses antibodies or fragments thereof conjugated to a diagnostic or therapeutic agent. The antibodies can be used diagnostically, for example, to monitor the development or progression of a bone resorption or bone generation disease or disorder as part of a clinical testing procedure to determine the efficacy of a given treatment regimen. Detection can be facilitated by coupling the antibody to a detectable substance. Examples of detectable substances include enzymes (such as, horseradish peroxidase, alkaline phosphatase, beta-galactosidase, or acetyicholinesterase), prosthetic groups (such as streptavidinlbiotin and avidin/biotin), fluorescent materials (such as umbelliferone, fluorescein, fluorescein isothiocyanate, rhodamine, dichlorotriazinylamine fluorescein, dansyl chloride or phycoerythrin), luminescent materials (such as luminol), bioluminescent materials (such as luciferase, luciferin, and aequorin), radioactive materials (such as, $^{125}I$ $^{131}I$, $^{111}In$ or $^{99}Tc$), and positron emitting metals using various positron emission tomographies, and nonradioactive paramagnetic metal ions.

An antibody or fragment thereof can be conjugated to a therapeutic moiety such as a bisphosphonate (e.g., alendronate, risedronate, pamidronate, etidronate, or tiludronate), calcitonin, estrogen, or an estrogen modulator.

Antibodies of the invention can also be attached to solid supports. These are particularly useful for immunoassays or purification of the target antigen. Such solid supports include, but are not limited to, glass, cellulose, silicon, polyacrylamide, nylon, polystyrene, polyvinyl chloride or polypropylene. Techniques for conjugating such therapeutic moiety to antibodies are well known in the art, see, for example, Anion et al., "Monoclonal Antibodies For Immunotargeting Of Drugs In Cancer Therapy", in Monoclonal Antibodies And Cancer Therapy, Reisfeld et al. eds., pp. 243-56 (Alan R. Liss, Inc. 1985).

Alternatively, an antibody can be conjugated to a second antibody to form an antibody heteroconjugate as described by Segal in U.S. Pat. No. 4,676,980.

An antibody of the invention, with or without conjugation to a therapeutic moiety, administered alone or in combination with an additional therapeutic agent, can be used as a therapeutic.

Antisense antagonists are also included in the present invention. Antisense technology can be used to control gene expression through antisense DNA or RNA, or through triple-helix formation. Antisense techniques are discussed for example, in Okano (J., Neurochem. 56:560 (1991)). The methods are based on binding of a polynucleotide to a complementary DNA or RNA. An antisense sequence can be generated internally by the organism, alternatively, the antisense sequence is separately administered.

The 5' coding portion of an informative gene can be used to design an antisense RNA oligonucleotide from about 10 to 40 base pairs in length. Generally, a DNA oligonucleotide is designed to be complementary to a region of the gene involved in transcription thereby preventing transcription and the production of the polypeptide. The antisense RNA oligonucleotide hybridizes to the mRNA in vivo and blocks translation of the mRNA molecule into polypeptide.

The antisense nucleic acid of the invention can be produced intracellularly by transcription from an exogenous sequence. For example, a vector or a portion thereof, is transcribed, producing an antisense nucleic acid of the invention. Such a vector contains the sequence encoding the antisense nucleic acid. The vector can remain episomal or become chromosomally integrated, as long as it can be transcribed to produce the desired antisense RNA. Vectors can be constructed by recombinant DNA technology and can be plasmid, viral, or otherwise, as is known in the art.

Expression can be controlled by any promoter known in the art to act in the target cells, such as vertebrate cells, and preferably human cells. Such promoters can be inducible or constitutive and include, without limitation, the SV40 early promoter region (Bernoist and Chambon, Nature 29:304-3 10 (1981), the promoter contained in the 3' long terminal repeat of Rous sarcoma virus (Yamamoto et al., Cell 22:787-797 (1980)), the herpes thymidine promoter (Wagner et al., Proc. Nail Acad. Sci. U.S.A. 78:1441-1445 (1981)), and the regulatory sequences of the metallothionein gene (Brinster et al., Nature 296:39-42 (1982)).

The antisense nucleic acids of the invention comprise a sequence complementary to at least a portion of an RNA transcript of an informative gene. Absolute complementarity, although preferred, is not required. A sequence "complementary to at least a portion of an RNA," is a sequence having sufficient complementarity to be able to hybridize with the RNA, forming a stable duplex. The ability to hybridize will depend on both the degree of complementarity and the length of the antisense nucleic acid. Generally, the larger the hybridizing nucleic acid, the more base mismatches with the RNA it may contain and still form a stable duplex.

Oligonucleotides that are complementary to the 5' end of the RNA, for example, the 5' untranslated sequence up to and including the AUG initiation codon, are generally regarded to work most efficiently at inhibiting translation. However, sequences complementary to the 3' untranslated sequences of mRNAs have been shown to be effective at inhibiting translation of mRNAs as well. Thus, oligonucleotides complementary to either the 5'- or 3'-non-translated, non-coding regions of a nucleotide sequence can be used in an antisense approach to inhibit mRNA translation. Oligonucleotides complementary to the 5' untranslated region of the mRNA can include the complement of the AUG start codon. Antisense oligonucleotides complementary to mRNA coding regions can also be used in accordance with the invention. In one embodiment, the antisense nucleic acids are at least six nucleotides in length, and are preferably oligonucleotides ranging from about 6 to about 50 nucleotides in length. In other embodiments, the oligonucleotide is at least about 10, 17, 25 or 50 nucleotides in length.

The antisense oligonucleotides of the invention can be DNA or RNA, or chimeric mixtures, or derivatives or modified versions thereof, single-stranded or double-stranded. The oligonucleotide can be modified at the base moiety, sugar moiety, or phosphate backbone, for example, to improve stability of the molecule, hybridization, and the like. The oligonucleotide can include other appended groups such as peptides (for example, to target host cell receptors in vivo), or agents that facilitate transport across the cell membrane, or the blood-brain barrier, or intercalating agents.

The antisense oligonucleotide may comprise at least one modified base moiety which is selected from the group including, but not limited to, 5-fluorouracil, 5-bromouracil, 5-chiorouracil, 5-iodouracil, hypoxanthine, xanthine, 4-acetylcytosine, 5-(carboxyhydroxylmethyl) uracil, 5-carboxymethylaminomethyl-2-thiouridine, 5-5 carboxymethylaminomethyluracil, dihydrouracil, a-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, betaD-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

The antisense oligonucleotide can comprise at least one modified phosphate backbone selected from the group including, but not limited to, a phosphorothioate, a phosphorodithioate, a phosphoramidothioate, a phosphoramidate, a phosphordiamidate, a methyiphosphonate, an alkyl phosphotriester, and a formacetal or analog thereof.

Alternatively, the antisense oligonucleotide is an a-anomeric oligonucleotide. An cx-anomenc oligonucleotide forms specific double-stranded hybrids with complementary RNA in which, contrary to the usual β-units, the strands run parallel to each other (Gautier et al., Nucl. Acids Res. 15:6625-664 1 (1987)). The oligonucleotide is a 2'-O-methylribonucleotide (Inoue et al., Nucl. Acids Res. 15:6131-6148 (1987)), or a chimeric RNA-DNA analog (Inoue et al., FEBS Lett. 2 15:327-330 (1987)).

Antisense oligonucleotides of the invention may be synthesized by standard methods known in the art, for example, by use of an automated DNA synthesizer.

Potential antagonists of the informative genes of the invention also include catalytic RNA, or a ribozyme. Hammerhead ribozymes cleave mRNAs at locations dictated by flanking regions that form complementary base pairs with the target mRNA. The target mRNA has the following sequence of two bases: 5'-UG-3'. The construction and production of hammerhead ribozymes is well known in the art and is described more fully in Haseloff and Gerlach (Nature 334:585-59 1 (1988)). Preferably, the ribozyme is engineered so that the cleavage recognition site is located near the 5' end of the mRNA in order to increase efficiency and minimize the intracellular accumulation of non-functional mRNA transcripts.

Ribozymes of the invention can be composed of modified oligonucleotides (for example for improved stability or targeting). DNA constructs encoding the ribozyme can be under the control of a strong constitutive promoter, such as, for example, pol III or pol II promoter, so that a transfected cell will produce sufficient quantities of the ribozyme to destroy endogenous target mRNA and inhibit translation. Since ribozymes, unlike antisense molecules, are catalytic, a lower intracellular concentration is generally required for efficiency.

The present invention also provides pharmaceutical compositions, including both therapeutic and prophylactic compositions. Compositions within the scope of this invention include all compositions wherein the therapeutic agent, antibody, fragment or derivative, antisense oligonucleotide or ribozyme is contained in an amount effective to achieve its intended purpose. The effective dose is a function of a number of factors, including the specific antibody, the antisense oligonucleotide, antisense construct, ribozyme or polypeptide of the invention, the presence of a conjugated therapeutic agent, the patient and their clinical status.

The mode of administration may be by parenteral, subcutaneous, intravenous, intramuscular, intraperitoneal, transdermal, or buccal routes. Alternatively, or concurrently, administration may be orally. The dosage administered will be dependent upon the age, health, and weight of the recipient, kind of concurrent treatment, if any, frequency of treatment, and the nature of the effect desired.

Such compositions generally comprise a therapeutically effective amount of a compound, and a pharmaceutically acceptable carrier. "Pharmaceutically acceptable" means approved by a regulatory agency of the Federal or a state government or listed in the U.S. Pharmacopoeia or other generally recognized pharmacopoeia for use in animals, and more particularly in humans. A "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skimmed milk, glycerol, propylene, glycol, water, ethanol and the like. The composition can also contain minor amounts of wetting or emulsifying agents, and/or pH buffering agents.

These compositions can take the form of solutions, suspensions, emulsion, tablets, pills, capsules, powders, or sustained-release formulations. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like. Such compositions will contain a therapeutically effective amount of the compound, preferably in purified form, together with a suitable amount of carrier so as to provide the form for proper administration to the patient. The formulation should suit the mode of administration.

The composition can be formulated in accordance with routine procedures as a pharmaceutical composition adapted for intravenous administration to a human. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, and the like, and those formed with cations such as those derived from sodium, potassium, ammonium, calcium, ferric hydroxides, isopropylamine, triethylamine, 2-ethylamino ethanol, histidine, procaine, and the like.

The compositions of the invention can be administered alone or in combination with other therapeutic agents. Therapeutic agents that can be administered in combination with the compositions of the invention, include but are not limited to chemotherapeutic agents, antibiotics, steroidal and nonsteroidal anti-inflammatories, conventional immunotherapeutic agents, cytokines and/or growth factors. Combinations may be administered either concomitantly, for example, as an admixture, separately but simultaneously or concurrently; or sequentially. This includes presentations in which the combined agents are administered together as a therapeutic mixture, and also procedures in which the combined agents are administered separately but simultaneously, for example, as through separate intravenous lines into the same individual. Administration "in combination" further includes the separate administration of one of the compounds or agents given first, followed by the second.

Conventional, nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents.

Antibiotic agents that may be administered with the compositions of the invention include, but are not limited to, tetracycline, metronidazole, amoxicillin, betalactamases, aminoglycosides, macrolides, quinolones, fluoroquinolones, cephalosporins, erythromycin, ciprofloxacin, and streptomycin. Anti-inflammatory agents that can be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, aryipropionic acid derivatives, pyrazoles, pyrazolones, salicylic acid derivatives, thiazinecarboxamides, e-acetamnidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with another therapeutic agent for treating a bone resorption disease, or a bone generating disease. Therapeutic agents that may be administered with the compositions of the invention include, but are not limited to, a bisphosphonate (e.g., alendronate, risedronate, pamidronate, etidronate, or tiludronate), calcitonin, estrogen, and estrogen modulators.

The present invention is further directed to therapies which involve administering pharmaceutical compositions of the invention to an animal, preferably a mammal, and most preferably a human patient, for treating one or more of the described disorders. Therapeutic compositions of the invention include, for example, therapeutic agents identified in screening assays, antibodies of the invention (including fragments, analogs and derivatives thereof as described herein), antisense oligonucleotides, ribozymes and nucleic acids encoding same. The compositions of the invention can be used to treat, inhibit, prognose, diagnose or prevent diseases, disorders or conditions associated with aberrant expression and/or activity of a polypeptide of the invention, including, but not limited to, any one or more of the diseases, disorders, or conditions such as, for example, a bone resorption disease or a bone generating disease.

The treatment and/or prevention of diseases and disorders associated with aberrant expression and/or activity of a polypeptide of the invention includes, but is not limited to, alleviating symptoms associated with those diseases and disorders. The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Furthermore, the dosage and frequency of administration of antibodies of the invention may be reduced by enhancing uptake and tissue penetration of the antibodies by modifications such as, for example, lipidation or addition of cell-specific tags.

The compounds or pharmaceutical compositions of the invention can be tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed. The effect of such compounds or pharmaceutical compositions can be determined by measuring a change in the level of expression or a change in the expression profile of osteoclast markers.

The invention provides methods of treatment, inhibition and prophylaxis by administration to a subject an effective amount of a compound or pharmaceutical composition of the invention. The compound is substantially purified such that the compound is substantially free from substances that limit its effect or produce undesired side-effects. The subject is preferably an animal, including but not limited to animals such as cows, pigs, horses, chickens, cats, dogs, etc., and is preferably a mammal, and most preferably human.

Various delivery systems are known and can be used to administer a composition of the invention, for example, encapsulation in liposomes (Langer, Science 249:1527-1533 (1990)), microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, and the like. Methods of introduction include, but are not limited to, intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical compounds or compositions of the invention can be introduced into the central nervous system by any suitable route, including intraventricular and intrathecal injection. Intraventricular injection can be facilitated by an intraventricular catheter, for example, attached to a reservoir, such as an Ommaya reservoir. Pulmonary administration can also be employed, for example, by use of an inhaler or nebulizer, and formulation with an aerosolizing agent.

The pharmaceutical compounds or compositions of the invention can be administered locally to the area in need of treatment; this can be achieved by, for example, and not by way of limitation, local infusion during surgery, topical application, for example, in conjunction with a wound dressing after surgery, by injection, by means of a catheter, by means of a suppository, or by means of an implant, said implant being of a porous, non-porous, or gelatinous material, including membranes, such as sialastic membranes, or fibers.

The compound or composition can be delivered in a controlled release system. Furthermore, a controlled release system can be placed in proximity of the therapeutic target, thus requiring only a fraction of the systemic dose (see, e.g., Goodson, in Medical Applications of Controlled Release, supra, vol. 2, pp. 115-138 (1984)). In a further embodiment, a pump may be used. In another embodiment, polymeric materials can be used.

Where the compound of the invention is a nucleic acid encoding a protein, the nucleic acid can be administered in vivo to promote expression of its mRNA and encoded protein, by constructing it as part of an appropriate nucleic acid expression vector and administering, for example, by use of a retroviral vector, or by direct injection, or by use of microparticle bombardment for example, a gene gun, or coating with lipids or cell-surface receptors or transfecting agents, or by administering it in linkage to a homeobox-like peptide which is known to enter the nucleus (see e.g., Joliot et al., Proc. Nati. Acad Sci. USA 88:1864-1868 (1991)). Alternatively, a nucleic acid can be introduced intracellularly and incorporated within host cell DNA for expression, by homologous recombination.

The compounds or pharmaceutical compositions of the invention can be used for treating a bone resorption disease in an individual by down-regulating (i.e., decreasing or inhibiting) in the individual at least one osteoclast marker or informative gene shown to be expressed, or expressed in increased levels (as compared with a control), in individuals having a bone resorption disorder or at risk for developing a bone resorption disorder. The osteoclast markers are informative genes and are selected from the group consisting of the genes in FIGS. 1A-1E. Alternatively, the osteoclast markers are MIP-1γ, CCR1, MIP-1α, RANTES, Brn3a, Brn3b, or Brn3c. In addition, the compounds or pharmaceutical compositions of the invention can be used for treating a bone resorption disease in an individual by up-regulating (i.e., increasing or enhancing) in the individual at least one osteoclast marker shown not to be expressed, or expressed at reduced levels (as compared with a control), in individuals having a bone resorption disorder or at risk for developing a bone resorption disorder. The osteoclast markers are informative genes and are selected from the group consisting of the genes in FIGS. 2A-2B.

The compounds or pharmaceutical compositions of the invention can also be used for treating a bone generating disease in an individual by up-regulating (i.e., increasing) in the individual at least one osteoclast marker shown to be expressed, or expressed in increased levels in osteoclasts (as compared with a control), in individuals having a bone generating disorder or at risk for developing a bone generating disorder. The osteoclast markers are informative genes and are selected from the group consisting of the genes in FIGS. 1A-1E. Alternatively, the osteoclast markers are MIP-1γ, CCR1, MIP-1α, RANTES, Brn3a, Brn3b, or Brn3c. Furthermore, the compounds or pharmaceutical compositions of the invention can be used for treating a bone generating disease in an individual by down-regulating (i.e., decreasing or inhibiting) in the individual at least one osteoclast marker shown not to be expressed, or expressed at reduced levels in osteoclasts (as compared with a control), in individuals having a bone generating disorder or at risk for developing a bone generating disorder. The osteoclast markers are informative genes and are selected from the group consisting of the genes in FIGS. 2A-2B.

The invention further relates to a method of assessing treatment efficacy in an individual having a bone resorption disease, comprising determining the expression level of one or more informative genes at multiple time points, for example, two, three, or more time points during treatment. A treatment can be considered efficacious if the gene expression profile with regard to one or more informative genes tends toward a normal gene expression profile. That is, for example, treatment can be considered efficacious if a gene having increased expression in a disorder (e.g., a bone resorption disease or a bone generating disease) shows reduced expression (i.e., expression tending toward normal expression) or a leveling off of expression as a result of treatment. In addition, treatment can be considered efficacious if a gene having decreased expression in a disorder (e.g., a bone resorption disease or a bone generating disease) shows increased expression (i.e., expression tending toward normal expression) or a leveling off of expression as a result of treatment. For example, in one method, a baseline gene expression profile for the individual can be determined, and repeated gene expression profiles can be determined at time points during treatment. A shift in gene expression profile from a profile correlated with poor treatment outcome to profile correlated with improved treatment outcome is evidence of an effective therapeutic regimen, while a repeated profile correlated with poor treatment outcome is evidence of an ineffective therapeutic regimen. FIGS. 1A-1E and 2A-2B provide gene products that are useful in evaluating the efficacy of treatment of a bone resorption disease or a bone generating disease.

A decrease in expression of the one or more osteoclast markers shown to be expressed, or expressed at increased levels in osteoclasts (as compared with a control), in individuals having a bone resorption disease or at risk for developing a bone resorption disease, is indicative that treatment is effective. Alternatively, a lack of a decrease in expression of the one or more osteoclast markers indicates that the treatment is less effective. The osteoclast markers are informative genes that are selected from the group consisting of the genes in FIGS. 1A-1E. Alternatively, the osteoclast markers are MIP-1γ, CCR1, MIP-1α, RANTES, Brn3a, Brn3b, or Brn3c.

An increase in expression of the one or more osteoclast markers shown not to be expressed, or expressed at reduced levels in osteoclasts (as compared with a control), in individuals having a bone resorption disease or at risk for developing a bone resorption disease, is indicative that treatment is effective. A lack of an increase in expression of the one or more osteoclast markers indicates that the treatment is less effective. The osteoclast markers are informative genes that are selected from the group consisting of the genes in FIGS. 2A-2B.

The invention also relates to a method of assessing treatment efficacy in an individual having a bone generating disease, comprising determining the expression level of one or more informative genes at multiple time points, for example, two, three, or more time points during treatment. An increase in expression of the one or more osteoclast markers shown to be expressed, or expressed at increased levels in osteoclasts (as compared with a control), in individuals having a bone generating disease or at risk for developing a bone generating disease, is indicative that treatment is effective. A lack of an increase in expression of the one or more osteoclast markers indicates that the treatment is less effective. The osteoclast markers are informative genes that are selected from the group consisting of the genes in FIGS. 1A-1E.

A decrease in expression of the one or more osteoclast markers shown not to be expressed, or expressed at reduced levels in osteoclasts (as compared with a control), in individuals having a bone generating disease or at risk for developing a bone generating disease, is indicative that treatment is effective. A lack of a decrease in expression of the one or more osteoclast markers indicates that the treatment is less effective. The osteoclast markers are informative genes that are selected from the group consisting of the genes in FIGS. 2A-2B.

The invention also relates to a solid substrate, for example, an array, having immobilized thereon a plurality of detection agents that can be used to detect expression and/or biological activity of osteoclast markers, such as informative genes or informative gene products. Examples of detection agents include oligonucleotide probes specific for one or more informative genes and polypeptides (gene expression products) encoded by one or more informative genes. Such arrays can be used to carry out methods for identifying and/or diagnosing bone resorption diseases or bone generating diseases, predicting the likelihood of developing such diseases, identifying compounds for use in treating such diseases, and assessing efficacy of treatment of such diseases, as described herein. The osteoclast markers can be informative genes, which are selected from the group consisting of the genes in FIGS. 1A-1E and/or 2A-2B. Osteoclast markers also include MIP-1γ, CCR1, MIP-1α, RANTES, Brn3a, Brn3b, or Brn3c. Polypeptide arrays can be used with antibodies or other polypeptides that bind to the polypeptides encoded by the informative genes. Methods and techniques applicable to array (including protein array) synthesis have been described in PCT Application Nos. WO 00/585 16, and WO 99/36760, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 15 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, which are all incorporated herein by reference in their entirety. Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

The present invention also contemplates many uses for detection agents attached to solid substrates. These uses include gene expression monitoring, profiling, library screening, genotyping and diagnostics. Gene expression monitoring, and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Pat. Nos. 5,856,092, 6,300,063, 5,858,659, 6,284,460, 6,361,947, 6,368,799 and 1564.2006-000 6,333, 179. Other uses are embodied in U.S. Pat. Nos. 5,871,928, 5,902,723, 6,045,996, 5,541,061, and 6,197,506.

The present invention also provides kits that can be used in the above methods. A kit comprises a pharmaceutical composition of the invention in one or more containers. The kit can be a diagnostic kit for use in testing biological samples. The kit can include a control antibody that does not react with the polypeptide of interest in addition to a specific antibody or antigen-binding fragment thereof which binds to the polypeptide (antigen) of the invention being tested for in the biological sample. Such a kit can include a substantially isolated polypeptide antigen comprising an epitope that is specifically immunoreactive with at least one antipolypeptide antigen antibody. Further, such a kit can include a means for detecting the binding of said antibody to the antigen (for example, the antibody may be conjugated to a fluorescent compound such as fluorescein or rhodamine which can be detected by flow cytometry). The kit can include a recombinantly produced or chemically synthesized polypeptide antigen. The polypeptide antigen of the kit can also be attached to a solid support.

The detecting means of the above-described kit includes a solid support to which the polypeptide antigen is attached. The kit can also include a non-attached reporter-labeled anti-human antibody. Binding of the antibody to the polypeptide antigen can be detected by binding of the reporter-labeled antibody. Additionally, the invention includes a diagnostic kit for use in screening serum samples containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. The antibody can be attached to a solid support. The antibody can be a monoclonal antibody. The detecting means of the kit can include a second, labeled monoclonal antibody. Alternatively, or in addition, the detecting means can include a labeled, competing antigen.

In one diagnostic configuration, the test serum sample is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is washed again to remove unbound labeled antibody, and the amount of reporter associated with the reagent is determined. The reporter can be an enzyme, for example, which is detected by incubating the solid phase in the presence of a suitable fluorometric, luminescent or calorimetric substrate, as is standard in the art.

The solid surface reagent in the above assay is prepared by known techniques for attaching protein material to solid support material. Suitable solid support materials include, for example and without limitation, polymeric beads, dip sticks, 96-well plate or filter material.

The invention will be further described with reference to the following non-limiting examples. The teaching of all patents, patent applications and all other publications cited herein are incorporated by reference in their entirety.

EXAMPLES

Example 1

Identification of Osteoclast Markers

Genes were identified that are expressed in bone-resorbing cells (osteoclasts) compared to macrophages that have not been stimulated to differentiate into osteoclasts. Genes that were increased in osteoclasts compared to macrophages and genes that were decreased in osteoclasts compared to macrophages, were identified. RNA was prepared from the two cell systems in which osteoclasts differentiate from macrophages. These cell systems included: 1) RAW 264.7 macrophage-like cell line±RANKL (Receptor Activator of NFκB Ligand); and 2) normal mouse bone marrow macrophages±M-CSF+RANKL (i.e., the cells received both stimulants or neither stimulant). Unstimulated or stimulated cells were extracted for their content of whole cellular RNA after 4 days (RAW 267.4) or 7 days (normal bone marrow) of stimulation. RNA was purified from each extract, was reversed-transcribed, and was labeled for use as 'mixed' cDNA probes. The four mixed probes (RAW 264.7—derived osteoclast probes, RAW 264.7 unstimulated probes; normal bone marrow cell osteoclast probes, and RAW 264.7 unstimulated normal marrow probes) were each hybridized to a set of 3 mouse gene arrays (12,000 genes each) (Affymetrix GENECHIP™ Array Murine Genome U74 version 2 set). Genes that were significantly upregulated, as determined using Affymetrix software (in which for increased expression, p values that approach are most significant) during osteoclast differentiation were identified by differences between RANKL-stimulated and unstimulated probes. Genes that showed significant up-regulation in both cell systems were tabulated. Approximately 280 genes showed increased expression in the macrophages induced to differentiate into osteoclasts compared to their undifferentiated counterparts (listed in FIGS. 1A-1E) and are thus associated with the osteoclast phenotype. In addition, approximately 79 genes were decreased in the macrophages induced to differentiate into osteoclasts compared to their undifferentiated counterparts (listed in FIGS. 2A-2B). These down-regulated genes (in which for decreased expression, p values that approach 1 are most significant) are also associated with the osteoclast bone resorbing phenotype.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of inhibiting an activity of a gene product in a bone cell encoded by osteoclast associated gene OC14 comprising the nucleotide sequence of SEQ ID NO: 50 by administering an antibody that decreases the activity of said gene product by at least 10% in the presence of said antibody, as compared to the activity of said gene product in the absence of said antibody.

2. The method of claim 1, wherein the activity of said gene product is decreased by at least 1.5-fold in the presence of said antibody, as compared to the activity of said gene product in the absence of said antibody.

3. The method of claim 1, wherein the activity of said gene product is decreased by at least 3-fold in the presence of said antibody, as compared to the activity of said gene product in the absence of said antibody.

4. The method of claim 1, wherein the activity of said gene product is decreased by at least 5-fold in the presence of said antibody, as compared to the activity of said gene product in the absence of said antibody.

5. The method of claim 1, wherein the activity of said gene product is decreased by at least 50% in the presence of said antibody, as compared to the activity of said gene product in the absence of said antibody.

6. The method of claim 1, wherein the activity of said gene product is decreased by at least 75% in the presence of said antibody, as compared to the activity of said gene product in the absence of said antibody.

7. The method of claim 1, wherein the activity of said gene product is decreased by at least 90% in the presence of said antibody, as compared to the activity of said gene product in the absence of said antibody.

* * * * *

SEQUENCE LISTING

```
<160> NUMBER OF SEQ ID NOS: 50

<210> SEQ ID NO 1
<211> LENGTH: 22
<212> TYPE: DNA
<213> ORGANISM: Mus musculus

<400> SEQUENCE: 1
gtgttcatca ttggagtggt gg                                    22

<210> SEQ ID NO 2
<211> LENGTH: 23
<212> TYPE: DNA
<213> ORGANISM: Mus musculus
```

```
<400> SEQUENCE: 2
ggttgaacag gtagatgctg gtc                                            23

<210> SEQ ID NO 3
<211> LENGTH: 1118
<212> TYPE: DNA
<213> ORGANISM: Mus musculus

<400> SEQUENCE: 3
gggccagctg gtctgccca ctaagaagat gaagcctttt catactgccc tctccttcct     60
cattcttaca actgctcttg gaatctgggc ccagatcaca catgcaacag agacaaaaga   120
agtccagagc agtctgaagg cacagcaagg gcttgaaatt gaaatgtttc acatgggctt   180
tcaagactct tcagattgct gcctgtccta taactcacgg attcagtgtt caagatttat   240
aggttatttt cccaccagtg gtgggtgtac caggccgggc atcatcttta tcagcaagag   300
ggggttccag gtctgtgcca accccagtga tcggagagtt cagagatgca ttgaaagatt   360
ggagaaaaac tcacaaccac ggacctacaa acaataacat ttgctttaga aagggtgtg    420 aactgccagc tactttcttt ggtcttcccc agtgaccacc taagtggctc taagtgttta   480
tttttatagg tatataaaca ttttttttttt ctgtttccac tttaaagtgg catatctggc   540
tttgtcacag aggggaaact tgtctgtgcc aaccccagtc atctgaaaac tcagatgcct   600
gggaaggtct gaagctgacc tcaatgacta cacataatat ttgattgaga taaatgggca   660
aggtctggag agatggcttg gtggttaaga gcacctgctg ctcttccaga ggacctgggt   720
tcaattccca cttagatggc agctcaaact atctataatt ccaattccaa agaaaactga   780
tgccctattt tgccccttta gttagtagta tttacagtat tctttataaa ttcaccttga   840
catgaccatc ttgagctaca gccatcctaa ctgcctcaga atcactcaag ttcttccact   900
cggtttccca gcggatttta agtggataaa ctgtgagagt ggtctgtggg actttggaat   960
gtgtctggtt ctgatagtca cttatggcaa cccaggtaca ttcaactagg atgaaataaa  1020
ttctgcctta gcccagtagt atgtctgtgt ttgtaaggac ccagctgatt ttcccaccac  1080
ccctccatca gtccgccact aataaagtgc atctatgc                          1118

<210> SEQ ID NO 4
<211> LENGTH: 122
<212> TYPE: PRT
<213> ORGANISM: Mus musculus

<400> SEQUENCE: 4

Met Lys Pro Phe His Thr Ala Leu Ser Phe Leu Ile Leu Thr Thr Ala
1               5                   10                  15

Leu Gly Ile Trp Ala Gln Ile Thr His Ala Thr Glu Thr Lys Glu Val
            20                  25                  30

Gln Ser Ser Leu Lys Ala Gln Gln Gly Leu Glu Ile Glu Met Phe His
        35                  40                  45

Met Gly Phe Gln Asp Ser Ser Asp Cys Cys Leu Ser Tyr Asn Ser Arg
    50                  55                  60

Ile Gln Cys Ser Arg Phe Ile Gly Tyr Phe Pro Thr Ser Gly Gly Cys
65                  70                  75                  80

Thr Arg Pro Gly Ile Ile Phe Ile Ser Lys Arg Gly Phe Gln Val Cys
                85                  90                  95

Ala Asn Pro Ser Asp Arg Arg Val Gln Arg Cys Ile Glu Arg Leu Glu
            100                 105                 110

Lys Asn Ser Gln Pro Arg Thr Tyr Lys Gln
```

<210> SEQ ID NO 5
<211> LENGTH: 2156
<212> TYPE: DNA
<213> ORGANISM: Homo sapiens

<400> SEQUENCE: 5

```
ggcacgagcc cagaaacaaa gacttcacgg acaaagtccc ttggaaccag agagaagccg      60
ggatggaaac tccaaacacc acagaggact atgacacgac cacagagttt gactatgggg     120
atgcaactcc gtgccagaag gtgaacgaga gggcctttgg ggcccaactg ctgcccctc      180
tgtactcctt ggtatttgtc attggcctgg ttggaaacat cctggtggtc ctggtccttg     240
tgcaatacaa gaggctaaaa aacatgacca gcatctacct cctgaacctg gccatttctg     300
acctgctctt cctgttcacg cttcccttct ggatcgacta caagttgaag gatgactggg     360
ttttggtga tgccatgtgt aagatcctct ctgggtttta ttacacaggc ttgtacagcg     420
agatctttt catcatcctg ctgacgattg acaggtacct ggccatcgtc cacgccgtgt     480
ttgccttgcg ggcacggacc gtcactttg gtgtcatcac cagcatcatc atttgggccc     540
tggccatctt ggcttccatg ccaggcttat acttttccaa gacccaatgg gaattcactc     600
accacacctg cagccttcac tttcctcacg aaagcctacg agagtggaag ctgtttcagg     660
ctctgaaact gaacctcttt gggctggtat tgcctttgtt ggtcatgatc atctgctaca     720
cagggattat aaagattctg ctaagacgac caaatgagaa gaaatccaaa gctgtccgtt     780
tgattttgt catcatgatc atcttttttc tcttttggac ccctacaat ttgactatac     840
ttatttctgt tttccaagac ttcctgttca cccatgagtg tgagcagagc agacatttgg     900
acctggctgt gcaagtgacg gaggtgatcg cctacacgca ctgctgtgtc aacccagtga     960
tctacgcctt cgttggtgag aggttccgga agtacctgcg gcagttgttc acaggcgtg    1020
tggctgtgca cctggttaaa tggctcccct tcctctccgt ggacaggctg agagggtca    1080
gctccacatc tccctccaca ggggagcatg aactctctgc tgggttctga ctcagaccat    1140
aggaggccaa cccaaaataa gcaggcgtga cctgccaggc acactgagcc agcagcctgg    1200
ctctcccagc caggttctga ctcttggcac agcatggagt cacagccact gggatagag    1260
agggaatgta atggtggcct ggggcttctg aggcttctgg ggcttcagtc ttttccatga    1320
acttctcccc tggtagaaag aagatgaatg agcaaaacca aatattccag agactgggac    1380
taagtgtacc agaaagggc ttggactcaa gcaagatttc agatttgtga ccattagcat    1440
ttgtcaacaa agtcacccac ttcccactat tgcttgcaca aaccaattaa acccagtagt    1500
ggtgactgtg ggctccattc aaagtgagct cctaagccat gggagacact gatgtatgag    1560
gaatttctgt tcttccatca cctccccccc ccgccaccc tcccactgcc aagaacttgg    1620
aaatagtgat ttcacagtg actccactct gagtcccaga gccaatcagt agccagcatc    1680
tgcctcccct tcactcccac cgcaggattt gggctcttgg aatcctgggg aacatagaac    1740
tcatgacgga agagttgaga cctaacgaga aatagaaatg ggggaactac tgctggcagt    1800
ggaactaaga aagcccttag gaagaatttt tatatccact aaaatcaaac aattcaggga    1860
gtgggctaag cacgggccat atgaataaca tggtgtgctt cttaaaatag ccataaaggg    1920
gagggactca tcatttccat ttacccttct tttctgacta tttttcagaa tctctcttct    1980
tttcaagttg ggtgatatgt tggtagattc taatggcttt attgcagcga ttaataacag    2040
gcaaaaggaa gcagggttgg tttcccttct ttttgttctt catctaagcc ttctggtttt    2100
```

```
atgggtcaga gttccgactg ccatcttgga cttgtcagca aaaaaaaaaa aaaaaa    2156
```

<210> SEQ ID NO 6
<211> LENGTH: 355
<212> TYPE: PRT
<213> ORGANISM: Homo sapiens

<400> SEQUENCE: 6

```
Met Glu Thr Pro Asn Thr Thr Glu Asp Tyr Asp Thr Thr Thr Glu Phe
  1               5                  10                  15

Asp Tyr Gly Asp Ala Thr Pro Cys Gln Lys Val Asn Glu Arg Ala Phe
             20                  25                  30

Gly Ala Gln Leu Leu Pro Pro Leu Tyr Ser Leu Val Phe Val Ile Gly
         35                  40                  45

Leu Val Gly Asn Ile Leu Val Val Leu Val Leu Val Gln Tyr Lys Arg
 50                  55                  60

Leu Lys Asn Met Thr Ser Ile Tyr Leu Leu Asn Leu Ala Ile Ser Asp
 65                  70                  75                  80

Leu Leu Phe Leu Phe Thr Leu Pro Phe Trp Ile Asp Tyr Lys Leu Lys
                 85                  90                  95

Asp Asp Trp Val Phe Gly Asp Ala Met Cys Lys Ile Leu Ser Gly Phe
            100                 105                 110

Tyr Tyr Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
130                 135                 140

Arg Thr Val Thr Phe Gly Val Ile Thr Ser Ile Ile Trp Ala Leu
145                 150                 155                 160

Ala Ile Leu Ala Ser Met Pro Gly Leu Tyr Phe Ser Lys Thr Gln Trp
                165                 170                 175

Glu Phe Thr His His Thr Cys Ser Leu His Phe Pro His Glu Ser Leu
            180                 185                 190

Arg Glu Trp Lys Leu Phe Gln Ala Leu Lys Leu Asn Leu Phe Gly Leu
        195                 200                 205

Val Leu Pro Leu Leu Val Met Ile Ile Cys Tyr Thr Gly Ile Ile Lys
    210                 215                 220

Ile Leu Leu Arg Arg Pro Asn Glu Lys Lys Ser Lys Ala Val Arg Leu
225                 230                 235                 240

Ile Phe Val Ile Met Ile Ile Phe Phe Leu Phe Trp Thr Pro Tyr Asn
                245                 250                 255

Leu Thr Ile Leu Ile Ser Val Phe Gln Asp Phe Leu Phe Thr His Glu
            260                 265                 270

Cys Glu Gln Ser Arg His Leu Asp Leu Ala Val Gln Val Thr Glu Val
        275                 280                 285

Ile Ala Tyr Thr His Cys Cys Val Asn Pro Val Ile Tyr Ala Phe Val
    290                 295                 300

Gly Glu Arg Phe Arg Lys Tyr Leu Arg Gln Leu Phe His Arg Arg Val
305                 310                 315                 320

Ala Val His Leu Val Lys Trp Leu Pro Phe Leu Ser Val Asp Arg Leu
                325                 330                 335

Glu Arg Val Ser Ser Thr Ser Pro Ser Thr Gly Glu His Glu Leu Ser
            340                 345                 350

Ala Gly Phe
        355
```

```
<210> SEQ ID NO 7
<211> LENGTH: 2156
<212> TYPE: DNA
<213> ORGANISM: Homo sapiens

<400> SEQUENCE: 7
ggcacgagcc cagaaacaaa gacttcacgg acaaagtccc ttggaaccag agagaagccg      60
ggatggaaac tccaaacacc acagaggact atgacacgac cacagagttt gactatgggg     120
atgcaactcc gtgccagaag gtgaacgaga gggcctttgg ggcccaactg ctgcccctc     180 tgtactcctt ggtatttgtc attggcctgg ttggaaacat cctggtggtc ctggtccttg     240
tgcaatacaa gaggctaaaa aacatgacca gcatctacct cctgaacctg gccatttctg     300
acctgctctt cctgttcacg cttcccttct ggatcgacta caagttgaag gatgactggg     360 ttttggtga tgccatgtgt aagatcctct ctgggtttta ttacacaggc ttgtacagcg     420 agatctttt catcatcctg ctgacgattg acaggtacct ggccatcgtc cacgccgtgt     480
ttgccttgcg ggcacggacc gtcactttg gtgtcatcac cagcatcatc atttgggccc     540
tggccatctt ggcttccatg ccaggcttat acttttccaa gacccaatgg gaattcactc     600
accacacctg cagccttcac tttcctcacg aaagcctacg agagtggaag ctgtttcagg     660
ctctgaaact gaacctcttt gggctggtat tgcctttgtt ggtcatgatc atctgctaca     720
cagggattat aaagattctg ctaagacgac caaatgagaa gaaatccaaa gctgtccgtt     780 tgattttgt catcatgatc atctttttc tcttttggac cccctacaat ttgactatac     840
ttatttctgt tttccaagac ttcctgttca cccatgagtg tgagcagagc agacatttgg     900
acctggctgt gcaagtgacg gaggtgatcg cctacacgca ctgctgtgtc aacccagtga     960
tctacgcctt cgttggtgag aggttccgga agtacctgcg gcagttgttc cacaggcgtg    1020
tggctgtgca cctggttaaa tggctccct tcctctccgt ggacaggctg gagagggtca    1080
gctccacatc tccctccaca ggggagcatg aactctctgc tgggttctga ctcagaccat    1140
aggaggccaa cccaaaataa gcaggcgtga cctgccaggc acactgagcc agcagcctgg    1200
ctctcccagc caggttctga ctcttggcac agcatggagt cacagccact tgggatagag    1260
agggaatgta atggtggcct ggggcttctg aggcttctgg ggcttcagtc ttttccatga    1320
acttctcccc tggtagaaag aagatgaatg agcaaaacca atattccag agactgggac    1380 taagtgtacc agagaagggc ttggactcaa gcaagatttc agatttgtga ccattagcat    1440
ttgtcaacaa agtcacccac ttcccactat tgcttgcaca aaccaattaa acccagtagt    1500
ggtgactgtg ggctccattc aaagtgagct cctaagccat gggagacact gatgtatgag    1560
gaatttctgt tcttccatca cctccccccc ccgccaccc tcccactgcc aagaacttgg    1620
aaatagtgat ttccacagtg actccactct gagtcccaga gccaatcagt agccagcatc    1680
tgcctcccct tcactcccac cgcaggattt gggctcttgg aatcctgggg aacatagaac    1740
tcatgacgga agagttgaga cctaacgaga aatagaaatg ggggaactac tgctggcagt    1800
ggaactaaga aagcccttag gaagaatttt tatatccact aaaatcaaac aattcaggga    1860
gtgggctaag cacgggccat atgaataaca tggtgtgctt cttaaaatag ccataaaggg    1920
gagggactca tcatttccat ttaccctct tttctgacta ttttcagaa tctctcttct    1980 tttcaagttg ggtgatatgt tggtagattc taatggcttt attgcagcga ttaataacag    2040
gcaaaaggaa gcagggttgg tttcccttct ttttgttctt catctaagcc ttctggtttt    2100
atgggtcaga gttccgactg ccatcttgga cttgtcagca aaaaaaaaaa aaaaaa       2156
```

<210> SEQ ID NO 8
<211> LENGTH: 355
<212> TYPE: PRT
<213> ORGANISM: Homo sapiens

<400> SEQUENCE: 8

Met Glu Thr Pro Asn Thr Thr Glu Asp Tyr Asp Thr Thr Glu Phe
1               5                   10                  15

Asp Tyr Gly Asp Ala Thr Pro Cys Gln Lys Val Asn Glu Arg Ala Phe
            20                  25                  30

Gly Ala Gln Leu Leu Pro Pro Leu Tyr Ser Leu Val Phe Val Ile Gly
        35                  40                  45

Leu Val Gly Asn Ile Leu Val Val Leu Val Leu Val Gln Tyr Lys Arg
    50                  55                  60

Leu Lys Asn Met Thr Ser Ile Tyr Leu Leu Asn Leu Ala Ile Ser Asp
65                  70                  75                  80

Leu Leu Phe Leu Phe Thr Leu Pro Phe Trp Ile Asp Tyr Lys Leu Lys
                85                  90                  95

Asp Asp Trp Val Phe Gly Asp Ala Met Cys Lys Ile Leu Ser Gly Phe
            100                 105                 110

Tyr Tyr Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
130                 135                 140

Arg Thr Val Thr Phe Gly Val Ile Thr Ser Ile Ile Ile Trp Ala Leu
145                 150                 155                 160

Ala Ile Leu Ala Ser Met Pro Gly Leu Tyr Phe Ser Lys Thr Gln Trp
                165                 170                 175

Glu Phe Thr His His Thr Cys Ser Leu His Phe Pro His Glu Ser Leu
            180                 185                 190

Arg Glu Trp Lys Leu Phe Gln Ala Leu Lys Leu Asn Leu Phe Gly Leu
        195                 200                 205

Val Leu Pro Leu Leu Val Met Ile Ile Cys Tyr Thr Gly Ile Ile Lys
    210                 215                 220

Ile Leu Leu Arg Arg Pro Asn Glu Lys Lys Ser Lys Ala Val Arg Leu
225                 230                 235                 240

Ile Phe Val Ile Met Ile Ile Phe Phe Leu Phe Trp Thr Pro Tyr Asn
                245                 250                 255

Leu Thr Ile Leu Ile Ser Val Phe Gln Asp Phe Leu Phe Thr His Glu
            260                 265                 270

Cys Glu Gln Ser Arg His Leu Asp Leu Ala Val Gln Val Thr Glu Val
        275                 280                 285

Ile Ala Tyr Thr His Cys Cys Val Asn Pro Val Ile Tyr Ala Phe Val
    290                 295                 300

Gly Glu Arg Phe Arg Lys Tyr Leu Arg Gln Leu Phe His Arg Val
305                 310                 315                 320

Ala Val His Leu Val Lys Trp Leu Pro Phe Leu Ser Val Asp Arg Leu
                325                 330                 335

Glu Arg Val Ser Ser Thr Ser Pro Ser Thr Gly Glu His Glu Leu Ser
            340                 345                 350

Ala Gly Phe
        355

<210> SEQ ID NO 9
<211> LENGTH: 309
<212> TYPE: DNA

-continued

```
<213> ORGANISM: Homo sapiens

<400> SEQUENCE: 9
accatgaagg tctccgcggc agccctcgct gtcatcctca ttgctactgc cctctgcgct      60
cctgcatctg cctccccata ttcctcggac accacaccct gctgctttgc ctacattgcc     120
cgcccactgc cccgtgccca catcaaggag tatttctaca ccagtggcaa gtgctccaac     180
ccagcagtcg tctttgtcac ccgaaagaac cgccaagtgt gtgccaaccc agagaagaaa     240
tgggttcggg agtacatcaa ctctttggag atgagctagg atggagagtc cttgaacctg     300
aacttacac                                                            309

<210> SEQ ID NO 10
<211> LENGTH: 91
<212> TYPE: PRT
<213> ORGANISM: Homo sapiens

<400> SEQUENCE: 10

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
            20                  25                  30

Cys Cys Phe Ala Tyr Ile Ala Arg Pro Leu Pro Arg Ala His Ile Lys
        35                  40                  45

Glu Tyr Phe Tyr Thr Ser Gly Lys Cys Ser Asn Pro Ala Val Val Phe
    50                  55                  60

Val Thr Arg Lys Asn Arg Gln Val Cys Ala Asn Pro Glu Lys Lys Trp
65                  70                  75                  80

Val Arg Glu Tyr Ile Asn Ser Leu Glu Met Ser
                85                  90

<210> SEQ ID NO 11
<211> LENGTH: 10
<212> TYPE: DNA
<213> ORGANISM: Homo sapiens

<400> SEQUENCE: 11
actcattaat                                                            10

<210> SEQ ID NO 12
<211> LENGTH: 10
<212> TYPE: DNA
<213> ORGANISM: Homo sapiens

<400> SEQUENCE: 12
actcattaac                                                            10

<210> SEQ ID NO 13
<211> LENGTH: 10
<212> TYPE: DNA
<213> ORGANISM: Homo sapiens

<400> SEQUENCE: 13
gctcattaat                                                            10

<210> SEQ ID NO 14
<211> LENGTH: 10
<212> TYPE: DNA
<213> ORGANISM: Homo sapiens

<400> SEQUENCE: 14
```

-continued

```
gctcattaac                                                          10

<210> SEQ ID NO 15
<211> LENGTH: 0
<212> TYPE: DNA
<213> ORGANISM: No Sequence Data

<400> SEQUENCE: 15

000

<210> SEQ ID NO 16
<211> LENGTH: 18
<212> TYPE: DNA
<213> ORGANISM: Homo sapiens

<400> SEQUENCE: 16
cacagctcat taacgcgc                                                 18

<210> SEQ ID NO 17
<211> LENGTH: 18
<212> TYPE: DNA
<213> ORGANISM: Homo sapiens

<400> SEQUENCE: 17
gtgtcgagta attgcgcg                                                 18

<210> SEQ ID NO 18
<211> LENGTH: 22
<212> TYPE: DNA
<213> ORGANISM: Homo sapiens

<400> SEQUENCE: 18
gccaacctca agatcccggg cg                                            22

<210> SEQ ID NO 19
<211> LENGTH: 22
<212> TYPE: DNA
<213> ORGANISM: Homo sapiens

<400> SEQUENCE: 19
ccagtttctc ggcgatggcg gc                                            22

<210> SEQ ID NO 20
<211> LENGTH: 20
<212> TYPE: DNA
<213> ORGANISM: Homo sapiens

<400> SEQUENCE: 20
cacggtggtg tccactccgg                                               20

<210> SEQ ID NO 21
<211> LENGTH: 20
<212> TYPE: DNA
<213> ORGANISM: Homo sapiens

<400> SEQUENCE: 21
ccgcgatctt ctccgaggag                                               20

<210> SEQ ID NO 22
<211> LENGTH: 28
<212> TYPE: DNA
<213> ORGANISM: Homo sapiens

<400> SEQUENCE: 22
```

```
ggccatgaac gccaagcagc ctttcggc                                              28

<210> SEQ ID NO 23
<211> LENGTH: 28
<212> TYPE: DNA
<213> ORGANISM: Homo sapiens

<400> SEQUENCE: 23
gcgcctagat gatgcgggtg gatctgcg                                              28

<210> SEQ ID NO 24
<211> LENGTH: 21
<212> TYPE: DNA
<213> ORGANISM: Homo sapiens

<400> SEQUENCE: 24
gaccgcttct ccaagcacga c                                                    21

<210> SEQ ID NO 25
<211> LENGTH: 20
<212> TYPE: DNA
<213> ORGANISM: Homo sapiens

<400> SEQUENCE: 25
ctgcgccggt gctgttgtag                                                      20

<210> SEQ ID NO 26
<211> LENGTH: 18
<212> TYPE: DNA
<213> ORGANISM: Homo sapiens

<400> SEQUENCE: 26
cacagctcat taacgcgc                                                        18

<210> SEQ ID NO 27
<211> LENGTH: 18
<212> TYPE: DNA
<213> ORGANISM: Homo sapiens

<400> SEQUENCE: 27
gcgcgttaat gagctgtg                                                        18

<210> SEQ ID NO 28
<211> LENGTH: 18
<212> TYPE: DNA
<213> ORGANISM: Artificial
<220> FEATURE:
<223> OTHER INFORMATION: Primer to Generate Mutated Sequence

<400> SEQUENCE: 28
gcgcgttgct gagctctg                                                        18

<210> SEQ ID NO 29
<211> LENGTH: 18
<212> TYPE: DNA
<213> ORGANISM: Artificial
<220> FEATURE:
<223> OTHER INFORMATION: Primer to Generate Mutated Sequence

<400> SEQUENCE: 29
cagagctcag caacgcgc                                                        18

<210> SEQ ID NO 30
<211> LENGTH: 2160
<212> TYPE: DNA
```

<213> ORGANISM: Mus sp.

<400> SEQUENCE: 30

```
gagcagtgcg agcgagcgca cgctcgggac ggaggccggg cgagccggcg tgcgcacttt      60
gccgcggact ttgcgagtgt tttgtggatt tttacatgcc aaggcgccaa gatgatgtcc     120
atgaacagca agcagcctca ctttgccatg catcccaccc tccctgagca caagtacccg     180
tcgctgcact ccagctccga ggccatccgg cgggcctgcc tgcccacgcc gccggtaagc     240
gccccacgcc gcggccccgg tcccggcccg cgcgctcgcc ccctcccgcg tccgcgggtg     300
gcggcagctg ccccgggcgg ctccgggccg ctcgcgggcg ggactgctct tagagggatc     360
ccgctgccag gcacgcgtgg cccggggccg ctggaggccc gggtcccatc cgcctgtgcc     420
tctgtccagc gcctgccatc cgcggggagc tctcggggccg cggctgtcga cttggctcca     480
cttgtcggt taattttacg cctgcacaag gcgatctctg ctcgctcgct cgctcgctcg     540
ctcgctcgct cgctttctcg ttcgggtgtg tggcacgggt ccttagcttc gagtgacatc     600
tccatttctt ctttttcttc ttcttttcgc tcttttttgt cgtctcccac tgtcttcccc     660
ggaatgtgtt tccgtgtgcg tccccttcta cccttccctg gcctgtgcc tctcccttc     720
tatttcccccc accccggcat gttctcaaat cgtccccggg tcctccgttg accctgctct     780
tcccacccccc cgttgttatt ttggtcgctt tgtgttttgc cttttgcccg tgctttcctg     840
cttgtgtgtt tgttttgtgg tttctttggt gtttgtcccc ccttttttct ttttttttct     900
ttttctttct tcttttttttt ttcttttcctt ttcttttggg tttggtttgt gtcgcctgca     960
gctgcagagc aacctcttcg ccagcctgga cgagacgctg ctggcgcggg ccgaggcgct    1020
ggcggccgtg gacatcgcgg tgtcccaggg caagagccac cctttcaagc cggacgccac    1080
gtaccacacg atgaatagcg tgccctgcac gtccacgtcc accgtgccgc tggcgcacca    1140
ccaccaccac caccaccacc accaggcgct cgagccggt gacctgctgg accacatctc    1200
gtcgccgtcg ctcgcgctca tggccggcgc agggggcgca ggcgcggcgg gaggcggcgg    1260
cggcgcccac gacggccccg ggggcggagg cggaccgggg ggcggcggtg cccgggcgg    1320
cggcggcccc ggggtggcg gcggcggcgg cggcccgggg ggcggcggcg cgccccggg    1380
cggcgggctc ttgggcggct cggcgcatcc gcacccgcac atgcacggcc tgggccacct    1440
gtcgcacccc gcggcggcgg cggccatgaa catgccgtcc gggctgccgc atcccgggct    1500
cgtggccgcg gcggcgcacc acggcgcggc ggcggcagcg gcggcggcgg cggcggggca    1560
ggtggcggcg gcgtcggccg cggcggcggt ggtgggcgcg gcgggcctgg cgtccatctg    1620
cgactcggac acggacccgc gcgagctcga ggcgttcgcc gagcgcttca gcagcggcg    1680
catcaagctg ggcgtgacgc aggccgacgt gggctcggcg ctggccaacc tcaagatccc    1740
gggcgtgggc tcgctcagcc agagcaccat ctgcaggttc gagtcgctca cgctctcgca    1800
caacaacatg atcgcgctca gcccatcct gcaggcgtgg ctggaggagg ccgagggcgc    1860
gcagcgtgag aaaatgaaca gccggagct cttcaacggc ggcgagaaga agcgcaagcg    1920
gacttccatc gccgcgcccg agaagcgctc cctcgaggcc tattttgccg tacaaccccg    1980
gccctcgtct gagaagatcg ccgccatcgc cgagaaactg gacctcaaaa agaacgtggt    2040
gcgggtgtgg ttttgcaacc agagacagaa gcagaagcgc atgaaattct ctgccactta    2100
ctgaggaggg tgtgagacgc cgggtgggc acactgggga gctgagggt gcgtttctgg    2160
```

<210> SEQ ID NO 31
<211> LENGTH: 421
<212> TYPE: PRT

<213> ORGANISM: Mus sp.

<400> SEQUENCE: 31

Met Met Ser Met Asn Ser Lys Gln Pro His Phe Ala Met His Pro Thr
1               5                   10                  15

Leu Pro Glu His Lys Tyr Pro Ser Leu His Ser Ser Glu Ala Ile
            20                  25                  30

Arg Arg Ala Cys Leu Pro Thr Pro Pro Leu Gln Ser Asn Leu Phe Ala
        35                  40                  45

Ser Leu Asp Glu Thr Leu Leu Ala Arg Ala Glu Ala Leu Ala Ala Val
    50                  55                  60

Asp Ile Ala Val Ser Gln Gly Lys Ser His Pro Phe Lys Pro Asp Ala
65                  70                  75                  80

Thr Tyr His Thr Met Asn Ser Val Pro Cys Thr Ser Thr Ser Thr Val
                85                  90                  95

Pro Leu Ala His His His His His His His His Gln Ala Leu Glu
            100                 105                 110

Pro Gly Asp Leu Leu Asp His Ile Ser Ser Pro Ser Leu Ala Leu Met
        115                 120                 125

Ala Gly Ala Gly Gly Ala Gly Ala Ala Gly Gly Gly Gly Ala His
130                 135                 140

Asp Gly Pro Gly Gly Gly Gly Pro Gly Gly Gly Gly Pro Gly
145                 150                 155                 160

Gly Gly Gly Pro Gly Gly Gly Gly Gly Gly Pro Gly Gly Gly
                165                 170                 175

Gly Gly Ala Pro Gly Gly Gly Leu Leu Gly Gly Ser Ala His Pro His
            180                 185                 190

Pro His Met His Gly Leu Gly His Leu Ser His Pro Ala Ala Ala
        195                 200                 205

Ala Met Asn Met Pro Ser Gly Leu Pro His Pro Gly Leu Val Ala Ala
210                 215                 220

Ala Ala His His Gly Ala Ala Ala Ala Ala Ala Ala Ala Gly
225                 230                 235                 240

Gln Val Ala Ala Ala Ser Ala Ala Ala Val Val Gly Ala Ala Gly
                245                 250                 255

Leu Ala Ser Ile Cys Asp Ser Asp Thr Asp Pro Arg Glu Leu Glu Ala
            260                 265                 270

Phe Ala Glu Arg Phe Lys Gln Arg Arg Ile Lys Leu Gly Val Thr Gln
        275                 280                 285

Ala Asp Val Gly Ser Ala Leu Ala Asn Leu Lys Ile Pro Gly Val Gly
    290                 295                 300

Ser Leu Ser Gln Ser Thr Ile Cys Arg Phe Glu Ser Leu Thr Leu Ser
305                 310                 315                 320

His Asn Asn Met Ile Ala Leu Lys Pro Ile Leu Gln Ala Trp Leu Glu
                325                 330                 335

Glu Ala Glu Gly Ala Gln Arg Glu Lys Met Asn Lys Pro Glu Leu Phe
            340                 345                 350

Asn Gly Gly Glu Lys Lys Arg Lys Arg Thr Ser Ile Ala Ala Pro Glu
        355                 360                 365

Lys Arg Ser Leu Glu Ala Tyr Phe Ala Val Gln Pro Arg Pro Ser Ser
    370                 375                 380

Glu Lys Ile Ala Ala Ile Ala Glu Lys Leu Asp Leu Lys Lys Asn Val
385                 390                 395                 400

Val Arg Val Trp Phe Cys Asn Gln Arg Gln Lys Gln Lys Arg Met Lys

```
                     405                 410                 415
Phe Ser Ala Thr Tyr
            420

<210> SEQ ID NO 32
<211> LENGTH: 123
<212> TYPE: DNA
<213> ORGANISM: Homo sapiens

<400> SEQUENCE: 32
atgatgtcca tgaacagcaa gcagcctcac tttgccatgc atcccaccct ccctgagcac      60
aagtacccgt cgctgcactc cagctccgag gccatccggg gggcctgcct gcccacgccg     120
ccg                                                                   123

<210> SEQ ID NO 33
<211> LENGTH: 1149
<212> TYPE: DNA
<213> ORGANISM: Homo sapiens

<400> SEQUENCE: 33
ctgcagagca acctcttcgc cagcctggac gagacgctgc tggcgcgggc cgaggcgctg      60
gcggccgtgg acatcgccgt gtcccagggc aagagccatc ctttcaagcc ggacgccacg     120
taccacacga tgaacagcgt gccgtgcacg tccacttcca cggtgcctct gcggcaccac     180
caccaccacc accaccacca ccaggcgctc gaacccggcg atctgctgga ccacatctcc     240
tcgccgtcgc tcgcgctcat ggccggcgcg ggcggcgcgg gcggcgcggg cgcggcggcc     300
ggcggcggcg gcgcccacga cggcccgggg ggcggtggcg gcccgggcgg cggcggcggc     360
ccgggcggcg gcgccccgg gggaggcggc ggtggcggcc cggggggcgg cggcggcggc     420
ccgggcggcg ggctcctggg cggctccgcg caccctcacc cgcatatgca cagcctgggc     480
cacctgtcgc accccgcggc ggcggccgcc atgaacatgc cgtccgggct gccgcaccc      540 gggctggtgg cggcggcggc gcaccacggc gcggcagcgg cagcggcggc ggcggcggcc     600
gggcaggtgg cagcggcatc ggcggcggcg ccgtggtgg cgcagcgggg cctggcgtcc     660
atctgcgact cggacacgga cccgcgcgag ctcgaggcgt tcgcggagcg cttcaagcag     720
cggcgcatca gctgggcgt gacgcaggcc gacgtgggct cggcgctggc caacctcaag     780
atcccgggcg tgggctcact cagccagagc accatctgca ggttcgagtc gctcacgctc     840
tcgcacaaca acatgatcgc gctcaagccc atcctgcagg cgtggctcga ggaggccgag     900
ggcgcccagc gcgagaaaat gaacaagcct gagctcttca cggcggcga aagaagcgc     960 aagcggactt ccatcgccgc gcccgagaag cgctccctcg aggcctactt cgccgtgcag    1020
ccccggccct cgtccgagaa gatcgccgcc atcgccgaga aactggacct caaaaagaac    1080
gtggtgcggg tgtggttttg caaccagaga cagaagcaga agcggatgaa attctctgcc    1140
acttactga                                                            1149

<210> SEQ ID NO 34
<211> LENGTH: 423
<212> TYPE: PRT
<213> ORGANISM: Homo sapiens

<400> SEQUENCE: 34

Met Met Ser Met Asn Ser Lys Gln Pro His Phe Ala Met His Pro Thr
1               5                   10                  15

Leu Pro Glu His Lys Tyr Pro Ser Leu His Ser Ser Glu Ala Ile
            20                  25                  30
```

```
Arg Arg Ala Cys Leu Pro Thr Pro Pro Leu Gln Ser Asn Leu Phe Ala
         35                  40                  45
Ser Leu Asp Glu Thr Leu Leu Ala Arg Ala Glu Ala Leu Ala Ala Val
 50                  55                  60
Asp Ile Ala Val Ser Gln Gly Lys Ser His Pro Phe Lys Pro Asp Ala
65                  70                  75                  80
Thr Tyr His Thr Met Asn Ser Val Pro Cys Thr Ser Thr Ser Thr Val
                 85                  90                  95
Pro Leu Arg His His His His His His His His Gln Ala Leu Glu
                100                 105                 110
Pro Gly Asp Leu Leu Asp His Ile Ser Ser Pro Ser Leu Ala Leu Met
            115                 120                 125
Ala Gly Ala Gly Gly Ala Gly Gly Ala Gly Ala Ala Gly Gly Gly
        130                 135                 140
Gly Ala His Asp Gly Pro Gly Gly Gly Gly Pro Gly Gly Gly Gly
145                 150                 155                 160
Gly Pro Gly Gly Gly Gly Pro Gly Gly Gly Gly Gly Gly Pro Gly
                165                 170                 175
Gly Gly Gly Gly Pro Gly Gly Gly Leu Leu Gly Gly Ser Ala His
            180                 185                 190
Pro His Pro His Met His Ser Leu Gly His Leu Ser His Pro Ala Ala
        195                 200                 205
Ala Ala Ala Met Asn Met Pro Ser Gly Leu Pro His Pro Gly Leu Val
    210                 215                 220
Ala Ala Ala Ala His His Gly Ala Ala Ala Ala Ala Ala Ala Ala
225                 230                 235                 240
Ala Gly Gln Val Ala Ala Ser Ala Ala Ala Val Val Gly Ala
                245                 250                 255
Ala Gly Leu Ala Ser Ile Cys Asp Ser Asp Thr Asp Pro Arg Glu Leu
            260                 265                 270
Glu Ala Phe Ala Glu Arg Phe Lys Gln Arg Arg Ile Lys Leu Gly Val
        275                 280                 285
Thr Gln Ala Asp Val Gly Ser Ala Leu Ala Asn Leu Lys Ile Pro Gly
    290                 295                 300
Val Gly Ser Leu Ser Gln Ser Thr Ile Cys Arg Phe Glu Ser Leu Thr
305                 310                 315                 320
Leu Ser His Asn Asn Met Ile Ala Leu Lys Pro Ile Leu Gln Ala Trp
                325                 330                 335
Leu Glu Glu Ala Glu Gly Ala Gln Arg Glu Lys Met Asn Lys Pro Glu
            340                 345                 350
Leu Phe Asn Gly Gly Glu Lys Lys Arg Lys Arg Thr Ser Ile Ala Ala
        355                 360                 365
Pro Glu Lys Arg Ser Leu Glu Ala Tyr Phe Ala Val Gln Pro Arg Pro
    370                 375                 380
Ser Ser Glu Lys Ile Ala Ala Ile Ala Glu Lys Leu Asp Leu Lys Lys
385                 390                 395                 400
Asn Val Val Arg Val Trp Phe Cys Asn Gln Arg Gln Lys Gln Lys Arg
                405                 410                 415
Met Lys Phe Ser Ala Thr Tyr
            420

<210> SEQ ID NO 35
<211> LENGTH: 1091
<212> TYPE: DNA
```

<213> ORGANISM: Mus musculus

<400> SEQUENCE: 35

```
tttcaggatc actgtcatta ttattatttt aacgttctgg gaatgctgta ggcacggtgg      60
cggtggcgag ccctgggccg ggggcttccg gagagagcgc tcacaattcc ctgctgagcg     120
taatgtgtgc cttctactta caattgcaga gcaatatatt cggcgggctg gatgagagtc     180
tgctggcccg tgccgaggct ctggccgccg tggacatcgt ctcccagagt aagagccacc     240
accaccatcc gccccaccac agccccttca agccggacgc cacttaccac accatgaaca     300
ccatcccgtg cacgtcggca gcctcctctt cttctgtgcc catctcgcac ccgtccgctc     360
tggctggcac ccatcaccac caccaccacc accatcacca ccatcaccag ccgcaccagg     420
cgctggaggg cgagctgctt gagcacctaa gccccgggct ggccctggga gctatggcgg     480
gccccgacgg cacggtggtg tccactccgg ctcacgcacc acacatggcc accatgaacc     540
ccatgcacca agcagccctg agcatggccc acgcacatgg gctgccctca cacatgggct     600
gcatgagcga cgtggatgca gacccgcggg acctggaggc gttcgccgag cgtttcaagc     660
agcgacgcat caagctggga gtgacccagg cagatgtggg ctcggcgctg gccaacctca     720
agatcccggg cgtgggctcg ctcagccaga gcaccatctg caggtttgag tctctcacgc     780
tgtcacacaa caacatgatc gcgctcaagc ccatcctgca ggcgtggctg gaggaagctg     840
agaaatccca ccgcgagaag ctcactaagc cggagctctt caatggcgcg gagaagaagc     900
gcaagcgcac gtccatcgcg cgcgccggaga agcgctctct ggaagcctac ttcgccatcc     960
agccaaggcc ctcctcggag aagatcgcgg ccatcgccga aaagctggat ctcaagaaaa    1020
atgtggtgcg cgtctggttc tgcaaccaga ggcagaaaca gaagaaggtg aaatactctg    1080
ccggcattta g                                                        1091
```

<210> SEQ ID NO 36
<211> LENGTH: 322
<212> TYPE: PRT
<213> ORGANISM: Mus musculus

<400> SEQUENCE: 36

```
Met Cys Ala Phe Tyr Leu Gln Leu Gln Ser Asn Ile Phe Gly Gly Leu
1               5                   10                  15

Asp Glu Ser Leu Leu Ala Arg Ala Glu Ala Leu Ala Ala Val Asp Ile
                20                  25                  30

Val Ser Gln Ser Lys Ser His His His Pro His His Ser Pro
            35                  40                  45

Phe Lys Pro Asp Ala Thr Tyr His Thr Met Asn Thr Ile Pro Cys Thr
        50                  55                  60

Ser Ala Ala Ser Ser Ser Ser Val Pro Ile Ser His Pro Ser Ala Leu
65              70                  75                  80

Ala Gly Thr His His His His His His His His His His His Gln
                85                  90                  95

Pro His Gln Ala Leu Glu Gly Glu Leu Leu Glu His Leu Ser Pro Gly
            100                 105                 110

Leu Ala Leu Gly Ala Met Ala Gly Pro Asp Gly Thr Val Val Ser Thr
        115                 120                 125

Pro Ala His Ala Pro His Met Ala Thr Met Asn Pro Met His Gln Ala
    130                 135                 140

Ala Leu Ser Met Ala His Ala His Gly Leu Pro Ser His Met Gly Cys
145                 150                 155                 160
```

```
Met Ser Asp Val Asp Ala Asp Pro Arg Asp Leu Glu Ala Phe Ala Glu
                165                 170                 175
Arg Phe Lys Gln Arg Arg Ile Lys Leu Gly Val Thr Gln Ala Asp Val
            180                 185                 190
Gly Ser Ala Leu Ala Asn Leu Lys Ile Pro Gly Val Gly Ser Leu Ser
        195                 200                 205
Gln Ser Thr Ile Cys Arg Phe Glu Ser Leu Thr Leu Ser His Asn Asn
    210                 215                 220
Met Ile Ala Leu Lys Pro Ile Leu Gln Ala Trp Leu Glu Glu Ala Glu
225                 230                 235                 240
Lys Ser His Arg Glu Lys Leu Thr Lys Pro Glu Leu Phe Asn Gly Ala
                245                 250                 255
Glu Lys Lys Arg Lys Arg Thr Ser Ile Ala Ala Pro Glu Lys Arg Ser
            260                 265                 270
Leu Glu Ala Tyr Phe Ala Ile Gln Pro Arg Pro Ser Ser Glu Lys Ile
        275                 280                 285
Ala Ala Ile Ala Glu Lys Leu Asp Leu Lys Lys Asn Val Val Arg Val
    290                 295                 300
Trp Phe Cys Asn Gln Arg Gln Lys Gln Lys Lys Val Lys Tyr Ser Ala
305                 310                 315                 320
Gly Ile

<210> SEQ ID NO 37
<211> LENGTH: 3110
<212> TYPE: DNA
<213> ORGANISM: Homo sapiens

<400> SEQUENCE: 37
agacctcggc acccgttcag actgacagca gaggcggcga aggagcgcgt agccgagatc      60
aggcgtacag agtccggagg cggcggcggg tgagctcaac ttcgcacagc ccttcccagc     120
tccagccccg gctggcccgg cacttctcgg agggtcccgg cagccgggac cagtgagtgc     180
ctctacggac cagcgccccg gcgggcggga agatgatgat gatgtccctg aacagcaagc     240
aggcgtttag catgccgcac ggcggcagcc tgcacgtgga gcccaagtac tcggcactgc     300
acagcacctc gccgggctcc tcggctccca tcgcgccctc ggccagctcc cccagcagct     360
cgagcaacgc tggtggtggc ggcggcggcg cggcggcgg cggcggcggc ggcggaggcc     420
gaagcagcag ctccagcagc agtggcagca gcggcggcgg gggctcggag gctatgcgga     480
gagcctgtct tccaaccca ccgagcaata tattcggcgg gctggatgag agtctgctgg     540
cccgcgccga ggctctggca gccgtggaca tcgtctccca gagcaagagc caccaccacc     600
atccacccca ccacagcccc ttcaaaccgg acgccaccta ccacactatg aataccatcc     660
cgtgcacgtc ggccgcctct tcttcatcgg tgcccatctc gcaccctttgc gcgttggcgg     720
gcacgcacca ccaccaccac catcaccacc accaccacca ccaaccgcac caggcgctgg     780
agggcgagct gctggagcac ctgagtcccg gctggcccct gggcgctatg cggggccccg     840
acggcgctgt ggtgtccacg ccggctcacg cgccgcacat ggccaccatg aaccccatgc     900
accaagcagc gctcagcatg gcccacgcgc acgggctgcc gtcgcacatg ggctgcatga     960
gcgacgtgga cgccgacccg cgggacctgg aggcattcgc cgagcgcttc aagcagcgac    1020
gcatcaagct gggggtgacc caggcagatg tgggctccgc gctggccaac ctcaagatcc    1080
ccggcgtggg ctcgcttagc cagagcacca tctgcaggtt cgagtccctc acactgtccc    1140
acaataatat gatcgcgctc aaacccatcc tgcaggcatg gctcgaggag gccgagaagt    1200
```

```
cccaccgcga gaagctcacc aagcctgaac tcttcaatgg cgcggagaag aagcgcaagc    1260
gcacgtccat cgctgcgcca gagaagcgct cgctcgaagc ctactttgcc attcagcctc    1320
ggccctcctc tgaaaagatc gccgccatcg cggagaagct ggacctgaag aaaaacgtgg    1380
tgcgcgtctg gttctgcaac cagaggcaga acagaaaaa aatgaaatat ccgccggca    1440
tttagaagac tcttggcctc tccagagacg ccccttccct cgtccgctct tttctctcct    1500
ctcttctgcc tcttttcact tttggcgact agaaacaatt ccagtaaatg tgaatctcga    1560
caaatcgagg actgaagagg gagcgaacga gcgaacaact gagcccaagc cggtgagaat    1620
gtgaaacagt ttctcaaagg aaagaataac aaaagatggt atttgtctgt tgtagcaaag    1680
ttgtcccttt gaaccccacc tcggcttctt cagaggaagt gtggagatgg ctgtttgcag    1740
gaaggcagac gagacagtgt ttaaaaagtc cacaagaatg atcaagtaag atttgttttt    1800
attcttacag acatcacccg tgttcaagtt taaaagtaca ctttgcaact atttttcaga    1860
aatagaaatt gattcaggac taaaacttta aactagagtt gatgcttaat gtgatagaga    1920
catctctaaa gtattttgaa ttttaaaaaa agatggcaga ttttctgcat ttacactgta    1980
tattatatat atatttttat tgtggttctt acccccttttt ccttctctga agtgttaatg    2040
cttaagaaaa gagttgcgcc tgctgtgttc actgatcttg aaagctatta ttagattatt    2100
gcagaacaac cctctgtaaa ttattaattt atctctctag caacttaatt ttgtgcacat    2160
tctaattaat taaacttctt ccgtctaaaa aaagtgggggg aaatgtatag ctagtaacgt    2220
tcaaaaaatt ttgtttgatg agtttaccga atttttacag cttccctcct atactgtgtt    2280
cctttttgacc catttgtata ttctcacttg aatgaagatt gttttttctct ttgttttttac    2340
tggtagtgtt ctgatttgtg agtcgacact cagtaatgga tgtcttaatc gtgtagacct    2400
gattcactgt ctgaagtatt gtttacttcg ttacatattt aatggggatt cccacattgt    2460
ccccatgaca catgagcgct ctcacttacc cttacacaca cacacacaca cacacacaca    2520
cctctaacag aagggaagaa gcagttggaa gcatgaccga tgcaccattt tctagtttta    2580
ggtgcatttg ccacttggtg tttgcccttc agattttaga tttcaccaag gtatttcagt    2640
cttccagttt tcaattgctt tgttggctac atgttaatat ttataggaat acttcagttt    2700
ttccttttgg aggtttgttt gtagaaaaac taatttgaac tataagaaag acagtgcact    2760
gcttgtaaat tcacattgtt tggaaaaatt cttttggaac aaaaaattag gtacatgata    2820
actggtacct tatctactgt aaatatttca ttaaaaatga tgcacacata gatatattct    2880
tacaaatttt gctgtattgc tgttctcttt gaggctctcc aaagtcttga gttctgtata    2940
tggcctggtt tcttgttttt attaatagat ggtttattta ctatggtaat gtattaattt    3000
attttggtg ttgttcgatt gtctttcatt gaagagataa ttttaatgtt ttattggcaa    3060
cgtatgctgc ttttttcatta aaatatgcta ttaaaattaa atggctttta              3110

<210> SEQ ID NO 38
<211> LENGTH: 410
<212> TYPE: PRT
<213> ORGANISM: Homo sapiens

<400> SEQUENCE: 38

Met Met Met Met Ser Leu Asn Ser Lys Gln Ala Phe Ser Met Pro His
1               5                   10                  15

Gly Gly Ser Leu His Val Glu Pro Lys Tyr Ser Ala Leu His Ser Thr
            20                  25                  30

Ser Pro Gly Ser Ser Ala Pro Ile Ala Pro Ser Ala Ser Ser Pro Ser
        35                  40                  45
```

Ser Ser Ser Asn Ala Gly Gly Gly Gly Gly Gly Gly Gly
    50                  55                  60

Gly Gly Gly Gly Gly Arg Ser Ser Ser Ser Ser Gly Ser Ser
65                  70                  75                  80

Gly Gly Gly Gly Ser Glu Ala Met Arg Arg Ala Cys Leu Pro Thr Pro
                85                  90                  95

Pro Ser Asn Ile Phe Gly Gly Leu Asp Glu Ser Leu Leu Ala Arg Ala
            100                 105                 110

Glu Ala Leu Ala Ala Val Asp Ile Val Ser Gln Ser Lys Ser His His
            115                 120                 125

His His Pro Pro His His Ser Pro Phe Lys Pro Asp Ala Thr Tyr His
            130                 135                 140

Thr Met Asn Thr Ile Pro Cys Thr Ser Ala Ala Ser Ser Ser Ser Val
145                 150                 155                 160

Pro Ile Ser His Pro Cys Ala Leu Ala Gly Thr His His His His
            165                 170                 175

His His His His His His Gln Pro His Gln Ala Leu Glu Gly Glu
            180                 185                 190

Leu Leu Glu His Leu Ser Pro Gly Leu Ala Leu Gly Ala Met Ala Gly
            195                 200                 205

Pro Asp Gly Ala Val Val Ser Thr Pro Ala His Ala Pro His Met Ala
210                 215                 220

Thr Met Asn Pro Met His Gln Ala Ala Leu Ser Met Ala His Ala His
225                 230                 235                 240

Gly Leu Pro Ser His Met Gly Cys Met Ser Asp Val Asp Ala Asp Pro
            245                 250                 255

Arg Asp Leu Glu Ala Phe Ala Glu Arg Phe Lys Gln Arg Ile Lys
            260                 265                 270

Leu Gly Val Thr Gln Ala Asp Val Gly Ser Ala Leu Ala Asn Leu Lys
            275                 280                 285

Ile Pro Gly Val Gly Ser Leu Ser Gln Ser Thr Ile Cys Arg Phe Glu
            290                 295                 300

Ser Leu Thr Leu Ser His Asn Asn Met Ile Ala Leu Lys Pro Ile Leu
305                 310                 315                 320

Gln Ala Trp Leu Glu Glu Ala Glu Lys Ser His Arg Glu Lys Leu Thr
            325                 330                 335

Lys Pro Glu Leu Phe Asn Gly Ala Glu Lys Lys Arg Lys Arg Thr Ser
            340                 345                 350

Ile Ala Ala Pro Glu Lys Arg Ser Leu Glu Ala Tyr Phe Ala Ile Gln
            355                 360                 365

Pro Arg Pro Ser Ser Glu Lys Ile Ala Ala Ile Ala Glu Lys Leu Asp
            370                 375                 380

Leu Lys Lys Asn Val Val Arg Val Trp Phe Cys Asn Gln Arg Gln Lys
385                 390                 395                 400

Gln Lys Arg Met Lys Tyr Ser Ala Gly Ile
                405                 410

<210> SEQ ID NO 39
<211> LENGTH: 1594
<212> TYPE: DNA
<213> ORGANISM: Mus musculus

<400> SEQUENCE: 39
caagcgagag ggcgagggga gcgctggcgc tgagcggcgc tcacttggag cgcggagagc    60

-continued

```
tagcaagacg agcttgattc catgtccccc gctgcctccc tgccagactc ccgaagatga    120
tggccatgaa cgccaagcac cgtttcggca tgcaccccgt actgcaagaa cccaaattct    180
ccagcctaca ctccggctct gaggccatgc gccgagtttg tctcccagcc cgcaggtac     240
gtagcggacg ataattaccg ctctaaggca cattttttga caggcactag cttcatgttt    300
ttttcatgtc gcccagaaca atcgccgctg tctgaacccc tcgccttgtc tcccccgcgc    360
tctctcgcgg ctctctctct ctctctctct ctctctctct ctctcattca                420
tgtctctgat ccacacgtct gttccaacag agaggctgcc tccgtattaa ttttatgac     480
ctgggctttg aggagaggca tctcggttgc ttgaaaatgt gttttaatcc tgagttgaca    540
gtattcccca ctgaccgtgc tgtgcgcctt ctcgcttgca gctgcagggt aatatatttg    600
gaagctttga tgagagcctg ctggcacgcg ccgaagctct ggcggcggtg gatatcgtct    660
cccacggcaa gaaccatccg ttcaagcccg acgccaccta ccataccatg agcagcgtgc    720
cctgcacttc tacctcgccc acggtgccca tctctcaccc ggctgcactc acctcgcacc    780
cgcatcacgc ggtacatcag ggcctcgagg gcgacttact tgagcacatc tcgcccacgc    840
tgagcgtgag tggcctaggg gccccggagc actcggtgat gccggcgcag atccaccccgc   900
atcatctagg cgccatgggc cacttgcatc aggccatggg catgagtcac ccgcatgccg    960
tagcaccgca cagtgccatg cccgcgtgtc tcagcgatgt ggagtcagac cctcgagagc   1020
tggaagcgtt cgccgagcgc ttcaagcaga ggcgcatcaa gttgggggtc acccaggcgg   1080
acgtgggcgc ggctttagcc aatcttaaga tccccggtgt gggctcgctc agccagagca   1140
ccatctgcag gttcgagtct cttactctgt cgcacaacaa catgatcgct ctcaagccgg   1200
tcctccaggc ctggctggag gaggccgagg ccgcctaccg agagaagaac agcaagccag   1260
agctcttcaa cggcagtgag cgtaagcgca aacgcacgtc catcgccgcg ccagagaagc   1320
gctcactcga agcctatttc gccatccagc cacgtccttc atccgagaag atcgcggcca   1380
tcgcggagaa actggacctt aaaaagaatg tggtgagggt ctggttctgt aaccagagac   1440
agaaacagaa acgaatgaaa tactctgctg tggactgatt gcggcgggtg ctgcgtccgg   1500
aggagcctgg agagcctaat gcatcgcccc cttccgatgg aggggagct tacgggacac    1560
tccagggtgt ttcctggcag gtcaggttct ttcc                                1594
```

<210> SEQ ID NO 40
<211> LENGTH: 338
<212> TYPE: PRT
<213> ORGANISM: Mus musculus

<400> SEQUENCE: 40

```
Met Met Ala Met Asn Ala Lys His Arg Phe Gly Met His Pro Val Leu
 1               5                  10                  15

Gln Glu Pro Lys Phe Ser Ser Leu His Ser Gly Ser Glu Ala Met Arg
             20                  25                  30

Arg Val Cys Leu Pro Ala Pro Gln Leu Gln Gly Asn Ile Phe Gly Ser
         35                  40                  45

Phe Asp Glu Ser Leu Leu Ala Arg Ala Glu Ala Leu Ala Ala Val Asp
     50                  55                  60

Ile Val Ser His Gly Lys Asn His Pro Phe Lys Pro Asp Ala Thr Tyr
 65                  70                  75                  80

His Thr Met Ser Ser Val Pro Cys Thr Ser Thr Ser Pro Thr Val Pro
                 85                  90                  95

Ile Ser His Pro Ala Ala Leu Thr Ser His Pro His Ala Val His
            100                 105                 110
```

Gln Gly Leu Glu Gly Asp Leu Leu Glu His Ile Ser Pro Thr Leu Ser
        115                 120                 125

Val Ser Gly Leu Gly Ala Pro Glu His Ser Val Met Pro Ala Gln Ile
130                 135                 140

His Pro His His Leu Gly Ala Met Gly His Leu His Gln Ala Met Gly
145                 150                 155                 160

Met Ser His Pro His Ala Val Ala Pro His Ser Ala Met Pro Ala Cys
                165                 170                 175

Leu Ser Asp Val Glu Ser Asp Pro Arg Glu Leu Glu Ala Phe Ala Glu
            180                 185                 190

Arg Phe Lys Gln Arg Arg Ile Lys Leu Gly Val Thr Gln Ala Asp Val
        195                 200                 205

Gly Ala Ala Leu Ala Asn Leu Lys Ile Pro Gly Val Gly Ser Leu Ser
    210                 215                 220

Gln Ser Thr Ile Cys Arg Phe Glu Ser Leu Thr Leu Ser His Asn Asn
225                 230                 235                 240

Met Ile Ala Leu Lys Pro Val Leu Gln Ala Trp Leu Glu Glu Ala Glu
                245                 250                 255

Ala Ala Tyr Arg Glu Lys Asn Ser Lys Pro Glu Leu Phe Asn Gly Ser
            260                 265                 270

Glu Arg Lys Arg Lys Arg Thr Ser Ile Ala Ala Pro Glu Lys Arg Ser
        275                 280                 285

Leu Glu Ala Tyr Phe Ala Ile Gln Pro Arg Pro Ser Ser Glu Lys Ile
    290                 295                 300

Ala Ala Ile Ala Glu Lys Leu Asp Leu Lys Lys Asn Val Val Arg Val
305                 310                 315                 320

Trp Phe Cys Asn Gln Arg Gln Lys Gln Lys Arg Met Lys Tyr Ser Ala
                325                 330                 335

Val Asp

<210> SEQ ID NO 41
<211> LENGTH: 120
<212> TYPE: DNA
<213> ORGANISM: Homo sapiens

<400> SEQUENCE: 41
atgatggcca tgaactccaa gcagcctttc ggcatgcacc cggtgctgca agaacccaaa      60
ttctccagtc tgcactctgg ctccgaggct atgcgccgag tctgtctccc agccccgcag     120

<210> SEQ ID NO 42
<211> LENGTH: 897
<212> TYPE: DNA
<213> ORGANISM: Homo sapiens

<400> SEQUENCE: 42
ctgcagggta atatatttgg aagctttgat gagagcctgc tggcacgcgc cgaagctctg      60
gcggcggtgg atatcgtctc ccacggcaag aaccatccgt tcaagcccga cgccacctac     120
cataccatga gcagcgtgcc ctgcacgtcc acttcgtcca ccgtgcccat ctcccaccca     180
gctgcgctca cctcacaccc tcaccacgcc gtgcaccagg gctcgaaggc gacctgctg      240 gagcacatct cgcccacgct gagtgtgagc ggcctgggcg ctccggaaca ctcggtgatg     300
cccgcacaga tccatccaca ccacctgggc gccatgggcc acctgcacca ggccatgggc     360
atgagtcacc cgcacaccgt ggcccctcat agcgccatgc ctgcatgcct cagcgacgtg     420
gagtcagacc cgcgcgagct ggaagccttc gccgagcgct tcaagcagcg gcgcatcaag     480

-continued

```
ctgggggtga cccaggcgga cgtgggcgcg gctctggcta atctcaagat ccccggcgtg    540
ggctcgctga gccaaagcac catctgcagg ttcgagtctc tcactctctc gcacaacaac    600
atgatcgctc tcaagccggt gctccaggcc tggttggagg aggccgaggc cgcctaccga    660
gagaagaaca gcaagccaga gctcttcaac ggcagcgaac ggaagcgcaa acgcacgtcc    720
atcgcggcgc cggagaagcg ttcactcgag gcctatttcg ctatccagcc acgtccttca    780
tctgagaaga tcgcggccat cgctgagaaa ctggacctta aaaagaacgt ggtgagagtc    840
tggttctgca accagagaca gaaacagaaa cgaatgaagt attcggctgt ccactga       897
```

<210> SEQ ID NO 43
<211> LENGTH: 338
<212> TYPE: PRT
<213> ORGANISM: Homo sapiens

<400> SEQUENCE: 43

```
Met Met Ala Met Asn Ser Lys Gln Pro Phe Gly Met His Pro Val Leu
1               5                   10                  15

Gln Glu Pro Lys Phe Ser Ser Leu His Ser Gly Ser Glu Ala Met Arg
            20                  25                  30

Arg Val Cys Leu Pro Ala Pro Gln Leu Gln Gly Asn Ile Phe Gly Ser
        35                  40                  45

Phe Asp Glu Ser Leu Leu Ala Arg Ala Glu Ala Leu Ala Ala Val Asp
    50                  55                  60

Ile Val Ser His Gly Lys Asn His Pro Phe Lys Pro Asp Ala Thr Tyr
65                  70                  75                  80

His Thr Met Ser Ser Val Pro Cys Thr Ser Thr Ser Ser Thr Val Pro
                85                  90                  95

Ile Ser His Pro Ala Ala Leu Thr Ser His Pro His Ala Val His
            100                 105                 110

Gln Gly Leu Glu Gly Asp Leu Leu Glu His Ile Ser Pro Thr Leu Ser
        115                 120                 125

Val Ser Gly Leu Gly Ala Pro Glu His Ser Val Met Pro Ala Gln Ile
    130                 135                 140

His Pro His His Leu Gly Ala Met Gly His Leu His Gln Ala Met Gly
145                 150                 155                 160

Met Ser His Pro His Thr Val Ala Pro His Ser Ala Met Pro Ala Cys
                165                 170                 175

Leu Ser Asp Val Glu Ser Asp Pro Arg Glu Leu Glu Ala Phe Ala Glu
            180                 185                 190

Arg Phe Lys Gln Arg Arg Ile Lys Leu Gly Val Thr Gln Ala Asp Val
        195                 200                 205

Gly Ala Ala Leu Ala Asn Leu Lys Ile Pro Gly Val Gly Ser Leu Ser
    210                 215                 220

Gln Ser Thr Ile Cys Arg Phe Glu Ser Leu Thr Leu Ser His Asn Asn
225                 230                 235                 240

Met Ile Ala Leu Lys Pro Val Leu Gln Ala Trp Leu Glu Glu Ala Glu
                245                 250                 255

Ala Ala Tyr Arg Glu Lys Asn Ser Lys Pro Glu Leu Phe Asn Gly Ser
            260                 265                 270

Glu Arg Lys Arg Lys Arg Thr Ser Ile Ala Ala Pro Glu Lys Arg Ser
        275                 280                 285

Leu Glu Ala Tyr Phe Ala Ile Gln Pro Arg Pro Ser Ser Glu Lys Ile
    290                 295                 300
```

```
Ala Ala Ile Ala Glu Lys Leu Asp Leu Lys Lys Asn Val Val Arg Val
305                 310                 315                 320

Trp Phe Cys Asn Gln Arg Gln Lys Gln Lys Arg Met Lys Tyr Ser Ala
            325                 330                 335

Val His

<210> SEQ ID NO 44
<211> LENGTH: 18
<212> TYPE: DNA
<213> ORGANISM: Homo sapiens

<400> SEQUENCE: 44
cacagctcat taacgcgc                                                 18

<210> SEQ ID NO 45
<211> LENGTH: 18
<212> TYPE: DNA
<213> ORGANISM: Homo sapiens

<400> SEQUENCE: 45
cactcctcat taacgcgc                                                 18

<210> SEQ ID NO 46
<211> LENGTH: 18
<212> TYPE: DNA
<213> ORGANISM: Homo sapiens

<400> SEQUENCE: 46
cacagctcat taagtcgc                                                 18

<210> SEQ ID NO 47
<211> LENGTH: 18
<212> TYPE: DNA
<213> ORGANISM: Homo sapiens

<400> SEQUENCE: 47
cacgcatgcg taatgcgc                                                 18

<210> SEQ ID NO 48
<211> LENGTH: 11
<212> TYPE: DNA
<213> ORGANISM: Homo sapiens
<220> FEATURE:
<221> NAME/KEY: misc_feature
<222> LOCATION: (5)..(7)
<223> OTHER INFORMATION: wherein n is a, c, g, or t

<400> SEQUENCE: 48
gcatnnntaa t                                                        11

<210> SEQ ID NO 49
<211> LENGTH: 11
<212> TYPE: DNA
<213> ORGANISM: Rattus norvegicus

<400> SEQUENCE: 49
gcataaataa t                                                        11

<210> SEQ ID NO 50
<211> LENGTH: 668
<212> TYPE: DNA
<213> ORGANISM: Mus musculus
<220> FEATURE:
<221> NAME/KEY: misc_feature
<222> LOCATION: (49)..(49)
```

```
<223> OTHER INFORMATION: wherein n is a, c, g, or t

<400> SEQUENCE: 50
tggagcagag gtttccattg tgtctctcag agcagaaacg gttggcctnt gtgttgcaac      60
cctcagcatc gcagtgctta tacgaattct gactacattc ctgatggtgt gtttcgctgg    120
ctttaacata aaggaaaaga tatttatttc ttttgcctgg cttccaaagg ccacggtcca    180
ggctgccatt ggctctgtgg ctctggacac ggcaagatcc cacggagaga agcagctgga    240
agactatggg atggatgtgc tgacggtggc attttttggcc atcctcatta cagcaccaat    300
tggaagccta ctgattggtt tgctgggtcc cagggttctt cagaaatctg aacatcgaac    360
cgaagaggag gttcaaggag agacttctgc acacattcag aggaagcctg aggattccat    420
tacggaagcc tgatggacca tgtttaccat cccaacccaa aggttttggc cctccaacaa    480
ccgggacaac tttacttccc tttgactcag aagaaaactt cccgtggaat ttcataagca    540
aacaaattag aaagctttac gctgctaaca gtacctcagg tgtttacttc ctcagaaaga    600
ccggaggaca ggttacttca gaaagtgaga gaaagtaatt tggacaaata aaacattcac    660
gattttgt                                                              668
```